(12) United States Patent
Föger et al.

(10) Patent No.: US 10,905,744 B2
(45) Date of Patent: Feb. 2, 2021

(54) PHARMACEUTICAL FORMULATIONS FOR THE ORAL DELIVERY OF PEPTIDE DRUGS

(71) Applicant: Cyprumed GmbH, Obsteig (AT)

(72) Inventors: Florian Föger, Obsteig (AT); Martin Werle, Bludenz (AT)

(73) Assignee: CYPRUMED GMBH, Obsteig (AT)

( * ) Notice: Subject to any disclaimer, the term of this patent is extended or adjusted under 35 U.S.C. 154(b) by 26 days.

(21) Appl. No.: 15/766,546

(22) PCT Filed: Oct. 7, 2016

(86) PCT No.: PCT/EP2016/074110
§ 371 (c)(1),
(2) Date: Apr. 6, 2018

(87) PCT Pub. No.: WO2017/060500
PCT Pub. Date: Apr. 13, 2017

(65) Prior Publication Data
US 2018/0280481 A1    Oct. 4, 2018

(30) Foreign Application Priority Data

Oct. 7, 2015   (EP) .................................... 15188838

(51) Int. Cl.
| | | |
|---|---|---|
| *A61K 38/26* | (2006.01) | |
| *A61K 38/29* | (2006.01) | |
| *A61K 33/26* | (2006.01) | |
| *A61K 33/30* | (2006.01) | |
| *A61K 33/34* | (2006.01) | |
| *A61K 9/48* | (2006.01) | |
| *A61K 45/06* | (2006.01) | |
| *A61K 38/03* | (2006.01) | |
| *A61K 38/04* | (2006.01) | |
| *A61K 47/02* | (2006.01) | |
| *A61K 38/02* | (2006.01) | |
| *A61K 47/26* | (2006.01) | |
| *A61K 47/12* | (2006.01) | |
| *A61K 47/40* | (2006.01) | |
| *A61K 47/20* | (2006.01) | |
| *A61K 38/095* | (2019.01) | |
| *A61K 38/08* | (2019.01) | |

(52) U.S. Cl.
CPC .............. *A61K 38/26* (2013.01); *A61K 9/485* (2013.01); *A61K 9/4858* (2013.01); *A61K 33/26* (2013.01); *A61K 33/30* (2013.01); *A61K 33/34* (2013.01); *A61K 38/02* (2013.01); *A61K 38/03* (2013.01); *A61K 38/04* (2013.01); *A61K 38/08* (2013.01); *A61K 38/095* (2019.01); *A61K 38/29* (2013.01); *A61K 45/06* (2013.01); *A61K 47/02* (2013.01); *A61K 47/12* (2013.01); *A61K 47/20* (2013.01); *A61K 47/26* (2013.01); *A61K 47/40* (2013.01); *A61K 2121/00* (2013.01); *A61K 2300/00* (2013.01)

(58) Field of Classification Search
CPC ........ A61K 38/26; A61K 9/485; A61K 47/20; A61K 47/40; A61K 47/12; A61K 47/26; A61K 38/02; A61K 47/02; A61K 38/04; A61K 38/03; A61K 38/08; A61K 45/06; A61K 9/4858; A61K 33/34; A61K 33/30; A61K 33/26; A61K 38/29; A61K 2300/00; A61K 2121/00
See application file for complete search history.

(56) References Cited

U.S. PATENT DOCUMENTS

| | | |
|---|---|---|
| 6,248,360 B1 | 6/2001 | Choi et al. |
| 2007/0087957 A1 | 4/2007 | Kidron |
| 2011/0311621 A1 | 12/2011 | Salama et al. |
| 2015/0031632 A1* | 1/2015 | Mo ..................... A61K 9/0056 514/21.1 |

(Continued)

FOREIGN PATENT DOCUMENTS

| | | |
|---|---|---|
| EP | 0943336 | 9/1999 |
| EP | 1 466 610 | 10/2004 |
| EP | 2 540 291 | 1/2013 |

(Continued)

OTHER PUBLICATIONS

Werle et al (International Journal of Pharmaceutics, 2009, 370, 26-32) (Year: 2009).*

(Continued)

*Primary Examiner* — Sudhakar Katakam
(74) *Attorney, Agent, or Firm* — Parker Highlander PLLC

(57) ABSTRACT

The present invention relates to improved pharmaceutical formulations, uses and methods for the oral delivery of peptide drugs with advantageously high bioavailability, safety and costeffectiveness. In particular, the invention provides a peptide drug having a molecular weight of equal to or less than 5 kDa for use as a medicament, wherein said peptide drug is to be administered orally in combination with a pharmaceutically acceptable copper salt/complex and/or a pharmaceutically acceptable zinc salt/complex and/or a pharmaceutically acceptable iron salt/complex, and with a pharmaceutically acceptable complexing agent. The invention also provides a pharmaceutical composition comprising: a peptide drug having a molecular weight of equal to or less than 5 kDa; a pharmaceutically acceptable copper salt/complex and/or a pharmaceutically acceptable zinc salt/complex and/or a pharmaceutically acceptable iron salt/complex; and a pharmaceutically acceptable complexing agent.

Figure 1:
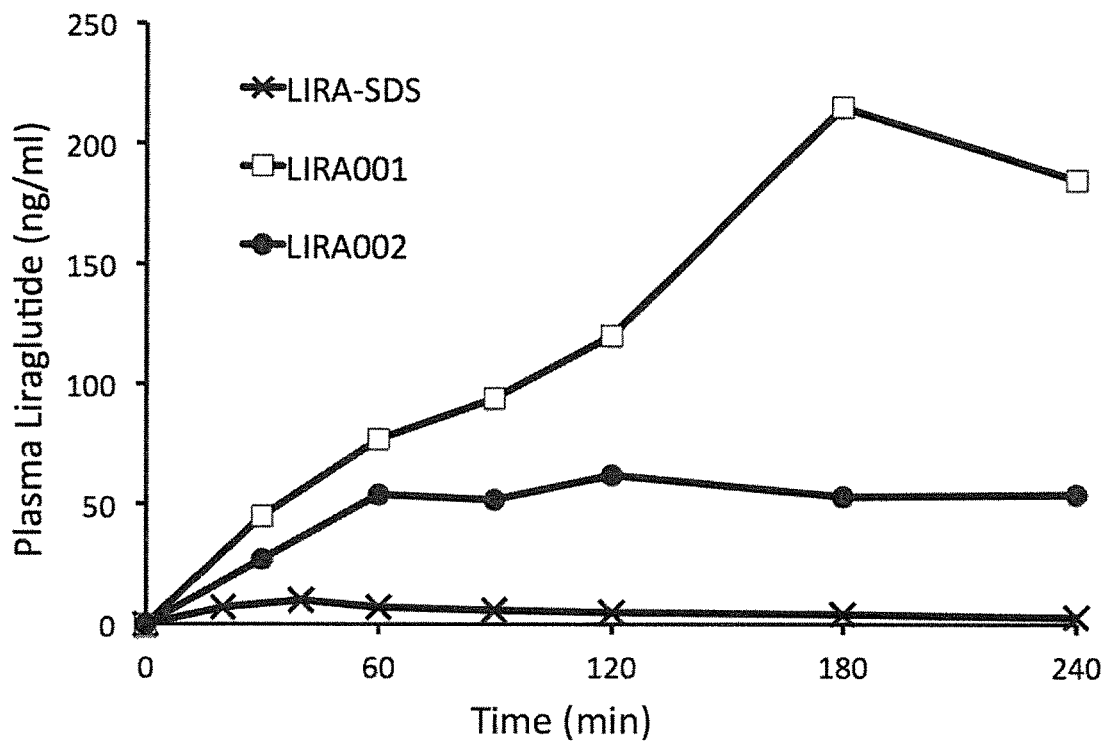

5 Claims, 20 Drawing Sheets
Specification includes a Sequence Listing.

(56) References Cited

U.S. PATENT DOCUMENTS

2017/0304195 A1    10/2017    Föger et al.

FOREIGN PATENT DOCUMENTS

| | | |
|---|---|---|
| JP | 2006-028031 | 2/2006 |
| JP | 2008-506782 | 3/2008 |
| JP | 2008-509933 | 4/2008 |
| JP | 2008-512381 | 4/2008 |
| JP | 2012-500196 | 1/2012 |
| JP | 2013-501071 | 1/2013 |
| JP | 2014-522412 | 9/2014 |
| WO | WO 2016/055550 | 4/1916 |
| WO | WO 2018/065634 | 4/1918 |
| WO | WO 1998/009645 | 12/1998 |
| WO | WO 2001/052894 | 7/2001 |
| WO | WO 2004/024226 | 3/2004 |
| WO | WO 2006/014673 | 2/2006 |
| WO | WO 2006/028991 | 3/2006 |
| WO | WO 2006/124047 | 11/2006 |
| WO | WO 2007/025332 | 3/2007 |
| WO | WO 2007/041481 | 4/2007 |
| WO | WO 2007/062494 | 6/2007 |
| WO | WO 2010/019266 | 2/2010 |
| WO | WO 2011/017502 | 2/2011 |
| WO | WO 2012/170828 | 12/2012 |

OTHER PUBLICATIONS

Katz et al (Nature, 391, Feb. 5, 1998, 608-612) (Year: 1998).*
Toyota et al (J.Mol.Biol., 2001, 305, 471-479) (Year: 2001).*
Steinert et al (Clinical Pharmacology & Therapeutics, vol. 86, No. 6, Dec. 2009, 644-650) (Year: 2009).*
Extended European Search Report issued in European Application No. 14187885.0, dated Feb. 18, 2015.
Extended European Search Report issued in European Application No. 15188838.5, dated Feb. 2, 2016.
Extended European Search Report issued in European Application No. 16192844.5, dated Mar. 31, 2017.
Fabio et al. "Heat-stable dry powder oxytocin formulations for delivery by oral inhalation," *AAPS Pharmscitech*, 16(6):1299-1306, 2015.
Harshad et al., "Recent techniques in nasal drug delivery: a review," *International Journal of Drug Development and Research*, 2(3):565-572, 2010.
Hogarth, "Metal-dithiocarbamate complexes: chemistry and biological activity," *Mini Reviews in Medicinal Chemistry*, 12(12):1202-1215, 2012.
Lind et al., "Oxidative inactivation of plasmin and other serine proteases by copper and ascorbate," *Blood*, 82(5):1522-1531, 1993.
Morales et al., "Novel strategies for the buccal delivery of macromolecules," *Drug Development and Industrial Pharmacy*, 40(5):579-590, 2014.
Park et al., "Oral protein delivery: current status and future prospect," *Reactive & Functional Polymers*, 71:280-287, 2011.
PCT International Preliminary Report on Patentability issued in International Application No. PCT/EP2016/074110, dated Apr. 19, 2018.
PCT International Preliminary Report on Patentability issued in International Application No. PCT/EP2015/073196, dated Apr. 20, 2017.
PCT International Search Report and Written Opinion issued in International Application No. PCT/EP2016/074110, dated Dec. 21, 2016.
PCT International Search Report and Written Opinion issued in International Application No. PCT/EP2017/075703, dated Feb. 12, 2018.
PCT International Search Report and Written Opinion issued in International Application No. PCT/EP2015/073196, dated Feb. 17, 2016.
Prakash et al., "Selective inactivation of serine proteases by nonheme iron complexes," *Inorganic Chemistry*, 50(9):3934-3945, 2011.
Sarkar, "Drug metabolism in the nasal mucosa," *Pharmaceutical Research*, 9(1):1-9, 1992.
Wetterholm et al., "Zinc and other divalent-cations inhibit purified leukotriene $A_4$ hydrolase and leukotriene $B_4$ biosynthesis in human polymorphonuclear leukocytes," *Archives of Biochemistry and Biophysics*, 311(2):263-271, 1994.
Wieninger-Rustemeyer et al., "Trypsin activity in the small intestine of rats after application of copper and zinc," *Biological Trace Element Research*, 2(4):247-254, 1980.
Office Communication in corresponding Japanese patent application No. 2018-517702; dated Aug. 31, 2020, 7pgs (English translation).

* cited by examiner

▲ 0.035 mg/ml copper as copper gluconate

✕ 0.25 mg/ml lauryl-glutamate

● 0.035 mg/ml copper as copper gluconate + 0.25 mg/ml lauryl-glutamate

PHARMACEUTICAL FORMULATIONS FOR THE ORAL DELIVERY OF PEPTIDE DRUGS

This application is a national phase application under 35 U.S.C. § 371 of International Application No. PCT/EP2016/074110, filed Oct. 7, 2016, which claims benefit of European Application No. 15188838.5, filed Oct. 7, 2015, the entire contents of each of which are hereby incorporated by reference.

The present invention relates to improved pharmaceutical formulations, uses and methods for the oral delivery of peptide drugs with advantageously high bioavailability, safety and cost-effectiveness. In particular, the invention provides a peptide drug having a molecular weight of equal to or less than 5 kDa for use as a medicament, wherein said peptide drug is to be administered orally in combination with a pharmaceutically acceptable copper salt/complex and/or a pharmaceutically acceptable zinc salt/complex and/or a pharmaceutically acceptable iron salt/complex, and with a pharmaceutically acceptable complexing agent. The invention also provides a pharmaceutical composition comprising: a peptide drug having a molecular weight of equal to or less than 5 kDa; a pharmaceutically acceptable copper salt/complex and/or a pharmaceutically acceptable zinc salt/complex and/or a pharmaceutically acceptable iron salt/complex; and a pharmaceutically acceptable complexing agent.

A growing number of peptides and proteins have been made available as therapeutic agents. However, the full potential of these biological drugs has not been realized because they are limited to parenteral injection. Ideally, the oral route of administration would be preferred. Oral administration is the most common and popular method of administering drugs due to its simplicity and convenience for patients. However, the gastrointestinal tract degrades these macromolecules and prevents their absorption as intact entities. Enzymatic degradation throughout the gastrointestinal tract and poor permeability through the epithelial cells are the main reasons for their low oral bioavailability.

A number of different approaches have been proposed to improve the oral bioavailability of such therapeutic peptides and proteins, including the use of absorption enhancing technologies or the use of protease inhibitors such as soybean trypsin inhibitor, aprotinin, bowman birk inhibitor, bacitracin, camostat mesilate and amastatin (Renukuntla J et al., *Int J Pharm.* 2013, 447(1-2):75-93; US 2007/0087957 A1). However, due to safety concerns none of these protease inhibitors has succeeded as additive in commercial peptide or polypeptide drug delivery applications. The protease inhibitors described in known oral polypeptide drug delivery technologies and their toxicity and potential side effects are summarized in the following.

Soybean trypsin inhibitor: Soy is widely accepted as one of "the big eight" allergens that causes immediate reactions such as coughing, sneezing, runny nose, hives, diarrhea, facial swelling, shortness of breath, swollen tongue, difficulty of swallowing, lowered blood pressure, excessive perspiration, fainting, anaphylactic shock and even death; the number of people suffering from soy allergies has been increasing steadily since the 1980s (Moroz LA et al., *N Engl J Med.* 1980, 302(20):1126-8; Foucard T et al., *Allergy.* 1999, 54(3):261-5; Ramesh S, *Clin Rev Allergy Immunol.* 2008, 34(2):217-30).

Bowman birk inhibitor: Another soybean derived protease inhibitor is the Bowman birk inhibitor. Bowman birk inhibitor is known to have oral bioavailability even without absorption enhancing additives and could therefore exert unwanted systemic protease inhibition after oral intake. Systemic inhibition of serine proteases such as plasmin could increase the risk of thrombosis. There are also reports about the formation of antibodies against bowman birk inhibitor (Wan XS et al., *Nutr Cancer.* 2002, 43(2):167-73).

Aprotinin: There have been several concerns about the safety of aprotinin. Anaphylaxis occurs at a rate of 1:200 in first-time use (Mandy A M et al., *Br J Anaesth.* 2004, 93(6):842-58). A study performed in cardiac surgery patients reported in 2006 showed that there was a risk of acute renal failure, myocardial infarction and heart failure, as well as stroke and encephalopathy (Mangano D T et al., *N Engl J Med.* 2006, 354(4):353-65). Moreover, a study comparing aprotinin with aminocaproic acid found that mortality was increased by 64% (Schneeweiss S et al., *N Engl J Med.* 2008, 358(8):771-83).

The use of these protease inhibitors thus poses potential health risks and should preferably be avoided. Further disadvantages are high manufacturing costs, heterogeneity and regulatory hurdles. Furthermore, most protein based inhibitors have to be co-administered excessively in large amounts because these compounds are susceptible to enzymatic degradation in the gut. Even large amounts of these inhibitors may not be adequate to reduce protease activity (Renukuntla Jet al., *Int J Pharm.* 2013, 447(1-2):75-93).

It has also been proposed to use protease inhibitors such as bacitracin (having antibiotic activity), camostat mesilate (effective in the treatment of pancreatitis) or amastatin (having antibacterial activity) which, however, all have pharmacological effects on their own. Chronic administration of these protease inhibitors in oral peptide or polypeptide formulations would therefore not be acceptable (Renukuntla J et al., *Int J Pharm.* 2013, 447(1-2):75-93; US 2007/0087957 A1).

Another disadvantage of protease inhibitors used so far in oral drug delivery systems is their limitation to inactivate just certain intestinal proteases. However, in order to efficiently deliver therapeutic peptide drugs in intact form via the oral route, more than just one or two of the intestinal serine proteases, such as trypsin, chymotrypsin, aminopeptidase, carboxypeptidase, elastase and dipeptidyl-4-peptidase, and also other enzymes such as insulin degrading enzyme need to be transiently inactivated. Otherwise, oral bioavailability will remain very low.

Thus, there is still an urgent need for simple, very safe, more efficient and less expensive means and methods to deliver therapeutic peptide drugs via the oral route.

It has further been described that aqueous solutions of copper in the presence of ascorbate reduce the activity of plasmin and other serine proteases in the blood (Lind S E et al., *Blood.* 1993, 82(5):1522-31). However, the use of copper and a complexing agent in pharmaceutical compositions, particularly for the oral delivery of peptide drugs, has never been proposed.

Certain pharmaceutical formulations for absorption through oral mucosae have been described in WO 2007/062494, and specific insulin formulations have further been proposed in WO 2007/041481.

Moreover, specific formulations of certain peptide drugs have also been disclosed in US 2015/0031632, U.S. Pat. No. 6,248,360, US 2011/0311621, and Fabio K et al., *AAPS PharmSciTech.* 2015; 16(6):1299-306. The formulations of peptide drugs taught in US 2011/0311621, however, do not contain any salt or complex of copper, zinc or iron; in fact, the use of certain zinc or iron salts is described in this document specifically and exclusively in connection with a formulation of the non-peptidic drug aliskiren. Fabio K et al., 2015 (loc. cit.) relates to the administration of certain oxytocin formulations via inhalation, i.e. via the pulmonary route, but not to any peroral administration of such formulations. Morales J O et al., *Drug Dev Ind Pharm.* 2014; 40(5):579-90 discusses strategies for facilitating the buccal delivery of therapeutic macromolecules.

In the context of the present invention, it has been found that a combination of the trace element copper, zinc or iron with a pharmaceutically acceptable complexing agent, optionally further in combination with a mucosal absorption enhancer that is soluble in the presence of the copper, zinc or iron, results in a surprisingly high and advantageous oral bioavailability of different peptide drugs, as also shown in the working examples (see, in particular, Examples 2, 3, 5 to 8 and 34 as well as FIG. 1). The required amounts of copper, zinc or iron do not exceed approved intake levels (including approved daily intake levels) of these trace elements and can therefore be regarded as safe. Moreover, copper, zinc or iron in combination with a complexing agent exert an inhibitory effect on serine proteases in the gastrointestinal tract but do not show a systemic inhibitory effect, which provides a further safety improvement as compared to the above-discussed protease inhibitors. Furthermore, copper, zinc or iron as well as complexing agents as described further below can be provided at considerably lower manufacturing costs than the above-discussed protease inhibitors that have previously been suggested for the oral delivery of peptide drugs.

The present invention thus solves the problem of providing improved pharmaceutical formulations, uses and methods for the oral delivery of peptide drugs, allowing the oral administration of a wide range of different peptide drugs with advantageously high bioavailability, safety, storage stability and cost-effectiveness.

Accordingly, in a first aspect, the present invention provides a peptide drug having a molecular weight of equal to or less than 5 kDa for use as a medicament, wherein said peptide drug is to be administered orally in combination with: a pharmaceutically acceptable copper salt/complex and/or a pharmaceutically acceptable zinc salt/complex and/or a pharmaceutically acceptable iron salt/complex; and a pharmaceutically acceptable complexing agent.

In accordance with this first aspect, the invention also relates to a peptide drug having a molecular weight of equal to or less than 5 kDa for use in therapy, wherein said peptide drug is to be administered orally in combination with: a pharmaceutically acceptable copper salt/complex and/or a pharmaceutically acceptable zinc salt/complex and/or a pharmaceutically acceptable iron salt/complex; and a pharmaceutically acceptable complexing agent. The invention likewise provides a peptide drug having a molecular weight of equal to or less than 5 kDa for use in the treatment or prevention of a disease/disorder, wherein said peptide drug is to be administered orally and in combination with: a pharmaceutically acceptable copper salt/complex and/or a pharmaceutically acceptable zinc salt/complex and/or a pharmaceutically acceptable iron salt/complex; and a pharmaceutically acceptable complexing agent. The invention further relates to a peptide drug having a molecular weight of equal to or less than 5 kDa for use as a medicament (or for use in therapy, or for use in the treatment or prevention of a disease/disorder), wherein said peptide drug is to be administered orally in combination with a pharmaceutically acceptable copper salt/complex and a pharmaceutically acceptable complexing agent. Moreover, the present invention also provides a peptide drug having a molecular weight of equal to or less than 5 kDa for use as a medicament (or for use in therapy, or for use in the treatment or prevention of a disease/disorder), wherein said peptide drug is to be administered orally in combination with a pharmaceutically acceptable zinc salt/complex and a pharmaceutically acceptable complexing agent. The invention also provides a peptide drug having a molecular weight of equal to or less than 5 kDa for use as a medicament (or for use in therapy, or for use in the treatment or prevention of a disease/disorder), wherein said peptide drug is to be administered orally in combination with a pharmaceutically acceptable iron salt/complex and a pharmaceutically acceptable complexing agent. The invention furthermore relates to the use of a peptide drug having a molecular weight of equal to or less than 5 kDa in the preparation of a medicament which is to be administered orally in combination with: a pharmaceutically acceptable copper salt/complex and/or a pharmaceutically acceptable zinc salt/complex and/or a pharmaceutically acceptable iron salt/complex; and a pharmaceutically acceptable complexing agent. The invention likewise refers to the use of a peptide drug having a molecular weight of equal to or less than 5 kDa in the preparation of a medicament for the treatment or prevention of a disease/disorder, which is to be administered orally and in combination with: a pharmaceutically acceptable copper salt/complex and/or a pharmaceutically acceptable zinc salt/complex and/or a pharmaceutically acceptable iron salt/complex; and a pharmaceutically acceptable complexing agent.

In a second aspect, the present invention relates to a pharmaceutically acceptable copper salt/complex for use as a medicament (or for use in therapy, or for use in the treatment or prevention of a disease/disorder), wherein said copper salt/complex is to be administered orally in combination with: a peptide drug having a molecular weight of equal to or less than 5 kDa; and a pharmaceutically acceptable complexing agent.

In accordance with this second aspect, the invention also relates to the use of a pharmaceutically acceptable copper salt/complex in the preparation of a medicament which is to be administered orally in combination with: a peptide drug having a molecular weight of equal to or less than 5 kDa; and a pharmaceutically acceptable complexing agent. The invention further relates to the use of a pharmaceutically acceptable copper salt/complex in the preparation of a medicament for the treatment or prevention of a disease/disorder, which is to be administered orally in combination with: a peptide drug having a molecular weight of equal to or less than 5 kDa; and a pharmaceutically acceptable complexing agent.

In a third aspect, the invention provides a pharmaceutically acceptable zinc salt/complex for use as a medicament (or for use in therapy, or for use in the treatment or prevention of a disease/disorder), wherein said zinc salt/complex is to be administered orally in combination with: a peptide drug having a molecular weight of equal to or less than 5 kDa; and a pharmaceutically acceptable complexing agent.

In accordance with this third aspect, the invention further relates to the use of a pharmaceutically acceptable zinc salt/complex in the preparation of a medicament which is to be administered orally in combination with: a peptide drug having a molecular weight of equal to or less than 5 kDa; and a pharmaceutically acceptable complexing agent. The invention likewise relates to the use of a pharmaceutically acceptable zinc salt/complex in the preparation of a medicament for the treatment or prevention of a disease/disorder, which is to be administered orally in combination with: a peptide drug having a molecular weight of equal to or less than 5 kDa; and a pharmaceutically acceptable complexing agent.

In a fourth aspect, the invention provides a pharmaceutically acceptable iron salt/complex for use as a medicament (or for use in therapy, or for use in the treatment or prevention of a disease/disorder), wherein said iron salt/complex is to be administered orally in combination with: a peptide drug having a molecular weight of equal to or less than 5 kDa; and a pharmaceutically acceptable complexing agent.

In accordance with this fourth aspect, the invention further relates to the use of a pharmaceutically acceptable iron salt/complex in the preparation of a medicament which is to be administered orally in combination with: a peptide drug having a molecular weight of equal to or less than 5 kDa; and a pharmaceutically acceptable complexing agent. The invention likewise relates to the use of a pharmaceutically acceptable iron salt/complex in the preparation of a medicament for the treatment or prevention of a disease/disorder, which is to be administered orally in combination with: a peptide drug having a molecular weight of equal to or less than 5 kDa; and a pharmaceutically acceptable complexing agent.

In a fifth aspect, the present invention provides a pharmaceutically acceptable complexing agent for use as a medicament (or for use in therapy, or for use in the treatment or prevention of a disease/disorder), wherein said complexing agent is to be administered orally in combination with: a peptide drug having a molecular weight of equal to or less than 5 kDa; and a pharmaceutically acceptable copper salt/complex and/or a pharmaceutically acceptable zinc salt/complex and/or a pharmaceutically acceptable iron salt/complex.

In accordance with this fifth aspect, the invention also relates to a pharmaceutically acceptable complexing agent for use as a medicament (or for use in therapy, or for use in the treatment or prevention of a disease/disorder), wherein said complexing agent is to be administered orally in combination with a pharmaceutically acceptable copper salt/complex and a peptide drug having a molecular weight of equal to or less than 5 kDa. The invention likewise provides a pharmaceutically acceptable complexing agent for use as a medicament (or for use in therapy, or for use in the treatment or prevention of a disease/disorder), wherein said complexing agent is to be administered orally in combination with a pharmaceutically acceptable zinc salt/complex and a peptide drug having a molecular weight of equal to or less than 5 kDa. The invention further provides a pharmaceutically acceptable complexing agent for use as a medicament (or for use in therapy, or for use in the treatment or prevention of a disease/disorder), wherein said complexing agent is to be administered orally in combination with a pharmaceutically acceptable iron salt/complex and a peptide drug having a molecular weight of equal to or less than 5 kDa. Moreover, the invention refers to the use of a pharmaceutically acceptable complexing agent in the preparation of a medicament which is to be administered orally in combination with: a peptide drug having a molecular weight of equal to or less than 5 kDa; and a pharmaceutically acceptable copper salt/complex and/or a pharmaceutically acceptable zinc salt/complex and/or a pharmaceutically acceptable iron salt/complex. The invention further relates to the use of a pharmaceutically acceptable complexing agent in the preparation of a medicament for the treatment or prevention of a disease/disorder, which is to be administered orally in combination with: a peptide drug having a molecular weight of equal to or less than 5 kDa; and a pharmaceutically acceptable copper salt/complex and/or a pharmaceutically acceptable zinc salt/complex and/or a pharmaceutically acceptable iron salt/complex.

In a sixth aspect, the present invention provides a pharmaceutical composition comprising: a peptide drug having a molecular weight of equal to or less than 5 kDa; a pharmaceutically acceptable copper salt/complex and/or a pharmaceutically acceptable zinc salt/complex and/or a pharmaceutically acceptable iron salt/complex; and a pharmaceutically acceptable complexing agent.

In accordance with this sixth aspect, the invention also relates to a pharmaceutical composition comprising: a peptide drug having a molecular weight of equal to or less than 5 kDa; a pharmaceutically acceptable copper salt/complex; and a pharmaceutically acceptable complexing agent. The invention likewise refers to a pharmaceutical composition comprising: a peptide drug having a molecular weight of equal to or less than 5 kDa; a pharmaceutically acceptable zinc salt/complex; and a pharmaceutically acceptable complexing agent. The invention further relates to a pharmaceutical composition comprising: a peptide drug having a molecular weight of equal to or less than 5 kDa; a pharmaceutically acceptable iron salt/complex; and a pharmaceutically acceptable complexing agent. The pharmaceutical compositions of this sixth aspect are preferably pharmaceutical compositions for oral administration.

In a seventh aspect, the invention provides a pharmaceutical dosage form comprising: a peptide drug having a molecular weight of equal to or less than 5 kDa; a pharmaceutically acceptable copper salt/complex and/or a pharmaceutically acceptable zinc salt/complex and/or a pharmaceutically acceptable iron salt/complex; and a pharmaceutically acceptable complexing agent; wherein the peptide drug is physically separated from the pharmaceutically acceptable copper salt/complex, the pharmaceutically acceptable zinc salt/complex and the pharmaceutically acceptable iron salt/complex within the pharmaceutical dosage form. The pharmaceutical dosage form of this seventh aspect is preferably a pharmaceutical dosage form for oral administration.

In an eighth aspect, the present invention provides a method of treating or preventing a disease/disorder, the method comprising orally administering, to a subject in need thereof, a peptide drug having a molecular weight of equal to or less than 5 kDa, a pharmaceutically acceptable copper salt/complex and/or a pharmaceutically acceptable zinc salt/complex and/or a pharmaceutically acceptable iron salt/complex, and a pharmaceutically acceptable complexing agent. It will be understood that the disease/disorder to be treated or prevented is a disease/disorder susceptible to treatment or prevention with said peptide drug.

In accordance with this eighth aspect, the invention further relates to a method of orally delivering a peptide drug having a molecular weight of equal to or less than 5 kDa, the method comprising orally administering said peptide drug in combination with a pharmaceutically acceptable copper salt/complex and/or a pharmaceutically acceptable zinc salt/complex and/or a pharmaceutically acceptable iron salt/complex, and with a pharmaceutically acceptable complexing agent, to a subject in need thereof. The invention also provides a method of facilitating the oral delivery of a peptide drug having a molecular weight of equal to or less than 5 kDa, the method comprising orally administering said peptide drug in combination with a pharmaceutically acceptable copper salt/complex and/or a pharmaceutically acceptable zinc salt/complex and/or a pharmaceutically acceptable iron salt/complex, and with a pharmaceutically acceptable complexing agent, to a subject in need thereof. Furthermore, the invention relates to a method of administering a peptide drug having a molecular weight of equal to or less than 5 kDa, the method comprising orally administering said peptide drug in combination with a pharmaceutically acceptable copper salt/complex and/or a pharmaceutically acceptable zinc salt/complex and/or a pharmaceutically acceptable iron salt/complex, and with a pharmaceutically acceptable complexing agent, to a subject in need thereof.

The following detailed description applies to all embodiments of the present invention, including all embodiments according to each one of the first, second, third, fourth, fifth, sixth, seventh and eighth aspect as described herein above.

The peptide drug to be administered in accordance with the invention has a molecular weight of equal to or less than 5 kDa (such as, e.g., equal to or less than about 4.5 kDa, or equal to or less than about 4 kDa, or equal to or less than about 3.5 kDa, or equal to or less than about 3 kDa, or equal to or less than about 2.5 kDa, or equal to or less than about 2 kDa, or equal to or less than about 1.5 kDa, or equal to or less than about 1 kDa, or equal to or less than about 500 Da). It is preferred that the peptide drug has a maximum molecular weight of equal to or less than about 4.5 kDa, more preferably equal to or less than about 4 kDa, even more preferably equal to or less than about 3.5 kDa, and yet even more preferably equal to or less than about 3 kDa. It is furthermore preferred that the peptide drug has a minimum molecular weight of equal to or greater than about 300 Da, more preferably equal to or greater than about 500 Da, even more preferably equal to or greater than about 800 Da, and yet even more preferably equal to or greater than about 1 kDa. Accordingly, it is particularly preferred that the peptide drug has a molecular weight of about 300 Da to about 4.5 kDa, more preferably about 500 Da to about 4 kDa, even more preferably about 800 Da to about 3.5 kDa, and yet even more preferably about 1 kDa to about 3 kDa.

The molecular weight of the peptide drug is indicated herein in dalton (Da), which is an alternative name for the unified atomic mass unit (u). A molecular weight of, e.g., 500 Da is thus equivalent to 500 g/mol. The term "kDa" (kilodalton) refers to 1000 Da.

The molecular weight of the peptide drug can be determined using methods known in the art, such as, e.g., mass spectrometry (e.g., electrospray ionization mass spectrometry (ESI-MS) or matrix-assisted laser desorption/ionization mass spectrometry (MALDI-MS)), gel electrophoresis (e.g., polyacrylamide gel electrophoresis using sodium dodecyl sulfate (SDS-PAGE)), hydrodynamic methods (e.g., gel filtration chromatography or gradient sedimentation), or static light scattering (e.g., multi-angle light scattering (MALS)). It is preferred that the molecular weight of the peptide drug is determined using mass spectrometry.

The peptide drug may be any peptide that is suitable to be used as a medicament. For example, the peptide drug may be a linear peptide drug or a cyclic peptide drug (e.g., a cyclic peptide drug that is cyclized via at least one ester linkage). It may also be a modified or derivatized peptide drug, such as a PEGylated peptide drug or a fatty acid acylated peptide drug or a fatty diacid acylated peptide drug, or it may be an unmodified peptide drug. In particular, it may be unmodified at its N-terminus and/or at its C-terminus, i.e., it may have a free N-terminus (—$NH_2$) and/or a free C-terminus (—COOH); the peptide drug may thus have a free (unmodified) N-terminus, or it may have a free (unmodified) C-terminus, or it may have both a free N-terminus and a free C-terminus. Moreover, the peptide drug may be free of histidine residues and/or free of cysteine residues. It is generally preferred that the peptide drug is water-soluble, particularly at neutral pH (i.e., at about pH 7). It is furthermore preferred that the peptide drug has at least one serine protease cleavage site, i.e., that the peptide drug comprises one or more amino acid residue(s) amenable or prone to cleavage by a serine protease (particularly an intestinal serine protease, such as trypsin, chymotrypsin, aminopeptidase, carboxypeptidase, elastase and/or dipeptidyl-4-peptidase). The term "peptide drug" is used herein synonymously with "therapeutic peptide" and "therapeutic peptide drug".

The peptide drug is preferably selected from glucagon-like peptide-1 (GLP-1), a GLP-1 analog (e.g., an acylated GLP-1 analog or a diacylated GLP-1 analog, or a long-acting albumin-binding fatty acid-derivatized GLP-1 analog) or GLP-1 agonist (also referred to as "glucagon-like peptide-1 receptor agonist" or "GLP-1 receptor agonist"), semaglutide, liraglutide, exenatide, exendin-4, lixisenatide, taspoglutide, langlenatide, GLP-1(7-37), GLP-1(7-36)$NH_2$, a dual agonist of the GLP-1 receptor and the glucagon receptor, oxyntomodulin, GLP-2, a GLP-2 agonist or analog (e.g., teduglutide or elsiglutide), amylin, an amylin analog, pramlintide, a somatostatin analog (e.g., octreotide, lanreotide, or pasireotide), goserelin (e.g., goserelin acetate), buserelin, peptide YY (PYY), a PYY analog, glatiramer (e.g., glatiramer acetate), leuprolide (e.g., leuprolide acetate), desmopressin (e.g., desmopressin acetate, particularly desmopressin monoacetate trihydrate), a glycopeptide antibiotic (e.g., a glycosylated cyclic or polycyclic nonribosomal peptide such as vancomycin, teicoplanin, telavancin, bleomycin, ramoplanin, or decaplanin), bortezomib, cosyntropin, sermorelin, luteinizing-hormone-releasing hormone (LHRH; also referred to as "gonadotropin-releasing hormone"), calcitonin (e.g., calcitonin-salmon), pentagastrin, oxytocin, neseritide, enfuvirtide, eptifibatide, cyclosporine, glucagon, viomycin, thyrotropin-releasing hormone (TRH), leucine-enkephalin, methionine-enkephalin, substance P (CAS no. 33507-63-0), a parathyroid hormone (PTH) fragment (e.g., teriparatide (also referred to as "PTH(1-34)"), PTH(1-31), or PTH(2-34)), linaclotide, carfilzomib, icatibant, cilengitide, a prostaglandin F2α receptor modulator (e.g., PDC31), and pharmaceutically acceptable salts thereof. If the subject/patient to be treated is a human and if the peptide drug is an endogenous peptide in human beings (i.e., occurs naturally in humans; such as, e.g., glucagon), it is furthermore preferred to use a human isoform of the corresponding peptide (which may, e.g., be recombinantly expressed or chemically synthesized). Further examples of the peptide drug include, in particular, glucose-dependent insulinotropic polypeptide (also referred to as "gastric inhibitory polypeptide" or GIP), a dual GLP-1 analog, a dual agonist of the glucagon-like peptide 1 receptor and the glucagon receptor (a GLP-1R/GCGR dual agonist), a GLP1/glucagon receptor co-agonist (such as, e.g., any one of the compounds referred to in WO 2015/185640), a dual agonist of the glucagon-like peptide 1 receptor and the gastric inhibitory polypeptide receptor (a GLP-1R/GIPR dual agonist; such as, e.g., any one of the compounds referred to in WO 2013/164483), a GLP1/GIP receptor co-agonist, an exendin-4 peptide analog (particularly an exendin-4 peptide analog which is a GLP-1R/GIPR dual agonist; such as, e.g., any one of the exendin-4 peptide analogs referred to in WO 2015/086728), an exendin-4 derivative (particularly an exendin-4 derivative which is a GLP-1R/GCGR dual agonist; such as, e.g., any one of the exendin-4 derivatives referred to in WO 2015/155139 or in WO 2015/086733), or a pharmaceutically acceptable salt of any of these agents. A further example of the peptide drug is elamipretide. Further examples of the peptide drug are cyclotides (which are peptides characterized by their head-to-tail cyclised peptide backbone and the interlocking arrangement of their disulfide bonds), including, e.g., a cyclotide having at least two disulfide bonds (and preferably a cyclotide having three disulfide bonds).

More preferably, the peptide drug is selected from GLP-1, a GLP-1 analog (e.g., an acylated GLP-1 analog or a diacylated GLP-1 analog, or a long-acting albumin-binding fatty acid-derivatized GLP-1 analog), a GLP-1 agonist, semaglutide, liraglutide, exenatide, exendin-4, lixisenatide, taspoglutide, langlenatide, GLP-1(7-37), GLP-1(7-36)NH$_2$, a dual agonist of the GLP-1 receptor and the glucagon receptor, oxyntomodulin, GLP-2, a GLP-2 agonist or analog (e.g., teduglutide or elsiglutide), amylin, an amylin analog, pramlintide, a somatostatin analog (e.g., octreotide, lanreotide, or pasireotide), goserelin (e.g., goserelin acetate), buserelin, peptide YY (PYY), a PYY analog, glatiramer (e.g., glatiramer acetate), leuprolide (e.g., leuprolide acetate), desmopressin (e.g., desmopressin acetate, particularly desmopressin monoacetate trihydrate), teicoplanin, telavancin, bleomycin, ramoplanin, decaplanin, bortezomib, cosyntropin, sermorelin, luteinizing-hormone-releasing hormone (LHRH), calcitonin (e.g., calcitonin-salmon), pentagastrin, neseritide, enfuvirtide, eptifibatide, cyclosporine, glucagon, viomycin, thyrotropin-releasing hormone (TRH), leucine-enkephalin, methionine-enkephalin, substance P, a parathyroid hormone (PTH) fragment (e.g., teriparatide (PTH(1-34)), PTH(1-31), or PTH(2-34)), carfilzomib, icatibant, cilengitide, a prostaglandin F2α receptor modulator (e.g., PDC31), and pharmaceutically acceptable salts thereof. It is particularly preferred that the peptide drug is selected from semaglutide, liraglutide, teriparatide (PTH(1-34)), octreotide, leuprolide, and pharmaceutically acceptable salts thereof.

As noted above, the peptide drug may be a GLP-1 analog. The GLP-1 analog may be, in particular, a variant of human Glucagon-Like Peptide-1, preferably a variant of GLP-1(7-37). The amino acid sequence of GLP-1(7-37) is HAEGTFTSDVSSYLEGQAAKEFIAWLVKGRG. The aforementioned "variant" of human Glucagon-Like Peptide-1 or of GLP-1(7-37) preferably refers to a compound differing by one or more amino acids from human Glucagon-Like Peptide-1 or from GLP-1(7-37), respectively, wherein such difference is caused by the addition, substitution or deletion of at least one amino acid (e.g., 1 to 10 amino acids) or any combination of such addition(s), substitution(s) and/or deletion(s). A GLP-1 analog may, e.g., exhibit at least 60% (preferably at least 65%, more preferably at least 70%, even more preferably at least 80%, and most preferably at least 90%) sequence identity to GLP-1(7-37) over the entire length of said GLP-1(7-37). As an example of a method for the determination of sequence identity between a GLP-1 analog and GLP-1(7-37), the two peptides [Aib8]GLP-1(7-37) and GLP-1(7-37) are aligned. [Aib8]GLP-1(7-37) differs from GLP-1(7-37) in that the alanine in position 8 is replaced by α-methylalanine (Aib, i.e. 2-aminoisobutyric acid). The sequence identity of [Aib8]GLP-1(7-37) relative to GLP-1(7-37) is given by the number of aligned identical residues minus the number of different residues divided by the total number of residues in GLP-1(7-37). Accordingly, in this example the sequence identity is (31-1)/31. The C-terminus of the GLP-1 analog (including any one of the specific GLP-1 analogs described herein) may also be in the form of an amide. Moreover, the GLP-1 analog may be, e.g., GLP-1(7-37) or GLP-1(7-36)amide. The GLP-1 analog may also be, e.g., exendin-4, the amino acid sequence of which is HGEGTFITSDLSKQMEEEAVRLFIEW-LKNGGPSSGAPPPS. The GLP-1 analog may further be a modified form of naturally occuring GLP-1 (particularly human GLP-1), which differs from the GLP-1 peptide in that it comprises one substituent which is covalently attached to the peptide. Said substituent may comprise a fatty acid (e.g., a C16, C18 or C20 fatty acid) or a fatty diacid (e.g., a C16, C18 or C20 fatty diacid). Said substituent may also comprise a group of the following formula:

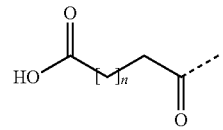

wherein n is at least 13 (e.g., 13, 14, 15, 16, 17, 18 or 19; preferably 13 to 17; more preferably 13, 15 or 17). Said substituent may also comprise one or more 8-amino-3,6-dioxaoctanoic acid (OEG) groups, such as two OEG groups. In particular, said substituent may be selected from [2-(2-{2-[2-(2-{2-[(S)-4-carboxy-4-(17-carboxyheptadecanoylamino)butyrylamino]ethoxy}ethoxy)acetylamino]ethoxy}ethoxy)acetyl] and [2-(2-{2-[2-(2-{2-[(S)-4-carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl]. The GLP-1 analog may also be selected from one or more of the GLP-1 agonists disclosed in WO 93/19175, WO 96/29342, WO 98/08871, WO 99/43707, WO 99/43706, WO 99/43341, WO 99/43708, WO 2005/027978, WO 2005/058954, WO 2005/058958, WO 2006/005667, WO 2006/037810, WO 2006/037811, WO 2006/097537, WO 2006/097538, WO 2008/023050, WO 2009/030738, WO 2009/030771 and WO 2009/030774.

Moreover, as mentioned above, the peptide drug may also be glatiramer (particularly glatiramer acetate). The invention thus also relates to glatiramer or a pharmaceutically acceptable salt thereof, particularly glatiramer acetate, for use as a medicament (e.g., for use in the treatment or prevention of multiple sclerosis), wherein said glatiramer or the pharmaceutically acceptable salt thereof (e.g., glatiramer acetate) is to be administered orally in combination with: a pharmaceutically acceptable copper salt/complex and/or a pharmaceutically acceptable zinc salt/complex and/or a pharmaceutically acceptable iron salt/complex; and a pharmaceutically acceptable complexing agent.

The peptide drug to be used in accordance with the invention can also be a mixture of two or more different peptide drugs, including any of the above-mentioned specific peptide drugs.

The pharmaceutically acceptable "copper salt/complex" to be used in accordance with the present invention refers to a pharmaceutically acceptable salt of copper or a pharmaceutically acceptable complex (e.g., a chelate complex) of copper. Likewise, the pharmaceutically acceptable "zinc salt/complex" to be employed in accordance with the invention refers to a pharmaceutically acceptable salt of zinc or a pharmaceutically acceptable complex (e.g., a chelate complex) of zinc. Moreover, the pharmaceutically acceptable "iron salt/complex" to be employed in accordance with the invention refers to a pharmaceutically acceptable salt of iron or a pharmaceutically acceptable complex (e.g., a chelate complex) of iron. While the expression "pharmaceutically acceptable" is omitted when referring to the copper salt/complex, the zinc salt/complex or the iron salt/complex in the following, it will be understood that the corresponding salts or complexes to be used in accordance with the invention are pharmaceutically acceptable.

The copper salt/complex is preferably a copper(I) salt/complex or a copper(II) salt/complex. Exemplary copper(I) salts/complexes include copper(I) chloride (CuCl) and copper(I) acetate (CuCH$_3$CO$_2$). Exemplary copper(II) salts/complexes include copper sulfate (CuSO$_4$), copper carbonate (CuCO$_3$), a copper(II) amino acid complex (such as, e.g., copper(II) lysine complex, or copper(II) glycinate), copper (II) EDTA complex, copper(II) chitosan complex, copper(II) citrate, copper(II) gluconate, copper(II) lactate, copper lactate gluconate (also referred to as "EZ-Copper"), and copper (II) orotate. Further exemplary copper(II) salts/complexes include copper chlorophyllin complex (particularly E141, natural green, or natural green 3) and copper(II) tartrate. The copper salt/complex is more preferably a copper(II) salt/complex. The use of a copper(II) salt/complex is advantageous since it provides better aqueous solubility and better oxidation state stability than a copper(I) salt/complex. Even more preferably, the copper salt/complex to be used in accordance with the invention is a copper(II) salt/complex selected from copper sulfate (CuSO$_4$), copper carbonate (CuCO$_3$), a copper(II) amino acid complex (preferably a Cu$^{2+}$ L-amino acid complex), copper(II) lysine complex (preferably Cu$^{2+}$ L-lysine complex), copper(II) citrate, copper(II) gluconate (preferably copper(II) D-gluconate), and copper(II) orotate.

The zinc salt/complex is preferably a zinc(II) salt/complex. Exemplary zinc(II) salts/complexes include zinc sulfate, zinc chloride, zinc acetate, zinc oxide, zinc ascorbate, zinc caprylate, zinc gluconate, zinc stearate, zinc carbonate, zinc orotate, a zinc amino acid complex (preferably a zinc L-amino acid complex), zinc glycinate, zinc arginate, zinc picolinate, zinc pidolate, zinc carnosine, zinc undecanoate, zinc undecylenate (e.g., zinc 10-undecenoate), zinc methionine, zinc lactate, and zinc lactate gluconate (also referred to as "EZ-Zinc"). The zinc salt/complex is more preferably selected from zinc sulfate, zinc chloride, zinc acetate, zinc oxide, zinc ascorbate, zinc caprylate, zinc gluconate, zinc stearate, zinc carbonate, zinc orotate, and a zinc amino acid complex (particularly a zinc L-amino acid complex).

The iron salt/complex is preferably an iron(II) salt/complex or an iron(III) salt/complex. Exemplary iron(II) salts/complexes include iron(II) gluconate, iron(II) orotate, iron(II) tartrate, iron(II) fumarate, iron(II) sulfate, iron(II) lactate, iron(II) lactate gluconate (also referred to as "EZ-Ferrous"), iron(II) acetate, iron(II) carbonate, iron(II) citrate, iron(II) oxide, iron(II) hydroxide, iron(II) ascorbate, and an iron(II) amino acid complex (e.g., an iron(II) chelate of any one of the 20 standard proteinogenic α-amino acids; preferably ferrous bis-glycinate or ferrous bis-glycinate hydrochloride). Exemplary iron(III) salts/complexes include iron(III) chloride (FeCl$_3$), iron(III) sulfate, iron(III) oxide, iron(III)carbonate, iron(III) acetate, iron(III) phosphate, iron (III) hydroxide, iron(III) tartrate, iron(III) lactate, iron(III) glycinate, iron(III) EDTA (i.e., Fe(III)-EDTA complex (1:1)), iron(III) ascorbate, and ammonium iron(III) citrate (i.e., ammonium ferric citrate). The iron salt/complex is more preferably an iron(II) salt/complex. The use of iron(II) salts/complexes is advantageous as they are more water-soluble than iron(III) salts/complexes. Even more preferably, the iron salt/complex to be used in accordance with the invention is an iron(II) salt/complex selected from iron(II) gluconate, iron(II) orotate, iron(II) tartrate, iron(II) fumarate, iron(II) sulfate, iron(II) lactate, iron(II) lactate gluconate, iron(II) acetate, iron(II) carbonate, iron(II) citrate, iron(II) oxide, iron(II) hydroxide, iron(II) ascorbate, and an iron(II) amino acid complex (e.g., an iron(II) chelate of any one of the 20 standard proteinogenic α-amino acids; preferably ferrous bis-glycinate or ferrous bis-glycinate hydrochloride). Yet even more preferably, the iron salt/complex is an organic iron(II) salt/complex, particularly an iron(II) salt/complex selected from iron(II) gluconate, iron (II) orotate, iron(II) tartrate, iron(II) fumarate, iron(II) lactate, iron(II) lactate gluconate, iron(II) citrate, iron(II) ascorbate, and an iron(II) amino acid complex, still more preferably iron(II) orotate, iron(II) gluconate, or iron(II) glycinate (i.e., ferrous bis-glycinate).

While either a copper salt/complex, a zinc salt/complex, or an iron salt/complex (or a combination of a copper salt/complex and a zinc salt/complex, or a combination of a copper salt/complex and an iron salt/complex, or a combination of a zinc salt/complex and an iron salt/complex, or a combination of copper salt/complex, a zinc salt/complex and an iron salt/complex) can be employed in accordance with the present invention, the use of a copper salt/complex has been found to provide a greater improvement of oral bioavailability of the corresponding peptide drug than the use of a zinc salt/complex or an iron salt/complex. The use of a copper salt/complex is thus preferred over the use of a zinc salt/complex and over the use of an iron salt/complex. At the same time, the use of a zinc salt/complex is advantageous since zinc can safely be administered to humans at even higher doses than copper. It is hence preferred that a copper salt/complex and/or a zinc salt/complex is used, and it is particularly preferred that a copper salt/complex is used.

The pharmaceutically acceptable complexing agent to be used in accordance with the present invention is not particularly limited and may be any complexing agent (particularly a complexing agent for monovalent, divalent and/or trivalent metal cations) that is acceptable for oral administration. The use of complexing agents is advantageous as they can improve the solubility of zinc, copper and iron salts/complexes at a broad pH range usually present in the gastrointestinal tract. It is preferred that the pharmaceutically acceptable complexing agent is selected from mannitol (e.g., high purity mannitol which is free of reducing byproducts), sorbitol, saccharose, sucrose, trehalose, calcium phosphate (e.g., basic calcium phosphate, calcium hydrogen phosphate, dicalcium phosphate hydrate, disodium phosphate dihydrate), an amino acid (e.g., any one of the 20 standard proteinogenic α-amino acids), EDTA, EGTA, citrate, a complexing peptide (such as GHK, i.e., glycyl-histidyl-lysine peptide), polyacrylic acid, a polyacrylic acid derivative, a carbomer, a carbomer derivative, sodium alginate, a silicate (e.g., kaolin), hydroxypropyl methylcellulose (HPMC), methylcellulose (MC), glycerol, sodium dodecyl sulfate, calcium sulfate, calcium carbonate, and pharmaceutically acceptable salts of any of the aforementioned agents. Analogs and derivatives of the above-mentioned agents can also be used. Mixtures of two or more complexing agents, including any of the above-described complexing agents, can likewise be used. If the complexing agent is mannitol, which as a pure substance is a non-reducing sugar but typically contains reducing byproducts from its industrial manufacture, it is preferred to use mannitol in pure form, particularly to use high purity mannitol which is free of reducing byproducts. Accordingly, if the complexing agent is mannitol, it is preferred to use mannitol that is free of reducing byproducts. More preferably, the pharmaceutically acceptable complexing agent is selected from sorbitol, saccharose, sucrose, trehalose, calcium phosphate (e.g., basic calcium phosphate, calcium hydrogen phosphate, dicalcium phosphate hydrate, disodium phosphate dihydrate), an amino acid (e.g., any one of the 20 standard proteinogenic α-amino acids), a complexing peptide (such as GHK, i.e., glycyl-histidyl-lysine peptide), polyacrylic acid, a carbomer, sodium alginate, a silicate (e.g., kaolin), hydroxypropyl methylcellulose (HPMC), methylcellulose (MC), glycerol, sodium dodecyl sulfate, calcium sulfate, calcium carbonate, and pharmaceutically acceptable salts thereof. Suitable pharmaceutically acceptable complexing agents are further described in: Fernane F et al., Interactions between calcium phosphate and heavy metal ions in aqueous solution, MATEC Web of Conferences, Vol. 5, EDP Sciences, 2013; U.S. Pat. No. 8,193,291; and Giertsen E et al. *Caries Res.* 1989;23(4):278-83. The pharmaceutically acceptable complexing agent may also be a polyol (such as, e.g., mannitol, sorbitol, or glycerol), a sugar-based surfactant (such as, e.g., any one of the surfactants referred to in Ferlin N et al., *J Surfact Deterg.* 2012; 15(3):259-264), a carboxylate (such as, e.g., citrate, tartrate, gluconate, oxalate, malate or salcaprozate), a phosphate (such as, e.g., sodium tri-phosphate or tetra potassium pyrophosphate), a sulfate (such as, e.g., sodium dodecyl sulfate), an amine (such as, e.g., ethylene diamine, chlorophyll, or choline), an amino acid or a complexing peptide (such as, e.g., lysine, glycine, histidine, or any of the amino acids or peptides referred to in Kober P A et al., *Journal of Biological Chemistry.* 1912; 13(1):1-13 or in Trzaskowski B et al., *J Biol Inorg Chem.* 2008; 13(1):133-7), an aminopolycarboxylic acid (such as, e.g., EDTA, EGTA, pentetic acid or diethylenetriaminepentaacetic acid (DTPA), or humic acid), a polymeric complexing agent (such as, e.g., HPMC (which may also be in the form of an HPMC capsule, such as QualiV, VCaps or VCaps plus), pullulan (which may also be in the form of a Pullulan capsule), a polycarboxylate, a carbomer or Carbopol, chitosan, alginate, povidone, polyvinylalcohol (PVA), or any complexing agent or polymer referred to in U.S. Pat. No. 8,193,291), a cyclodextrine, or any mixture of two or more of the aforementioned agents.

In each one of the first to eighth aspects described herein, it is particularly preferred that the peptide drug, the copper salt/complex and/or the zinc salt/complex and/or the iron salt/complex, and the pharmaceutically acceptable complexing agent are orally administered in combination with an absorption enhancer (also referred to herein as a "gastrointestinal absorption enhancer"). The administration of an absorption enhancer improves or facilitates the mucosal absorption of the peptide drug in the gastrointestinal tract and is advantageous particularly if the peptide drug is a large molecule, e.g., a peptide drug having a molecular weight of about 1 kDa or more.

The absorption enhancer is preferably selected to be compatible with the copper salt/complex and/or the zinc salt/complex and/or the iron salt/complex that is/are used, which can readily be tested, e.g., as described in Example 1. In particular, it is preferred that the absorption enhancer is soluble in an aqueous medium at a pH of about 7 in the presence of the copper salt/complex and/or the zinc salt/complex and/or the iron salt/complex that is/are used. The occurrence of precipitation or flocculation, as observed for certain combinations of a specific zinc salt/complex or a specific iron salt/complex with a specific absorption enhancer in an aqueous medium (see Examples 1 and 4), is undesirable but does not rule out the use of a corresponding formulation in accordance with the invention.

The absorption enhancer may be, e.g., a zwitter-ionic absorption enhancer, a cationic absorption enhancer, an anionic absorption enhancer (e.g., an anionic absorption enhancer comprising one or more sulfonic acid groups ($—SO_3H$)), or a non-ionic absorption enhancer, particularly a zwitter-ionic absorption enhancer or a non-ionic absorption enhancer. It is preferred that the absorption enhancer is selected from $C_{8-20}$ alkanoyl carnitine (preferably lauroyl carnitine, myristoyl carnitine or palmitoyl carnitine; e.g., lauroyl carnitine chloride, myristoyl carnitine chloride or palmitoyl carnitine chloride), salicylic acid (preferably a salicylate, e.g., sodium salicylate), a salicylic acid derivative (such as, e.g., 3-methoxysalicylic acid, 5-methoxysalicylic acid, or homovanillic acid, a $C_{8-20}$ alkanoic acid (preferably a $C_{8-20}$ alkanoate, more preferably a caprate, a caprylate, a myristate, a palmitate, or a stearate, such as, e.g., sodium caprate, sodium caprylate, sodium myristate, sodium palmitate, or sodium stearate), citric acid (preferably a citrate, e.g., sodium citrate), tartaric acid (preferably a tartrate), a fatty acid acylated amino acid (e.g., any of the fatty acid acylated amino acids described in US 2014/0056953 A1 which is incorporated herein by reference, including, without being limited thereto, sodium lauroyl alaninate, N-dodecanoyl-L-alanine, sodium lauroyl asparaginate, N-dodecanoyl-L-asparagine, sodium lauroyl aspartic acid, N-dodecanoyl-L-aspartic acid, sodium lauroyl cysteinate, N-dodecanoyl-L-cysteine, sodium lauroyl glutamic acid, N-dodecanoyl-L-glutamic acid, sodium lauroyl glutaminate, N-dodecanoyl-L-glutamine, sodium lauroyl glycinate, N-dodecanoyl-L-glycine, sodium lauroyl histidinate, N-dodecanoyl-L-histidine, sodium lauroyl isoleucinate, N-dodecanoyl-L-isoleucine, sodium lauroyl leucinate, N-dodecanoyl-L-leucine, sodium lauroyl methioninate, N-dodecanoyl-L-methionine, sodium lauroyl phenylalaninate, N-dodecanoyl-L-phenylalanine, sodium lauroyl prolinate, N-dodecanoyl-L-proline, sodium lauroyl serinate, N-dodecanoyl-L-serine, sodium lauroyl threoninate, N-dodecanoyl-L-threonine, sodium lauroyl tryptophanate, N-dodecanoyl-L-tryptophane, sodium lauroyl tyrosinate, N-dodecanoyl-L-tyrosine, sodium lauroyl valinate, N-dodecanoyl-L-valine, sodium lauroyl sarcosinate, N-dodecanoyl-L-sarcosine, sodium capric alaninate, N-decanoyl-L-alanine, sodium capric asparaginate, N-decanoyl-L-asparagine, sodium capric aspartic acid, N-decanoyl-L-aspartic acid, sodium capric cysteinate, N-decanoyl-L-cysteine, sodium capric glutamic acid, N-decanoyl-L-glutamic acid, sodium capric glutaminate, N-decanoyl-L-glutamine, sodium capric glycinate, N-decanoyl-L-glycine, sodium capric histidinate, N-decanoyl-L-histidine, sodium capric isoleucinate, N-decanoyl-L-isoleucine, sodium capric leucinate, N-decanoyl-L-leucine, sodium capric methioninate, N-decanoyl-L-methionine, sodium capric phenylalaninate, N-decanoyl-L-phenylalanine, sodium capric prolinate, N-decanoyl-L-proline, sodium capric serinate, N-decanoyl-L-serine, sodium capric threoninate, N-decanoyl-L-threonine, sodium capric tryptophanate, N-decanoyl-L-tryptophane, sodium capric tyrosinate, N-decanoyl-L-tyrosine, sodium capric valinate, N-decanoyl-L-valine, sodium capric sarcosinate, N-decanoyl-L-sarcosine, sodium oleoyl sarcosinate, sodium N-decylleucine, sodium stearoyl glutamate (e.g., Amisoft HS-11 P), sodium myristoyl glutamate (e.g., Amisoft MS-11), sodium lauroyl glutamate (e.g., Amisoft LS-11), sodium cocoyl glutamate (e.g., Amisoft CS-11), sodium cocoyl glycinate (e.g., Amilite GCS-11), sodium N-decyl leucine, sodium cocoyl glycine, sodium cocoyl glutamate, sodium lauroyl alaninate, N-dodecanoyl-L-alanine, sodium lauroyl asparaginate, N-dodecanoyl-L-asparagine, sodium lauroyl aspartic acid, N-dodecanoyl-L-aspartic acid, sodium lauroyl cysteinate, N-dodecanoyl-L-cysteine, sodium lauroyl glutamic acid, N-dodecanoyl-L-glutamic acid, sodium lauroyl glutaminate, N-dodecanoyl-L-glutamine, sodium lauroyl glycinate, N-dodecanoyl-L-glycine, sodium lauroyl histidinate, N-dodecanoyl-L-histidine, sodium lauroyl isoleucinate, N-dodecanoyl-L-isoleucine, sodium lauroyl leucinate, N-dodecanoyl-L-leucine, sodium lauroyl methioninate, N-dodecanoyl-L-methionine, sodium lauroyl phenylalaninate, N-dodecanoyl-L-phenylalanine, sodium lauroyl prolinate, N-dodecanoyl-L-proline, sodium lauroyl serinate, N-dodecanoyl-L-serine, sodium lauroyl threoninate, N-dodecanoyl-L-threonine, sodium lauroyl tryptophanate, N-dodecanoyl-L-tryptophane, sodium lauroyl tyrosinate, N-dodecanoyl-L-tyrosine, sodium lauroyl valinate, N-dodecanoyl-L-valine, N-dodecanoyl-L-sarcosine, sodium capric alaninate, N-decanoyl-L-alanine, sodium capric asparaginate, N-decanoyl-L-asparagine, sodium capric aspartic acid, N-decanoyl-L-aspartic acid, Sodium capric cysteinate, N-decanoyl-L-cysteine, sodium capric glutamic acid, N-decanoyl-L-glutamic acid, sodium capric glutaminate, N-decanoyl-L-glutamine, sodium capric glycinate, N-decanoyl-L-glycine, sodium capric histidinate, N-decanoyl-L-histidine, sodium capric isoleucinate, N-decanoyl-L-isoleucine, sodium capric leucinate, N-decanoyl-L-leucine, sodium capric methioninate, N-decanoyl-L-methionine, sodium capric phenylalaninate, N-decanoyl-L-phenylalanine, sodium capric prolinate, N-decanoyl-L-proline, sodium capric serinate, N-decanoyl-L-serine, sodium capric threoninate, N-decanoyl-L-threonine, sodium capric tryptophanate, N-decanoyl-L-tryptophane, sodium capric tyrosinate, N-decanoyl-L-tyrosine, sodium capric valinate, N-decanoyl-L-valine, N-decanoyl-L-sarcosine, sodium oleoyl sarcosinate, and pharmaceutically acceptable salts of any of the aforementioned compounds; or, e.g., $C_{8-20}$ alkanoyl sarcosinate (e.g., a lauroyl sarcosinate, such as sodium lauroyl sarcosinate) or one of the 20 standard proteinogenic α-amino acids that is acylated with a $C_{8-20}$ alkanoic acid), an alkylsaccharide (e.g., a $C_{1-20}$ alkylsaccharide, such as, e.g., $C_{8-10}$ alkylpolysaccharide like Multitrope™ 1620-LQ-(MV); or, e.g., n-octyl-beta-D-glucopyranoside, n-dodecyl-beta-D-maltoside, n-tetradecyl-beta-D-maltoside, tridecyl-beta-D-maltoside, sucrose laurate, sucrose myristate, sucrose palmitate, sucrose cocoate, sucrose mono-dodecanoate, sucrose mono-tridecanoate, sucrose mono-tetradecanoate, a coco-glucoside, or any of the alkylsaccharides described in U.S. Pat. No. 5,661,130 or in WO 2012/112319 which are herein incorporated by reference), a cyclodextrine (e.g., α-cyclodextrin, β-cyclodextrin, γ-cyclodextrin, methyl-β-cyclodextrin, hydroxypropyl β-cyclodextrin, or sulfobutylether β-cyclodextrin), N-[8-(2-hydroxybenzoyl)amino]caprylic acid (preferably a N-[8-(2-hydroxybenzoyl)amino]caprylate, more preferably sodium N-[8-(2-hydroxybenzoyl)amino]caprylate, also referred to as "SNAC"), a N-[8-(2-hydroxybenzoyl)amino] caprylate derivative (preferably a sodium N-[8-(2-hydroxybenzoyl)amino]caprylate derivative), a thiomer (also referred to as a thiolated polymer; may be synthesized, e.g., by immobilization of sulfhydryl bearing ligands on a polymeric backbone of well-established polymers such as, e.g., polyacrylic acid, carboxymethylcellulose or chitosan; exemplary thiomers include the thiomers that are described in Laffleur F et al., *Future Med Chem.* 2012, 4(17):2205-16 (doi: 10.4155/fmc.12.165) which is incorporated herein by reference), a mucoadhesive polymer having a vitamin B partial structure (e.g., any of the mucoadhesive polymers described in U.S. Pat. No. 8,980,238 B2 which is incorporated herein by reference; including, in particular, any of the polymeric compounds as defined in any one of claims 1 to 3 of U.S. Pat. No. 8,980,238 B2), a calcium chelating compound (e.g., ethylenediaminetetraacetic acid (EDTA), ethylene glycol tetraacetic acid (EGTA), sodium citrate, or polyacrylic acid), cremophor EL (also referred to as "Kolliphor EL"; CAS no. 61791-12-6), chitosan, N,N,N-trimethyl chitosan, benzalkonium chloride, bestatin, cetylpyridinium chloride, cetyltrimethylammonium bromide, a $C_{2-20}$ alkanol (e.g., ethanol, decanol, lauryl alcohol, myristyl alcohol, or palmityl alcohol), a $C_{8-20}$ alkenol (e.g., oleyl alcohol), a $C_{8-20}$ alkenoic acid (e.g., oleic acid), dextran sulfate, diethyleneglycol monoethyl ether (transcutol), 1-dodecylazacyclo-heptan-2-one (Azone®), caprylocaproyl polyoxylglycerides (such as, e.g., caprylocaproyl polyoxyl-8 glycerides; available, e.g., as Labrasol® or ACCONON® MC8-2), ethyl caprylate, glyceryl monolaurate, lysophosphatidylcholine, menthol, a $C_{8-20}$ alkylamine, a $C_{8-20}$ alkenylamine (e.g., oleylamine), phosphatidylcholine, a poloxamer, polyethylene glycol monolaurate, polyoxyethylene, polypropylene glycol monolaurate, a polysorbate (e.g., polysorbate 20 or polysorbate 80), cholic acid (preferably a cholate, e.g., sodium chlolate), a deoxycholate (e.g., sodium deoxycholate), sodium glycocholate, sodium glycodeoxycholate, sodium lauryl sulfate (SDS), sodium decyl sulfate, sodium octyl sulfate, sodium laureth sulfate, N-lauryl sarcosinate, decyltrimethyl ammonium bromide, benzyldimethyl dodecyl ammonium chloride, myristyltrimethyl ammonium chloride, dodecyl pyridinium chloride, decyldimethyl ammonio propane sulfonate, myristyldimethyl ammonio propane sulfonate, palmityldimethyl ammonio propane sulfonate, ChemBetaine CAS, ChemBetaine Oleyl, Nonylphenoxypolyoxyethylene, polyoxyethylene sorbitan monolaurate, polyoxyethylene sorbitan monopalmitate, sorbitan monooleate, Triton X-100, hexanoic acid, heptanoic acid, methyl laurate, isopropyl myristate, isopropyl palmitate, methyl palmitate, diethyl sebaccate, sodium oleate, urea, lauryl amine, caprolactam, methyl pyrrolidone, octyl pyrrolidone, methyl piperazine, phenyl piperazine, Carbopol 934P, glyccyrhetinic acid, bromelain, pinene oxide, limonene, cineole, octyl dodecanol, fenchone, menthone, trimethoxy propylene methyl benzene, a cell-penetrating peptide (e.g., KLAKLAK, polyarginine (particularly octaarginine), penetratin (particularly L-penetratin), a penetratin analog (particularly PenetraMax; see, e.g., El-Sayed Khafagy et al., *Eur J Pharm Biopharm.* 2013; 85(3 Pt A):736-43), HIV-1 Tat, transportan, or any of the cell-penetrating peptides referred to in US 2012/0065124), macrogol-15-hydroxystearate (e.g., Solutol HS 15), CriticalSorb (see., e.g., Ilium L et al. *J Control Release.* 2012;162(1):194-200), a taurocholate (e.g., sodium taurocholate), a taurodeoxycholate (e.g., sodium taurodeoxycholate), a sulfoxide (e.g., a ($C_{1-10}$ alkyl)-($C_{1-10}$ alkyl)-sulfoxide, such as, e.g., decyl methyl sulfoxide, or dimethyl sulfoxide), cyclopentadecalactone, 8-(N-2-hydroxy-5-chloro-benzoyl)-amino-caprylic acid (also referred to as "5-CNAC"), N-(10-[2-hydroxybenzoyl]amino)decanoic acid (also referred to as "SNAD"), dodecyl-2-N,N-dimethylamino propionate (also referred to as "DDAIP"), D-α-tocopheryl polyethylene glycol-1000 succinate (also referred to as "TPGS"), and pharmaceutically acceptable salts of the aforementioned compounds. Mixtures of two or more absorption enhancers, including any of the above-described absorption enhancers, can also be used. Moreover, any of the chemical permeation enhancers described in Whitehead K et al. *Pharm Res.* 2008 Jun;25(6):1412-9 (particularly any one of those described in Table I of this reference), any one of the modified amino acids disclosed in U.S. Pat. No. 5,866,536 (particularly any one of compounds I to CXXIII, as disclosed in U.S. Pat. No. 5,866,536 which is incorporated herein by reference, or a pharmaceutically acceptable salt or solvate thereof, such as a disodium salt, an ethanol solvate, or a hydrate of any one of these compounds), any one of the modified amino acids disclosed in U.S. Pat. No. 5,773,647 (particularly any one of compounds 1 to 193, as disclosed in U.S. Pat. No. 5,773,647 which is incorporated herein by reference, or a pharmaceutically acceptable salt or solvate thereof, such as a disodium salt, an ethanol solvate, or a hydrate of any one of these compounds), any of the nanoparticles described in WO 2011/133198, any of the polymer preparations described in US 2015/174076 and/or a hydrogel (e.g., as described in Torres-Lugo M et al. *Biotechnol Prog.* 2002;18(3):612-6) can likewise be used as absorption enhancer. Moreover, a complex lipoidal dispersion (e.g., a combination of an insoluble surfactant or oil with a soluble surfactant, and optionally with water or a co-solvent) can also be used as absorption enhancer; corresponding exemplary absorption enhancers include, in particular, mixed micelles, reversed micelles, a self emulsifying system (e.g., SEDDS, SMEDDS, or SNEDDS), a lipid dispersion, a course emulsion, or solid lipid nanoparticles (SLNs). A particularly preferred absorption enhancer is N-[8-(2-hydroxybenzoyl) amino]caprylate or a pharmaceutically acceptable salt thereof, in particular sodium N-[8-(2-hydroxybenzoyl) amino]caprylate (SNAC). In accordance with the present invention, it is furthermore particularly preferred to use an organic copper salt/complex and/or an organic zinc salt/complex and/or an organic iron salt/complex (particularly copper(II) orotate and/or zinc orotate and/or iron(II) orotate), and to use sodium N-[8-(2-hydroxybenzoyl)amino] caprylate as an absorption enhancer.

The absorption enhancer may also be a compound of the following formula (I):

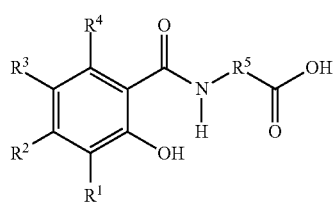

wherein:

$R^1$, $R^2$, $R^3$ and $R^4$ are each independently selected from hydrogen, —OH, —$NR^6R^7$, halogen (e.g., —F, —Cl, —Br or —I), $C_{1-4}$ alkyl or $C_{1-4}$ alkoxy;

$R^5$ is a substituted or unsubstituted $C_{2-16}$ alkylene, substituted or unsubstituted $C_{2-16}$ alkenylene, substituted or unsubstituted $C_{1-12}$ alkyl(arylene) [e.g., substituted or unsubstituted $C_{1-12}$ alkyl(phenylene)], or substituted or unsubstituted aryl($C_{1-12}$ alkylene) [e.g., substituted or unsubstituted phenyl($C_{1-12}$ alkylene)]; and $R^6$ and $R^7$ are each independently hydrogen, oxygen, —OH or $C_{1-4}$ alkyl;

or a pharmaceutically acceptable salt or solvate thereof, particularly a disodium salt, an alcohol solvate (e.g., a methanol solvate, an ethanol solvate, a propanol solvate, or a propylene glycol solvate, or any such solvate of the disodium salt; particularly an ethanol solvate or an ethanol solvate of the disodium salt), or a hydrate thereof (e.g., a monohydrate of the disodium salt). The above-mentioned "substituted" groups comprised in formula (I) are preferably substituted with one or more (e.g., one, two, or three) substituent groups independently selected from halogen (e.g., —F, —Cl, —Br or —I), —OH, $C_{1-4}$ alkyl or $C_{1-4}$ alkoxy. Such compounds and methods for their preparation are described, e.g., in WO 00/59863 which is incorporated herein by reference. Accordingly, the absorption enhancer may also be a "delivery agent" as described in WO 00/59863. Preferred examples of the compounds of formula (I) include N-(5-chlorosalicyloyl)-8-aminocaprylic acid, N-(10-[2-hydroxybenzoyl]amino)decanoic acid, N-(8-[2-hydroxybenzoyl]amino)caprylic acid, a monosodium or disodium salt of any one of the aforementioned compounds, an ethanol solvate of the sodium salt (e.g., monosodium or disodium salt) of any one of the aforementioned compounds, a monohydrate of the sodium salt (e.g., monosodium or disodium salt) of any one of the aforementioned compounds, and any combination thereof. A particularly preferred compound of formula (I) is the disodium salt of N-(5-chlorosalicyloyl)-8-aminocaprylic acid or the monohydrate thereof.

Furthermore, the pharmaceutical formulations provided in accordance with the present invention can also be administered in combination with a pharmaceutically acceptable reducing agent; it is, however, preferred that they are not administered in combination with any of the pharmaceutically acceptable reducing agents specified further below in this paragraph. Thus, it is preferred that the peptide drug, the copper salt/complex and/or the zinc salt/complex and/or the iron salt/complex, and the pharmaceutically acceptable complexing agent are to be administered in accordance with any one of the first to eighth aspect described herein, with the proviso that the administration in combination with a pharmaceutically acceptable reducing agent is excluded, said reducing agent being selected from ascorbic acid (or an ascorbate, e.g., sodium ascorbate), reduced glutathione (GSH), cysteine, uric acid, a reducing sugar (e.g., a reducing monosaccharide, such as glucose, glyceraldehyde or galactose, or a reducing disaccharide, such as lactose or maltose), mannitol, α-tocopherol, vitamin A, α-lipoic acid, dihydro-α-lipoic acid (DHLA), a thiol-bearing compound, a thiomer (also referred to as a "thiolated polymer"; e.g., a thiomer synthesized by immobilization of sulfhydryl bearing ligands on a polymeric backbone, e.g., a polymeric backbone of polyacrylic acid, carboxymethylcellulose or chitosan; exemplary thiomers include the thiomers that are described in Laffleur F et al., *Future Med Chem.* 2012, 4(17):2205-16 (doi: 10.4155/fmc.12.165) which is incorporated herein by reference), pharmaceutically acceptable salts of any of the aforementioned reducing agents, and mixtures thereof. Accordingly, it is preferred that the peptide drug, the copper salt/complex and/or the zinc salt/complex and/or the iron salt/complex, and the pharmaceutically acceptable complexing agent are to be administered orally, but not in combination with a pharmaceutically acceptable reducing agent selected from ascorbic acid, reduced glutathione (GSH), cysteine, uric acid, a reducing sugar, mannitol, α-tocopherol, vitamin A, α-lipoic acid, dihydro-α-lipoic acid (DHLA), a thiol-bearing compound, a thiomer, pharmaceutically acceptable salts of any of the aforementioned reducing agents, and mixtures thereof. This is particularly preferred if a copper salt/complex and/or a zinc salt/complex is used. Likewise, it is preferred that the pharmaceutical composition of the sixth aspect of the invention and the pharmaceutical dosage form of the seventh aspect of the invention do not comprise (i.e., are free of) a pharmaceutically acceptable reducing agent selected from ascorbic acid, reduced glutathione (GSH), cysteine, uric acid, a reducing sugar, mannitol, α-tocopherol, vitamin A, α-lipoic acid, dihydro-α-Lipoic acid (DHLA), a thiol-bearing compound, a thiomer, pharmaceutically acceptable salts of any of the aforementioned reducing agents, and mixtures thereof. This is particularly preferred if the pharmaceutical composition or the pharmaceutical dosage form comprises a copper salt/complex and/or a zinc salt/complex. In a preferred embodiment, the aforementioned reducing sugar (which is not to be administered in combination or which is not comprised in the pharmaceutical composition or the pharmaceutical dosage form) is a reducing monosaccharide or a reducing disaccharide, whereas other reducing sugars, such as a reducing oligosaccharide (comprising at least three monosaccharide units) or a reducing polysaccharide (such as a glucose polymer, e.g., starch, a starch derivative (e.g., glucose syrup, maltodextrin, dextrin, dextrose, or dextran), or cellulose (e.g., microcrystalline cellulose (MCC), such as Avicel®)), may also be administered in combination with the peptide drug, the copper salt/complex and/or the zinc salt/complex and/or the iron salt/complex, and the pharmaceutically acceptable complexing agent, or may be present in the pharmaceutical composition or the pharmaceutical dosage form provided herein. In a further preferred embodiment, the aforementioned reducing sugar (which is not to be administered in combination or which is not comprised in the pharmaceutical composition or the pharmaceutical dosage form) is selected from glucose, glyceraldehyde, galactose, lactose and maltose, whereas other reducing sugars, such as fructose, ribose, xylose, sorbose, cellobiose, a reducing oligosaccharide (comprising at least three monosaccharide units) or a reducing polysaccharide (such as a glucose polymer, e.g., starch, a starch derivative (e.g., glucose syrup, maltodextrin, dextrin, dextrose, or dextran), or cellulose (e.g., microcrystalline cellulose (MCC), such as Avicel®)), may also be administered in combination with the peptide drug, the copper salt/complex and/or the zinc salt/complex and/or the iron salt/complex, and the pharmaceutically acceptable complexing agent, or may be present in the pharmaceutical composition or the pharmaceutical dosage form provided herein.

In accordance with the present invention, it is furthermore envisaged that one or more pharmaceutically acceptable reducing agents other than the ones that are preferably excluded (as described in the above paragraph) may be administered in combination with the peptide drug, the copper salt/complex and/or the zinc salt/complex and/or the iron salt/complex, and the pharmaceutically acceptable complexing agent, or may be comprised in the pharmaceutical composition or the pharmaceutical dosage form according to the sixth or seventh aspect of the invention. Such other pharmaceutically acceptable reducing agents may be selected from, e.g., N-acetylcysteine, histidine, glycine, arginine, gelatin, oxalic acid, phytic acid, a tannin, propyl gallate, butylated hydroxy toluene (BHT), butylated hydroxy anisole (BHA), sodium metabisulfite (also referred to as "sodium pyrosulfite", $Na_2S_2O_5$), povidone (i.e., polyvinylpyrrolidone, PVP; also referred to as "polyvidone"; see, e.g., Washio I et al. *Advanced Materials*. 2006;18(13): 1745-9; examples of povidone preparations include, in particular, Kollidon® 30, Kollidon® CL, Kollidon® 90 F, or Kollidon® VA 64), crospovidone, an aldehyde (e.g., an aldehyde ($C_{1-5}$ alkyl)-CHO, such as formaldehyde or acetaldehyde, or furfuraldehyde), a dialdehyde (e.g., glyoxal), a phenolic compound (i.e., a compound comprising at least one phenyl ring substituted with at least one hydroxy group; exemplary phenolic compounds include, in particular, phenol, a polyphenol, salicylic acid, or a salicylic acid derivative; see, e.g., Iwasaki Y et al. *Toxicol In Vitro*. 2011;25(7): 1320-7), diphosphate (E 450), disodiumdiphosphate, trisodiumdiphosphate, tetrasodiumdiphosphate, tetrapotassiumdiphosphate, dicalciumdiphosphate, calciumdihydrogendiphophate, phosphate, dipotassium hydrogen phosphate (see, e.g., Zhang X et al. *J Colloid Interface Sci*. 2013;409: 1-7), calcium phosphate (e.g., calcium hydrogen phosphate, such as Emcompress®), and pharmaceutically acceptable salts of any of the aforementioned agents. Analogs and derivatives of the aforementioned reducing agents can likewise be used. Mixtures of two or more of any of these reducing agents can also be used. Moreover, such other pharmaceutically acceptable reducing agents may also include a reducing sugar selected from fructose, ribose, xylose, sorbose, cellobiose, a reducing oligosaccharide (comprising at least three monosaccharide units), and a reducing polysaccharide (such as a glucose polymer, e.g., starch, a starch derivative (e.g., glucose syrup, maltodextrin, dextrin, dextrose, or dextran), or cellulose (e.g., microcrystalline cellulose (MCC), such as Avicel®)).

As described above, amino acids such as cysteine, histidine, glycine or arginine can be used as pharmaceutically acceptable reducing agent, but also protein and peptide mixtures such as gelatin (see, e.g., Sae-leaw T et al. *J Food Sci Technol*. 2015:1-12; Gimenez B et al. *Food Chemistry*. 2009;114(3):976-83) can be used. Gelatin is unusually high in the non-essential amino acid glycine. Gelatin will be hydrolyzed in the gastrointestinal tract after oral intake. Gelatin can be of different sources and mixtures thereof, such as from cattle, pigs, chicken and fish. In particular, a pharmaceutical grade gelatin may be used as pharmaceutically acceptable reducing agent. The pharmaceutical grade gelatin may be in the form of, e.g., a gelatin capsule, such as a soft or hard capsule.

Moreover, as described above, aldehydes such as, e.g., formaldehyde, acetaldehyde, furfuraldehyde, or other aldehydes can also be used as pharmaceutically acceptable reducing agent. Reactive amounts of aldehydes are common in microcrystalline cellulose (MCC), starch, pre-gelatinized starch, crospovidone, hydroxypropyl cellulose, polyethylene glycol, polysorbate and lactose. Polyethylene glycol (PEG) 200, 400, and 600 exhibit significantly high levels of formaldehyde (65.2-107.0 ppm) and acetaldehyde (2.7-12.5 ppm). Polyethylene glycol (PEG) used in coating materials, such as Opadry II White, leads to the generation of formaldehyde (Wang G et al. *Pharm Dev Technol*. 2008;13(5): 393-9). Headspace gas chromatography is the most commonly used method to determine trace amounts of reducing aldehydes in pharmaceutical excipients (Li Z et al. *J Chromatogr A*. 2006;1104(1-2):1-10). Reducing aldehydes that can be used in accordance with the present invention are further described, e.g., in: Nassar M N et al. *Pharm Dev Technol*. 2004;9(2):189-95; and Wu Y et al. *AAPS PharmSciTech*. 2011;12(4):1248-63. Moreover, pharmaceutically acceptable dialdehydes, such as glyoxal, can also be used as the pharmaceutically acceptable reducing agent, as mentioned above. Glyoxal can be found in hydroxyethylcellulose and in hydroxypropylmethylcellulose (HPMC).

However, the invention also relates to the possibility that an administration of the peptide drug, the copper salt/complex and/or the zinc salt/complex and/or the iron salt/complex, and the pharmaceutically acceptable complexing agent in combination with any pharmaceutically acceptable reducing agent is excluded (i.e., that an administration in combination with a further compound which is a pharmaceutically acceptable reducing agent and which is different from the peptide drug, the copper salt/complex (if present), the zinc salt/complex (if present), the iron salt/complex (if present) and the complexing agent, is excluded). The invention likewise relates to the possibility that the pharmaceutical composition of the sixth aspect or the pharmaceutical dosage form of the seventh aspect does not comprise (i.e., is free of) any further compound which is a pharmaceutically acceptable reducing agent.

The (i) peptide drug, (ii) the copper salt/complex and/or the zinc salt/complex and/or the iron salt/complex, (iii) the pharmaceutically acceptable complexing agent, and (iv) the optionally used absorption enhancer may be administered simultaneously/concomitantly or sequentially. In the case of sequential administration, the copper salt/complex and/or the zinc salt/complex and/or the iron salt/complex as well as the pharmaceutically acceptable complexing agent may be administered first, followed by the administration of the peptide drug and the optionally used absorption enhancer (e.g., at least about 5 min after the first administration, preferably about 5 min to about 3 hours after the first administration, more preferably about 10 min to about 1 hour after the first administration). Also, the copper salt/complex and/or the zinc salt/complex and/or the iron salt/complex as well as the pharmaceutically acceptable complexing agent and the optionally used absorption enhancer may be administered first, followed by the administration of the peptide drug (e.g., at least about 5 min after the first administration, preferably about 5 min to about 3 hours after the first administration, more preferably about 10 min to about 1 hour after the first administration). In the case of simultaneous administration, the (i) peptide drug, (ii) the copper salt/complex and/or the zinc salt/complex and/or the iron salt/complex, (iii) the pharmaceutically acceptable complexing agent, and (iv) the optionally used absorption enhancer may be administered in the same pharmaceutical composition, or in two or more different/separate pharmaceutical compositions, or in two or more different/separate compartments of the same pharmaceutical dosage form, as also described further below.

The peptide drug, the copper salt/complex and/or the zinc salt/complex and/or the iron salt/complex, the pharmaceutically acceptable complexing agent, and the optionally used absorption enhancer can be administered, e.g., in the form of a pharmaceutical composition as described in the sixth aspect of the invention.

It is preferred that the pharmaceutical composition according to the sixth aspect of the invention is a solid composition or a liquid substantially water-free composition. Such compositions are particularly advantageous as they provide an improved shelf-stability and thus enable prolonged storage periods. The liquid substantially water-free composition is preferably a liquid composition that contains less than about 5% (v/v) of water, more preferably less than about 3% (v/v) of water, even more preferably less than about 1% (v/v) of water, even more preferably less than about 0.5% (v/v) of water, yet even more preferably less than about 0.1% (v/v) of water, and is still more preferably free of water. Most preferably, the pharmaceutical composition of the sixth aspect is a solid composition (e.g., a tablet or a powder). It is furthermore preferred that the solid composition is substantially water-free, e.g., contains less than about 5% (w/w) of water, preferably less than about 3% (w/w) of water, more preferably less than about 1% (w/w) of water, even more preferably less than about 0.5% (w/w) of water, yet even more preferably less than about 0.1% (w/w) of water, and is still more preferably free of water.

It is also possible, although not preferred, that the pharmaceutical composition according to the sixth aspect of the invention is an aqueous liquid composition (e.g., an aqueous solution). In this case, the composition should preferably be prepared shortly before administration to the subject/patient, and prolonged storage periods should be avoided.

The pharmaceutical composition according to the sixth aspect of the present invention may also be an oral composition of a GLP-1 peptide, which composition is prepared as described in WO 2013/139694 but further comprises (i) a copper salt/complex and/or a zinc salt/complex and/or an iron salt/complex, and (ii) a pharmaceutically acceptable complexing agent. Preferably, a salt of N-(8-(2-hydroxybenzoyl)amino)caprylic acid, the copper salt/complex and/or the zinc salt/complex and/or the iron salt/complex, and the complexing agent are present in the first type of granules and the GLP-1 peptide is present in the second type of granules. Alternatively, a salt of N-(8-(2-hydroxybenzoyl)amino) caprylic acid as well as the copper salt/complex and/or the zinc salt/complex and/or the iron salt/complex are present in the first type of granules, the GLP-1 peptide is present in the second type of granules, and the complexing agent is present in both the first and the second type of granules. As a further alternative, a salt of N-(8-(2-hydroxybenzoyl)amino) caprylic acid is present in the first type of granules and the copper salt/complex and/or the zinc salt/complex and/or the iron salt/complex as well as the GLP-1 peptide and the complexing agent are present in the second type of granules.

Moreover, the pharmaceutical composition according to the sixth aspect may also be in the form of a mucoadhesive device, such as a mucoadhesive patch, e.g., as described in US 2015/0174076 or in US 2003/0017195.

Furthermore, it is particularly preferred that the pharmaceutical composition according to the sixth aspect is a pharmaceutical dosage form in which the peptide drug is physically separated from the pharmaceutically acceptable copper salt/complex (if present) and the pharmaceutically acceptable zinc salt/complex (if present) and the pharmaceutically acceptable iron salt/complex (if present), as described in the seventh aspect of the invention.

The pharmaceutical dosage form according to the seventh aspect of the invention preferably comprises at least two separate compartments which are physically separated from one another (e.g., through a physical separation layer). Accordingly, it is preferred that the pharmaceutical dosage form comprises a physical separation layer between (i) the peptide drug and (ii) the copper salt/complex (if present) and the zinc salt/complex (if present) and the iron salt/complex (if present). The peptide drug is present only in a first compartment, and the copper salt/complex and/or the zinc salt/complex and/or the iron salt/complex is/are present only in a second compartment of the pharmaceutical dosage form. The pharmaceutically acceptable complexing agent may be present either in the first compartment, or in the second compartment, or in both the first and the second compartment, or in a third compartment of the pharmaceutical dosage form. In one preferred embodiment according to the seventh aspect, the invention thus provides a pharmaceutical dosage form (e.g., a double capsule) comprising: a peptide drug having a molecular weight of equal to or less than 5 kDa, which is present in a first compartment of the pharmaceutical dosage form; a pharmaceutically acceptable copper salt/complex and/or a pharmaceutically acceptable zinc salt/complex and/or a pharmaceutically acceptable iron salt/complex, which is/are present in a second compartment of the pharmaceutical dosage form; and a pharmaceutically acceptable complexing agent, which is present in the first compartment and/or the second compartment of the pharmaceutical dosage form. In a further preferred embodiment of the seventh aspect, the invention provides a pharmaceutical dosage form (e.g., a multi-particulate dosage form)

comprising: a peptide drug having a molecular weight of equal to or less than 5 kDa, which is present in a first compartment of the pharmaceutical dosage form; a pharmaceutically acceptable complexing agent, which is present in a second compartment of the pharmaceutical dosage form; and a pharmaceutically acceptable copper salt/complex and/or a pharmaceutically acceptable zinc salt/complex and/or a pharmaceutically acceptable iron salt/complex, which is/are present in a third compartment of the pharmaceutical dosage form. It is particularly preferred that the pharmaceutical dosage form of the seventh aspect is a capsule inside a capsule (also referred to as a double capsule) or a multiparticulate dosage form. In the case of a double capsule, it is preferred that the bigger outer capsule (the content of which will be released first) contains the copper salt/complex and/or the zinc salt/complex and/or the iron salt/complex as well as the pharmaceutically acceptable complexing agent, and that the smaller inner capsule (the content of which will be released later) contains the peptide drug. The dosage form may also be a release-modified dosage form, such as a dosage form (e.g., a capsule, multiparticulate or tablet) having an enteric coating or a dosage form (e.g., a capsule, multiparticulate or tablet) coated with Eudragit L30D55 or with Eudragit FS30D or an acid resistant capsule such as HPMCP capsules (commercially known as AR Caps®).

The pharmaceutical composition according to the sixth aspect and also the pharmaceutical dosage form according to the seventh aspect of the invention preferably comprise the copper salt/complex in an amount equal of about 0.1 mg to about 20 mg $Cu^+$ or $Cu^{2+}$ per dosage unit (more preferably about 0.1 mg to about 10 mg per dosage unit, even more preferably about 0.1 mg to about 5 mg per dosage unit), and/or the zinc salt/complex in an amount equal of about 0.1 mg to about 50 mg $Zn^{2+}$ (e.g., about 1 mg, about 3 mg, about 5 mg, about 10 mg, about 20 mg, or about 50 mg) per dosage unit, and/or the iron salt/complex in an amount of about 1 mg to about 100 mg $Fe^{2+}$ or $Fe^{3+}$ per dosage unit (more preferably about 1 mg to about 50 mg per dosage unit). They further comprise the pharmaceutically acceptable complexing agent in an amount of preferably about 1 mg to about 1000 mg per dosage unit, more preferably about 50 mg to about 500 mg per dosage unit. Moreover, if they comprise an absorption enhancer, the absorption enhancer is preferably included in an amount of about 10 mg to about 1000 mg per dosage unit, more preferably about 50 mg to about 500 mg per dosage unit.

It is furthermore preferred that the constitution of the pharmaceutical composition is such that, if the composition were added to ten milliliters of 5% HCl solution, it would neutralize the acid and generate a pH of higher than about 6. In addition, it is also preferred that the constitution of the pharmaceutical composition is such that, if the composition were added to ten milliliters of aqueous solution, it would generate a pH of higher than about 6 and lower than about pH 9.

The pharmaceutically acceptable salts referred to herein may be formed, e.g., by protonation of an atom carrying an electron lone pair which is susceptible to protonation, such as an amino group, with an inorganic or organic acid, or as a salt of a carboxylic acid group with a physiologically acceptable cation as they are well-known in the art. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Exemplary acid addition salts comprise, for example: mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, glycolate, nicotinate, benzoate, salicylate, ascorbate, or pamoate (embonate) salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthalenesulfonate (napsylate), 3-phenylsulfonate, or camphorsulfonate salts; and acidic amino acid salts such as aspartate or glutamate salts. It is to be understood that the term "pharmaceutically acceptable salt" also embraces pharmaceutically acceptable salts of the corresponding compound in any solvated form.

The peptide drug, the copper salt/complex and/or the zinc salt/complex and/or the iron salt/complex, the pharmaceutically acceptable complexing agent, and the optionally used absorption enhancer (which are collectively referred to as the "compounds to be administered" in the following) may each be administered as compounds per se or may be formulated as medicaments, e.g., in the form of a pharmaceutical composition according to the sixth aspect and/or a pharmaceutical dosage form according to the seventh aspect of the invention. The medicaments/pharmaceutical compositions, including also the pharmaceutical composition according to the sixth aspect and the pharmaceutical dosage form according to the seventh aspect, may optionally comprise one or more pharmaceutically acceptable excipients, such as carriers, diluents, fillers, disintegrants, lubricating agents, binders, colorants, pigments, stabilizers, preservatives, antioxidants, and/or solubility enhancers. In particular, they may comprise one or more additives selected from vitamin E, histidine, microcrystalline cellulose (MCC), mannitol, starch, sorbitol and/or lactose. The pharmaceutical compositions can be formulated by techniques known to the person skilled in the art, such as the techniques published in Remington's Pharmaceutical Sciences, $20^{th}$ Edition.

As noted above, the pharmaceutical compositions may comprise one or more solubility enhancers, such as, e.g., poly(ethylene glycol), including poly(ethylene glycol) having a molecular weight in the range of about 200 to about 5,000 Da, ethylene glycol, propylene glycol, non-ionic surfactants, tyloxapol, polysorbate 20, polysorbate 80, macrogol-15-hydroxystearate, phospholipids, lecithin, dimyristoyl phosphatidylcholine, dipalmitoyl phosphatidylcholine, distearoyl phosphatidylcholine, cyclodextrins, α-cyclodextrin, β-cyclodextrin, γ-cyclodextrin, hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, sulfobutylether-β-cyclodextrin, sulfobutylether-γ-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, carboxyalkyl thioethers, hydroxypropyl methylcellulose, hydroxypropylcellulose, polyvinylpyrrolidone, vinyl acetate copolymers, vinyl pyrrolidone, sodium lauryl sulfate, dioctyl sodium sulfosuccinate, or any combination thereof. Preferably, the one or more solubility enhancers include at least one non-ionic surfactant, more preferably at least one non-ionic surfactant having a hydrophilic-lipophilic balance (HLB) of greater than 10 (i.e., HLB>10). The pharmaceutical compositions may also comprise at least one non-ionic surfactant having an HLB>10 and at least one non-ionic surfactant having an HLB<10.

It is thus preferred that the pharmaceutical compositions comprise at least one non-ionic surfactant. In particular, the pharmaceutical compositions may comprise a substance (preferably a detergent) that is capable of adsorbing at surfaces and/or interfaces (such as liquid to air, liquid to liquid, liquid to container, or liquid to any solid) and that has no charged groups in its hydrophilic group(s) (sometimes referred to as "heads"). The non-ionic surfactant may be a detergent and may, in particular, be selected from ethoxylated castor oil, a polyglycolyzed glyceride, an acetylated monoglyceride, a sorbitan-fatty-acid-ester, a polysorbate (such as, e.g., polysorbate-20, polysorbate-40, polysorbate-60, polysorbate-80, super-refined polysorbate 20, super-refined polysorbate 40, super-refined polysorbate 60, or super-refined polysorbate 80; including any of the corresponding Tween products, e.g., from the supplier Croda), a poloxamer (such as, e.g., poloxamer 188 or poloxamer 407), a polyoxyethylene sorbitan fatty acid ester, a polyoxyethylene derivative (such as, e.g., an alkylated and/or alkoxylated polyoxyethylene derivative; particularly a Tween product like, e.g., Tween-20 or Tween-80), a block copolymer such as, e.g., a polyethyleneoxide/polypropyleneoxide block copolymer (e.g., Pluronics/Tetronics, TritonX-100 and/or Synperonic PE/L44PEL), an ethoxylated sorbitan alkanoate (such as, e.g., Tween-20, Tween-40, Tween-80, or Brij-35), diglycerol laurate, diglycerol caprate, diglycerol caprylate, diglycerol monocaprylate, polyglycerol laurate, polyglycerol caprate, polyglycerol caprylate, or any combination thereof. Further examples of non-ionic surfactants that may be used as solubility enhancers in accordance with the invention include, but are not limited to: (1.) reaction products of a natural or hydrogenated castor oil and ethylene oxide (where the natural or hydrogenated castor oil may be reacted with ethyleneoxide in a molar ratio of from about 1:35 to about 1:60, with optional removal of the PEG component from the products; various such surfactants are commercially available, e.g., the CREMOPHOR series from BASF Corp. (Mt. Olive, N.J.), such as CREMOPHOR RH 40 which is PEG40 hydrogenated castor oil and an HLB of about 14-16); (2.) polyoxyethylene fatty acid esters, including in particular polyoxyethylene stearic acid esters (such as the MYRJ series from Uniqema, e.g., MYRJ 53 having a m.p. of about 47° C.; particular compounds in the MYRJ series are, e.g., MYRJ 53 having a m.p. of about 47° C. and PEG-40-stearate which is available, e.g., as MYRJ 52); (3.) sorbitan derivatives, including in particular the TWEEN series from Uniqema (e.g., TWEEN 60, Tween 20, Tween 80, or Tween 40); (4.) polyoxyethylene-polyoxypropylene co-polymers and/or block co-polymers and/or poloxamers (e.g., Pluronic P127 or Pluronic F68 from BASF or Synperonic PE/L from Croda); (5.) polyoxyethylenealkylethers (such as, e.g., polyoxyethylene glycol ethers of C12-C18 alcohols, like, e.g., polyoxyl 10- or 20-cetylether or polyoxyl 23-laurylether, or 20-oleylether, or polyoxyl 10-,20- or 100-stearylether, e.g., as commercially available as the BRI series from Uniqema; particularly useful products from the BRIJ series include BRIJ 58, BRIJ 76, BRIJ 78, BRIJ 35 (or polyoxyl 23-laurylether), or BRIJ 98 (or polyoxyl 20 oleyl ether); these products may have a m.p. between about 32° C. and about 43° C.); (6.) water-soluble tocopheryl PEG succinic acid esters (e.g., as available from Eastman Chemical Co., with a m.p. of about 36° C., such as, e.g, TPGS, particularly vitamin E-TPGS); (7.) PEG sterol ethers (such as, e.g., SOLULAN C24 (Choleth-24 and Cetheth-24) from Chemron (Paso Robles, Calif.); similar products which may also be used are those which are known and commercially available as NIKKOL BPS-30 (poly ethoxylated 30 phytosterol) and NIKKOL BPSH-25 (poly ethoxylated 25 phytostanol) from Nikko Chemicals); (8.) polyglycerol fatty acid esters, e.g., having 4 to 10 glycerol units, such as 4, 6 or 10 glycerol units (e.g., particularly suitable are deca-/hexa-/tetraglycerylmonostearate, e.g., DECAGLYN, HEXAGLYN or TETRAGLYN from Nikko Chemicals); (9.) alkylene polyolether or ester (e.g., lauroyl macrogol-32 glycerides and/or stearoylmacrogol-32 glycerides, such as GELUCIRE 44/14 and/or GELUCIRE 50/13); (10.) polyoxyethylenemonoesters of a saturated $C_{10}$-$C_{22}$ (e.g., $C_{18}$) hydroxy fatty acid (which may optionally be substituted), such as, e.g., 12-hydroxystearic acid PEG ester, e.g., of PEG 600, 900 or 660 (e.g., SOLUTOL HS 15 from BASF (Ludwigshafen, Germany); or a substance comprsining (or consisting of) about 70% polyethoxylated 12-hydroxystearate by weight and about 30% by weight unesterified polyethylene glycol component, having a hydrogenation value of 90 to 110, a saponine cation value of 53 to 63, an acid number of maximum 1, and a maximum water content of 0.5% by weight); (11.) polyoxyethylene-polyoxypropylene-alkyl ethers (such as, e.g., polyoxyethylene-polyoxypropylene ethers of $C_{12}$-$C_{18}$ alcohols, e.g., polyoxyethylen-20-polyoxypropylene-4-cetylether, which is commercially available as NIKKOL PBC 34 from Nikko Chemicals); or (12.) polyethoxylated distearates (e.g., as commercially available under the trade names ATLAS G 1821 from Uniqema and/or NIKKOCDS-6000P from Nikko Chemicals).

The pharmaceutical compositions are preferably formulated as dosage forms for oral administration, particularly peroral administration. Accordingly, it is most preferred that the compounds to be administered or the above described pharmaceutical compositions, including also the pharmaceutical composition according to the sixth aspect and the pharmaceutical dosage form according to the seventh aspect, are administered to a subject/patient orally, particularly perorally. It is thus preferred that the peptide drug, the copper salt/complex and/or the zinc salt/complex and/or the iron salt/complex, the pharmaceutically acceptable complexing agent, and the optionally used absorption enhancer are all to be administered orally.

Dosage forms for oral administration include, e.g., tablets (e.g., coated or uncoated tablets), capsules (e.g., HPMC capsules or HPMCP capsules), a capsule inside a capsule, mini patch systems inside a capsule, lozenges, troches, ovules, solutions, emulsions, suspensions, syrups, elixirs, powders and granules for reconstitution, dispersible powders and granules, medicated gums, chewing tablets, effervescent tablets, and multiparticulate dosage forms.

The tablets may contain excipients such as non-reducing sugars, microcrystalline cellulose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose and acacia. Additionally, lubricating agents such as magnesium stearate, stearic acid, glyceryl behenate and talc may be included. Solid compositions of a similar type may also be employed as fillers in hard capsules. Preferred excipients in this regard include non-reducing sugars, starch, a cellulose, or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Typically, a physician will determine the actual dosage which will be most suitable for an individual subject. The specific dose level and frequency of dosage for any particular individual subject may be varied and will depend upon a variety of factors including the activity of the specific peptide drug employed, the metabolic stability and length of action of that compound, the age, body weight, general health, sex, diet, mode and time of administration, rate of excretion, drug combination, the severity of the particular condition, and the individual subject undergoing therapy. The precise dose will ultimately be at the discretion of the attendant physician or veterinarian.

The subject or patient to be treated, such as the subject in need of treatment or prevention, may be an animal (e.g., a non-human animal), a vertebrate animal, a mammal, a rodent (e.g., a guinea pig, a hamster, a rat, a mouse), a murine (e.g., a mouse), a canine (e.g., a dog), a feline (e.g., a cat), a porcine (e.g., a pig), an equine (e.g., a horse), a primate, a simian (e.g., a monkey or ape), a monkey (e.g., a marmoset, a baboon), an ape (e.g., a gorilla, chimpanzee, orang-utan, gibbon), or a human. In the context of this invention, it is also envisaged that animals are to be treated which are economically or agronomically important. Non-limiting examples of agronomically important animals are sheep, cattle and pigs, while, for example, cats and dogs may be considered as economically important animals. Preferably, the subject/patient is a mammal; more preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orang-utan, a gibbon, a sheep, cattle, or a pig); most preferably, the subject/patient is a human.

The term "treatment" of a disorder or disease as used herein is well known in the art. "Treatment" of a disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

The "treatment" of a disorder or disease may, for example, lead to a halt in the progression of the disorder or disease (e.g., no deterioration of symptoms) or a delay in the progression of the disorder or disease (in case the halt in progression is of a transient nature only). The "treatment" of a disorder or disease may also lead to a partial response (e.g., amelioration of symptoms) or complete response (e.g., disappearance of symptoms) of the subject/patient suffering from the disorder or disease. Accordingly, the "treatment" of a disorder or disease may also refer to an amelioration of the disorder or disease, which may, e.g., lead to a halt in the progression of the disorder or disease or a delay in the progression of the disorder or disease. Such a partial or complete response may be followed by a relapse. It is to be understood that a subject/patient may experience a broad range of responses to a treatment (such as the exemplary responses as described herein above). The treatment of a disorder or disease may, inter alia, comprise curative treatment (preferably leading to a complete response and eventually to healing of the disorder or disease) and palliative treatment (including symptomatic relief).

The term "prevention" of a disorder or disease as used herein is also well known in the art. For example, a patient/subject suspected of being prone to suffer from a disorder or disease may particularly benefit from a prevention of the disorder or disease. The subject/patient may have a susceptibility or predisposition for a disorder or disease, including but not limited to hereditary predisposition. Such a predisposition can be determined by standard methods or assays, using, e.g., genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of a peptide drug according to the invention before any clinical and/or pathological symptoms are diagnosed or determined or can be diagnosed or determined by the attending physician.

The term "peptide", as in the expression "peptide drug", refers to a polymer of two or more amino acids linked via amide bonds that are formed between an amino group of one amino acid and a carboxyl group of another amino acid. The amino acids comprised in the peptide, which are also referred to as amino acid residues, may be selected from the 20 standard proteinogenic α-amino acids (i.e., Ala, Arg, Asn, Asp, Cys, Glu, Gln, Gly, His, Ile, Leu, Lys, Met, Phe, Pro, Ser, Thr, Trp, Tyr, and Val) but also from non-proteinogenic and/or non-standard α-amino acids (such as, e.g., ornithine, citrulline, homolysine, pyrrolysine, or 4-hydroxyproline) as well as β-amino acids (e.g., β-alanine), γ-amino acids and δ-amino acids. Preferably, the amino acid residues comprised in the peptide are selected from α-amino acids, more preferably from the 20 standard proteinogenic α-amino acids (which can be present as the L-isomer or the D-isomer, and are preferably all present as the L-isomer). The peptide may be unmodified or may be modified, e.g., at its N-terminus, at its C-terminus and/or at a functional group in the side chain of any of its amino acid residues (particularly at the side chain functional group of one or more Lys, His, Ser, Thr, Tyr, Cys, Asp, Glu, and/or Arg residues). Such modifications may include, e.g., the attachment of any of the protecting groups described for the corresponding functional groups in: Wuts P G & Greene T W, Greene's protective groups in organic synthesis, John Wiley & Sons, 2006. Such modifications may also include the covalent attachment of one or more polyethylene glycol (PEG) chains (forming a PEGylated peptide), the glycosylation and/or the acylation with one or more fatty acids (e.g., one or more $C_{5-30}$ alkanoic or alkenoic acids; forming a fatty acid acylated peptide). The amino acid residues comprised in the peptide may, e.g., be present as a linear molecular chain (forming a linear peptide) or may form one or more rings (corresponding to a cyclic peptide). The peptide may also form oligomers consisting of two or more identical or different molecules.

The term "amino acid" refers, in particular, to any one of the 20 standard proteinogenic α-amino acids (i.e., Ala, Arg, Asn, Asp, Cys, Glu, Gln, Gly, His, Ile, Leu, Lys, Met, Phe, Pro, Ser, Thr, Trp, Tyr, and Val) but also to non-proteinogenic and/or non-standard α-amino acids (such as, e.g., ornithine, citrulline, homolysine, pyrrolysine, or 4-hydroxyproline) as well as β-amino acids (e.g., β-alanine), γ-amino acids and/or δ-amino acids. Unless defined otherwise, an "amino acid" preferably refers to an α-amino acid, more preferably to any one of the 20 standard proteinogenic α-amino acids (which can be present as the L-isomer or the D-isomer, and are preferably present as the L-isomer).

As used herein, the term "complex" refers to a chelate complex (in which coordinate bonds are formed between a single central atom/ion and a polydentate ligand) or a coordination complex composed of monodentate ligands coordinating a single central atom/ion.

As used herein, the term "reducing sugar" refers to a sugar that has an open-chain form with an aldehyde group or a free hemiacetal group and can thus act as a reducing agent. A reducing sugar may be, e.g., a reducing monosaccharide (e.g., glucose, glyceraldehyde, galactose, fructose, ribose, xylose, or sorbose), a reducing disaccharide (e.g., lactose (such as spray-dried lactose, α-lactose, β-lactose, Tabletose®, various grades of Pharmatose®, Microtose®, or Fast-FloC®), maltose, or cellobiose), or a reducing polysaccharide (e.g., a glucose polymer, such as starch, a starch derivative (like, e.g., glucose syrup, maltodextrin, dextrin, dextrose, or dextran), or cellulose (e.g., microcrystalline cellulose (MCC), such as Avicel®)).

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, if a component of a composition is indicated to be "optional", the invention specifically relates to both possibilities, i.e., that the corresponding component is present (contained in the composition) or that the corresponding component is absent from the composition.

As used herein, the term "about" preferably refers to ±10% of the indicated numerical value, more preferably to ±5% of the indicated numerical value, and in particular to the exact numerical value indicated. For example, the expression "about 100" preferably refers to the range of 90 to 110, in particular the range of 95 to 105, and more preferably refers to the specific value of 100. If the term "about" is used in connection with the endpoints of a range, it preferably refers to the range from the lower endpoint −10% of its indicated numerical value to the upper endpoint +10% of its indicated numerical value, in particular to the range from of the lower endpoint −5% to the upper endpoint +5%, and more preferably to the range defined by the exact numerical values of the lower endpoint and the upper endpoint. Thus, the expression "about 10 to about 20" preferably refers to the range of 9 to 22, in particular 9.5 to 21, and more preferably 10 to 20. If the term "about" is used in connection with the endpoint of an open-ended range, it preferably refers to the corresponding range starting from the lower endpoint −10% or from the upper endpoint +10%, in particular to the range starting from the lower endpoint −5% or from the upper endpoint +5%, and more preferably to the open-ended range defined by the exact numerical value of the corresponding endpoint. For example, the expression "at least about 10%" preferably refers to at least 9%, particularly at least 9.5%, and more preferably at least 10%.

Furthermore, it is to be understood that the present invention specifically relates to each and every combination of features and embodiments described herein, including any combination of general and/or preferred features/embodiments. In particular, the invention specifically relates to all combinations of preferred features described herein.

In this specification, a number of documents including patent applications and scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The present invention particularly relates to the following items:

1. A peptide drug having a molecular weight of equal to or less than 5 kDa for use as a medicament, wherein said peptide drug is to be administered orally in combination with: a pharmaceutically acceptable copper salt/complex and/or a pharmaceutically acceptable zinc salt/complex and/or a pharmaceutically acceptable iron salt/complex; and
   a pharmaceutically acceptable complexing agent.
2. A pharmaceutically acceptable copper salt/complex for use in therapy, wherein said copper salt/complex is to be administered orally in combination with:
   a peptide drug having a molecular weight of equal to or less than 5 kDa; and
   a pharmaceutically acceptable complexing agent.
3. A pharmaceutically acceptable zinc salt/complex for use in therapy, wherein said zinc salt/complex is to be administered orally in combination with:
   a peptide drug having a molecular weight of equal to or less than 5 kDa; and
   a pharmaceutically acceptable complexing agent.
4. A pharmaceutically acceptable iron salt/complex for use in therapy, wherein said iron salt/complex is to be administered orally in combination with:
   a peptide drug having a molecular weight of equal to or less than 5 kDa; and
   a pharmaceutically acceptable complexing agent.
5. A pharmaceutically acceptable complexing agent for use in therapy, wherein said complexing agent is to be administered orally in combination with:
   a peptide drug having a molecular weight of equal to or less than 5 kDa; and
   a pharmaceutically acceptable copper salt/complex and/or a pharmaceutically acceptable zinc salt/complex and/or a pharmaceutically acceptable iron salt/complex.
6. A pharmaceutical composition comprising:
   a peptide drug having a molecular weight of equal to or less than 5 kDa;
   a pharmaceutically acceptable copper salt/complex and/or a pharmaceutically acceptable zinc salt/complex and/or a pharmaceutically acceptable iron salt/complex; and
   a pharmaceutically acceptable complexing agent.
7. A pharmaceutical dosage form comprising:
   a peptide drug having a molecular weight of equal to or less than 5 kDa;

a pharmaceutically acceptable copper salt/complex and/or a pharmaceutically acceptable zinc salt/complex and/or a pharmaceutically acceptable iron salt/complex; and a pharmaceutically acceptable complexing agent;

wherein the peptide drug is physically separated from the pharmaceutically acceptable copper salt/complex, the pharmaceutically acceptable zinc salt/complex and the pharmaceutically acceptable iron salt/complex within the pharmaceutical dosage form.

8. The peptide drug for use according to item 1 or the copper salt/complex for use according to item 2 or the zinc salt/complex for use according to item 3 or the iron salt/complex for use according to item 4 or the complexing agent for use according to item 5 or the pharmaceutical composition of item 6 or the pharmaceutical dosage form of item 7, wherein the peptide drug has a molecular weight of about 500 Da to about 4 kDa.

9. The peptide drug for use according to item 1 or the copper salt/complex for use according to item 2 or the zinc salt/complex for use according to item 3 or the iron salt/complex for use according to item 4 or the complexing agent for use according to item 5 or the pharmaceutical composition of item 6 or the pharmaceutical dosage form of item 7, wherein the peptide drug has a molecular weight of about 1 kDa to about 3 kDa.

10. The peptide drug for use according to item 1 or the copper salt/complex for use according to item 2 or the zinc salt/complex for use according to item 3 or the iron salt/complex for use according to item 4 or the complexing agent for use according to item 5 or the pharmaceutical composition of item 6 or the pharmaceutical dosage form of item 7, wherein the peptide drug is selected from GLP-1, a GLP-1 analog, an acylated GLP-1 analog, a diacylated GLP-1 analog, a long-acting albumin-binding fatty acid-derivatized GLP-1 analog, a GLP-1 agonist, semaglutide, liraglutide, exenatide, exendin-4, lixisenatide, taspoglutide, langlenatide, GLP-1(7-37), GLP-1(7-36)NH$_2$, a dual agonist of the GLP-1 receptor and the glucagon receptor, oxyntomodulin, GLP-2, a GLP-2 agonist or analog, teduglutide, elsiglutide, amylin, an amylin analog, pramlintide, a somatostatin analog, octreotide, lanreotide, pasireotide, goserelin, buserelin, peptide YY, a peptide YY analog, glatiramer, leuprolide, desmopressin, a glycopeptide antibiotic, vancomycin, teicoplanin, telavancin, bleomycin, ramoplanin, decaplanin, bortezomib, cosyntropin, sermorelin, luteinizing-hormone-releasing hormone, calcitonin, calcitonin-salmon, pentagastrin, oxytocin, neseritide, enfuvirtide, eptifibatide, cyclosporine, glucagon, viomycin, thyrotropin-releasing hormone, leucine-enkephalin, methionine-enkephalin, substance P, a parathyroid hormone fragment, teriparatide, PTH(1-31), PTH(2-34), linaclotide, carfilzomib, icatibant, cilengitide, a prostaglandin F2α receptor modulator, PDC31, and pharmaceutically acceptable salts thereof.

11. The peptide drug for use according to any one of items 1 or 8 to 10, wherein said peptide drug is to be administered in combination with a pharmaceutically acceptable copper salt/complex.

12. The peptide drug for use according to any one of items 1 or 8 to 11 or the copper salt/complex for use according to any one of items 2 or 8 to 10 or the complexing agent for use according to any one of items 5 or 8 to 10 or the pharmaceutical composition of any one of items 6 or 8 to 10 or the pharmaceutical dosage form of any one of items 7 to 10, wherein said copper salt/complex is a copper(I) salt/complex or a copper(II) salt/complex.

13. The peptide drug for use according to item 12 or the copper salt/complex for use according to item 12 or the complexing agent for use according to item 12 or the pharmaceutical composition of item 12 or the pharmaceutical dosage form of item 12, wherein said copper salt/complex is a copper(II) salt/complex selected from copper sulfate, copper carbonate, a copper(II) amino acid complex, copper(II) lysine complex, copper(II) glycinate, copper(II) EDTA complex, copper(II) chitosan complex, copper(II) citrate, copper(II) gluconate, copper(II) lactate, copper lactate gluconate, and copper (II) orotate.

14. The peptide drug for use according to item 12 or the copper salt/complex for use according to item 12 or the complexing agent for use according to item 12 or the pharmaceutical composition of item 12 or the pharmaceutical dosage form of item 12, wherein said copper salt/complex is a copper(I) salt/complex selected from copper(I) chloride and copper(I) acetate.

15. The peptide drug for use according to any one of items 1 or 8 to 10, wherein said peptide drug is to be administered in combination with a pharmaceutically acceptable zinc salt/complex.

16. The peptide drug for use according to any one of items 1, 8 to 10 or 15 or the zinc salt/complex for use according to any one of items 3 or 8 to 10 or the complexing agent for use according to any one of items 5 or 8 to 10 or the pharmaceutical composition of any one of items 6 or 8 to 10 or the pharmaceutical dosage form of any one of items 7 to 10, wherein said zinc salt/complex is a zinc(II) salt/complex.

17. The peptide drug for use according to item 16 or the zinc salt/complex for use according to item 16 or the complexing agent for use according to item 16 or the pharmaceutical composition of item 16 or the pharmaceutical dosage form of item 16, wherein said zinc salt/complex is a zinc(II) salt/complex selected from zinc sulfate, zinc chloride, zinc acetate, zinc oxide, zinc ascorbate, zinc caprylate, zinc gluconate, zinc stearate, zinc carbonate, zinc orotate, a zinc amino acid complex, zinc glycinate, zinc arginate, zinc picolinate, zinc pidolate, zinc carnosine, zinc undecanoate, zinc undecylenate, zinc methionine, zinc lactate, and zinc lactate gluconate.

18. The peptide drug for use according to any one of items 1 or 8 to 10, wherein said peptide drug is to be administered in combination with a pharmaceutically acceptable iron salt/complex.

19. The peptide drug for use according to any one of items 1, 8 to 10 or 18 or the iron salt/complex for use according to any one of items 4 or 8 to 10 or the complexing agent for use according to any one of items 5 or 8 to 10 or the pharmaceutical composition of any one of items 6 or 8 to 10 or the pharmaceutical dosage form of any one of items 7 to 10, wherein said iron salt/complex is an iron(II) salt/complex or an iron(III) salt/complex.

20. The peptide drug for use according to item 19 or the iron salt/complex for use according to item 19 or the complexing agent for use according to item 19 or the pharmaceutical composition of item 19 or the pharmaceutical dosage form of item 19, wherein said iron salt/complex is an iron(II) salt/complex selected from iron(II) gluconate, iron(II) orotate, iron(II) tartrate, iron(II) fumarate, iron(II) sulfate, iron(II) lactate, iron (II) lactate gluconate, iron(II) acetate, iron(II) carbonate, iron(II) citrate, iron(II) oxide, iron(II) hydroxide, iron(II) ascorbate, an iron(II) amino acid complex, and ferrous bis-glycinate.

21. The peptide drug for use according to item 19 or the iron salt/complex for use according to item 19 or the complexing agent for use according to item 19 or the pharmaceutical composition of item 19 or the pharmaceutical dosage form of item 19, wherein said iron salt/complex is an iron(III) salt/complex selected from iron(III) chloride, iron(III) sulfate, iron(III) oxide, iron (III)carbonate, iron(III) acetate, iron(III) phosphate, iron(III) hydroxide, iron(III) tartrate, iron(III) lactate, iron(III) glycinate, iron(III) EDTA, iron(III) ascorbate, and ammonium iron(III) citrate.

22. The peptide drug for use according to any one of items 1 or 8 to 21 or the copper salt/complex for use according to any one of items 2, 8 to 10 or 12 to 14 or the zinc salt/complex for use according to any one of items 3, 8 to 10, 16 or 17 or the iron salt/complex for use according to any one of items 4, 8 to 10 or 19 to 21 or the complexing agent for use according to any one of items 5, 8 to 10, 12 to 14, 16, 17 or 19 to 21 or the pharmaceutical composition of any one of items 6, 8 to 10, 12 to 14, 16, 17 or 19 to 21 or the pharmaceutical dosage form of any one of items 7 to 10, 12 to 14, 16, 17 or 19 to 21, wherein said complexing agent is selected from mannitol, sorbitol, saccharose, sucrose, trehalose, calcium phosphate, basic calcium phosphate, calcium hydrogen phosphate, dicalcium phosphate hydrate, disodium phosphate dihydrate, an amino acid, EDTA, EGTA, citrate, a complexing peptide, glycyl-histidyl-lysine peptide, polyacrylic acid, a polyacrylic acid derivative, a carbomer, a carbomer derivative, sodium alginate, a silicate, kaolin, hydroxypropyl methylcellulose, methylcellulose, glycerol, sodium dodecyl sulfate, calcium sulfate, calcium carbonate, and pharmaceutically acceptable salts thereof.

23. The peptide drug for use according to any one of items 1 or 8 to 22 or the copper salt/complex for use according to any one of items 2, 8 to 10, 12 to 14 or 19 to 22 or the zinc salt/complex for use according to any one of items 3, 8 to 10, 16, 17 or 22 or the iron salt/complex for use according to any one of items 4, 8 to 10 or 19 to 22 or the complexing agent for use according to any one of items 5, 8 to 10, 12 to 14, 16, 17 or 19 to 22 or the pharmaceutical composition of any one of items 6, 8 to 10, 12 to 14, 16, 17 or 19 to 22 or the pharmaceutical dosage form of any one of items 7 to 10, 12 to 14, 16, 17 or 19 to 22, wherein said peptide drug or said copper salt/complex or said zinc salt/complex or said iron salt/complex or said complexing agent is to be administered orally in combination with an absorption enhancer, or wherein said pharmaceutical composition or said pharmaceutical dosage form further comprises an absorption enhancer.

24. The peptide drug for use according to item 23 or the copper salt/complex for use according to item 23 or the zinc salt/complex for use according to item 23 or the iron salt/complex for use according to item 23 or the complexing agent for use according to item 23 or the pharmaceutical composition of item 23 or the pharmaceutical dosage form of item 23, wherein said absorption enhancer is selected from $C_{8-20}$ alkanoyl carnitine, salicylic acid, a salicylic acid derivative, 3-methoxysalicylic acid, 5-methoxysalicylic acid, homovanillic acid, a $C_{8-20}$ alkanoic acid, citric acid, tartaric acid, a fatty acid acylated amino acid, a $C_{8-20}$ alkanoyl sarcosinate, an alkylsaccharide, a $C_{8-10}$ alkylpolysaccharide, n-octyl-beta-D-glucopyranoside, n-dodecyl-beta-D-maltoside, n-tetradecyl-beta-D-maltoside, tridecyl-beta-D-maltoside, sucrose laurate, sucrose myristate, sucrose palmitate, sucrose cocoate, sucrose mono-dodecanoate, sucrose mono-tridecanoate, sucrose mono-tetradecanoate, a coco-glucoside, a cyclodextrine, α-cyclodextrin, β-cyclodextrin, γ-cyclodextrin, methyl-β-cyclodextrin, hydroxypropyl β-cyclodextrin, sulfobutylether β-cyclodextrin, N-[8-(2-hydroxybenzoyDamino]caprylic acid, sodium N-[8-(2-hydroxybenzoyl)amino]caprylate, a sodium N-[8-(2-hydroxybenzoyl)amino]caprylate derivative, a thiomer, a mucoadhesive polymer having a vitamin B partial structure, a calcium chelating compound, ethylenediaminetetraacetic acid, ethylene glycol tetraacetic acid, polyacrylic acid, cremophor EL, chitosan, N,N,N-trimethyl chitosan, benzalkonium chloride, bestatin, cetylpyridinium chloride, cetyltrimethylammonium bromide, a $C_{2-20}$ alkanol, a $C_{8-20}$ alkenol, a $C_{8-20}$ alkenoic acid, dextran sulfate, diethyleneglycol monoethyl ether, 1-dodecylazacyclo-heptan-2-one, caprylocaproyl polyoxylglycerides, ethyl caprylate, glyceryl monolaurate, lysophosphatidylcholine, menthol, a $C_{8-20}$ alkylamine, a $C_{8-20}$ alkenylamine, phosphatidylcholine, a poloxamer, polyethylene glycol monolaurate, polyoxyethylene, polypropylene glycol monolaurate, a polysorbate, cholic acid, a deoxycholate, sodium glycocholate, sodium glycodeoxycholate, sodium lauryl sulfate, sodium decyl sulfate, sodium octyl sulfate, sodium laureth sulfate, N-lauryl sarcosinate, decyltrimethyl ammonium bromide, benzyldimethyl dodecyl ammonium chloride, myristyltrimethyl ammonium chloride, dodecyl pyridinium chloride, decyldimethyl ammonio propane sulfonate, myristyldimethyl ammonio propane sulfonate, palmityldimethyl ammonio propane sulfonate, ChemBetaine CAS, ChemBetaine Oleyl, Nonylphenoxypolyoxyethylene, polyoxyethylene sorbitan monolaurate, polyoxyethylene sorbitan monopalmitate, sorbitan monooleate, Triton X-100, hexanoic acid, heptanoic acid, methyl laurate, isopropyl myristate, isopropyl palmitate, methyl palmitate, diethyl sebaccate, sodium oleate, urea, lauryl amine, caprolactam, methyl pyrrolidone, octyl pyrrolidone, methyl piperazine, phenyl piperazine, Carbopol 934P, glyccyrhetinic acid, bromelain, pinene oxide, limonene, cineole, octyl dodecanol, fenchone, menthone, trimethoxy propylene methyl benzene, a cell-penetrating peptide, KLAKLAK, polyarginine, penetratin, HIV-1 Tat, macrogol-15-hydroxystearate, Solutol HS 15, CriticalSorb, a taurocholate, a taurodeoxycholate, a sulfoxide, decyl methyl sulfoxide, dimethyl sulfoxide, cyclopentadecalactone, 8-(N-2-hydroxy-5-chloro-benzoyl)-amino-caprylic acid, N-(10-[2-hydroxybenzoyl]amino)decanoic acid, dodecyl-2-N,N-dimethylamino propionate, D-α-tocopheryl polyethylene glycol-1000 succinate, and pharmaceutically acceptable salts thereof.

25. The peptide drug for use according to item 24 or the copper salt/complex for use according to item 24 or the zinc salt/complex for use according to item 24 or the iron salt/complex for use according to item 24 or the complexing agent for use according to item 24 or the pharmaceutical composition of item 24 or the pharmaceutical dosage form of item 24, wherein said absorption enhancer is a fatty acid acylated amino acid selected from sodium lauroyl alaninate, N-dodecanoyl-L-alanine, sodium lauroyl asparaginate, N-dodecanoyl-L-asparagine, sodium lauroyl aspartic acid, N-dodecanoyl-L-aspartic acid, sodium lauroyl cysteinate, N-dodecanoyl-L-cysteine, sodium lauroyl glutamic acid, N-dodecanoyl-L-glutamic acid, sodium lauroyl glutaminate, N-dodecanoyl-L-glutamine, sodium lauroyl glycinate, N-dodecanoyl-L-glycine, sodium lauroyl histidinate, N-dodecanoyl-L-histidine, sodium lauroyl isoleucinate, N-dodecanoyl-L-isoleucine, sodium lauroyl leucinate, N-dodecanoyl-L-leucine, sodium lauroyl methioninate, N-dodecanoyl-L-methionine, sodium lauroyl phenylalaninate, N-dodecanoyl-L-phenylalanine, sodium lauroyl prolinate, N-dodecanoyl-L-proline, sodium lauroyl serinate, N-dodecanoyl-L-serine, sodium lauroyl threoninate, N-dodecanoyl-L-threonine, sodium lauroyl tryptophanate, N-dodecanoyl-L-tryptophane, sodium lauroyl tyrosinate, N-dodecanoyl-L-tyrosine, sodium lauroyl valinate, N-dodecanoyl-L-valine, sodium lauroyl sarcosinate, N-dodecanoyl-L-sarcosine, sodium capric alaninate, N-decanoyl-L-alanine, sodium capric asparaginate, N-decanoyl-L-asparagine, sodium capric aspartic acid, N-decanoyl-L-aspartic acid, sodium capric cysteinate, N-decanoyl-L-cysteine, sodium capric glutamic acid, N-decanoyl-L-glutamic acid, sodium capric glutaminate, N-decanoyl-L-glutamine, sodium capric glycinate, N-decanoyl-L-glycine, sodium capric histidinate, N-decanoyl-L-histidine, sodium capric isoleucinate, N-decanoyl-L-isoleucine, sodium capric leucinate, N-decanoyl-L-leucine, sodium capric methioninate, N-decanoyl-L-methionine, sodium capric phenylalaninate, N-decanoyl-L-phenylalanine, sodium capric prolinate, N-decanoyl-L-proline, sodium capric serinate, N-decanoyl-L-serine, sodium capric threoninate, N-decanoyl-L-threonine, sodium capric tryptophanate, N-decanoyl-L-tryptophane, sodium capric tyrosinate, N-decanoyl-L-tyrosine, sodium capric valinate, N-decanoyl-L-valine, sodium capric sarcosinate, sodium oleoyl sarcosinate, sodium N-decylleucine, sodium stearoyl glutamate, sodium myristoyl glutamate, sodium lauroyl glutamate, sodium cocoyl glutamate, sodium cocoyl glycinate, sodium N-decyl leucine, sodium cocoyl glycine, sodium cocoyl glutamate, sodium lauroyl alaninate, N-dodecanoyl-L-alanine, sodium lauroyl asparaginate, N-dodecanoyl-L-asparagine, sodium lauroyl aspartic acid, N-dodecanoyl-L-aspartic acid, sodium lauroyl cysteinate, N-dodecanoyl-L-cysteine, sodium lauroyl glutamic acid, N-dodecanoyl-L-glutamic acid, sodium lauroyl glutaminate, N-dodecanoyl-L-glutamine, sodium lauroyl glycinate, N-dodecanoyl-L-glycine, sodium lauroyl histidinate, N-dodecanoyl-L-histidine, sodium lauroyl isoleucinate, N-dodecanoyl-L-isoleucine, sodium lauroyl leucinate, N-dodecanoyl-L-leucine, sodium lauroyl methinoninate, N-dodecanoyl-L-methionine, sodium lauroyl phenylalaninate, N-dodecanoyl-L-phenylalanine, sodium lauroyl prolinate, N-dodecanoyl-L-proline, sodium lauroyl serinate, N-dodecanoyl-L-serine, sodium lauroyl threoninate, N-dodecanoyl-L-threonine, sodium lauroyl tryptophanate, N-dodecanoyl-L-tryptophane, sodium lauroyl tyrosinate, N-dodecanoyl-L-tyrosine, sodium lauroyl valinate, N-dodecanoyl-L-valine, N-dodecanoyl-L-sarcosine, sodium capric alaninate, N-decanoyl-L-alanine, sodium capric asparaginate, N-decanoyl-L-asparagine, sodium capric aspartic acid, N-decanoyl-L-aspartic acid, Sodium capric cysteinate, N-decanoyl-L-cysteine, sodium capric glutamic acid, N-decanoyl-L-glutamic acid, sodium capric glutaminate, N-decanoyl-L-glutamine, sodium capric glycinate, N-decanoyl-L-glycine, sodium capric histidinate, N-decanoyl-L-histidine, sodium capric isoleucinate, N-decanoyl-L-isoleucine, sodium capric leucinate, N-decanoyl-L-leucine, sodium capric methioninate, N-decanoyl-L-methionine, sodium capric phenylalaninate, N-decanoyl-L-phenylalanine, sodium capric prolinate, N-decanoyl-L-proline, sodium capric serinate, N-decanoyl-L-serine, sodium capric threoninate, N-decanoyl-L-threonine, sodium capric tryptophanate, N-decanoyl-L-tryptophane, sodium capric tyrosinate, N-decanoyl-L-tyrosine, sodium capric valinate, N-decanoyl-L-valine, sodium capric sarcosinate, sodium oleoyl sarcosinate, and pharmaceutically acceptable salts thereof.

26. The peptide drug for use according to item 23 or the copper salt/complex for use according to item 23 or the zinc salt/complex for use according to item 23 or the iron salt/complex for use according to item 23 or the complexing agent for use according to item 23 or the pharmaceutical composition of item 23 or the pharmaceutical dosage form of item 23, wherein said absorption enhancer is sodium N-[8-(2-hydroxybenzoyl)amino]caprylate.

27. The pharmaceutical composition of any one of items 6, 8 to 10, 12 to 14, 16, 17 or 19 to 26, wherein said pharmaceutical composition is a solid composition or a liquid composition that contains less than about 5% (v/v) of water.

28. The pharmaceutical composition of any one of items 23 to 27 or the pharmaceutical dosage form of any one of items 23 to 27, wherein said pharmaceutical composition or said pharmaceutical dosage form comprises:
the copper salt/complex in an amount of about 0.1 mg to about 20 mg calculated as $Cu^+$ or $Cu^{2+}$ per dosage unit, and/or the zinc salt/complex in an amount of about 0.1 mg to about 50 mg calcuated as $Zn^{2+}$ per dosage unit, and/or the iron salt/complex in an amount of about 1 mg to about 100 mg calculated as $Fe^{2+}$ or $Fe^{3+}$ per dosage unit;
the complexing agent in an amount of about 1 mg to about 1000 mg per dosage unit; and
the absorption enhancer in an amount of about 10 mg to about 1000 mg per dosage unit.

29. Use of a peptide drug having a molecular weight of equal to or less than 5 kDa in the preparation of a medicament which is to be administered orally in combination with:
a pharmaceutically acceptable copper salt/complex and/or a pharmaceutically acceptable zinc salt/complex and/or a pharmaceutically acceptable iron salt/complex; and
a pharmaceutically acceptable complexing agent.

30. Use of a pharmaceutically acceptable copper salt/complex in the preparation of a medicament which is to be administered orally in combination with:
a pharmaceutically acceptable complexing agent; and
a peptide drug having a molecular weight of equal to or less than 5 kDa.

31. Use of a pharmaceutically acceptable zinc salt/complex in the preparation of a medicament which is to be administered orally in combination with:
   a pharmaceutically acceptable complexing agent; and
   a peptide drug having a molecular weight of equal to or less than 5 kDa.
32. Use of a pharmaceutically acceptable iron salt/complex in the preparation of a medicament which is to be administered orally in combination with:
   a pharmaceutically acceptable complexing agent; and
   a peptide drug having a molecular weight of equal to or less than 5 kDa.
32. Use of a pharmaceutically acceptable complexing agent in the preparation of a medicament which is to be administered orally in combination with:
   a pharmaceutically acceptable copper salt/complex and/or a pharmaceutically acceptable zinc salt/complex and/or a pharmaceutically acceptable iron salt/complex; and
   a peptide drug having a molecular weight of equal to or less than 5 kDa.
33. A method of treating or preventing a disease/disorder, the method comprising orally administering, to a subject in need thereof, a peptide drug having a molecular weight of equal to or less than 5 kDa, a pharmaceutically acceptable copper salt/complex and/or a pharmaceutically acceptable zinc salt/complex and/or a pharmaceutically acceptable iron salt/complex, and a pharmaceutically acceptable complexing agent.
34. A method of orally delivering a peptide drug having a molecular weight of equal to or less than 5 kDa, the method comprising orally administering said peptide drug in combination with a pharmaceutically acceptable copper salt/complex and/or a pharmaceutically acceptable zinc salt/complex and/or a pharmaceutically acceptable iron salt/complex and with a pharmaceutically acceptable complexing agent to a subject in need thereof.
35. The use of any one of items 29 to 32 or the method of item 33 or 34, wherein the peptide drug has a molecular weight of about 500 Da to about 4 kDa.
36. The use of any one of items 29 to 32 or 35 or the method of any one of items 33 to 35, wherein the peptide drug has a molecular weight of about 1 kDa to about 3 kDa.
37. The use of any one of items 29 to 32 or the method of item 33 or 34, wherein the peptide drug is selected from GLP-1, a GLP-1 analog, an acylated GLP-1 analog, a diacylated GLP-1 analog, a long-acting albumin-binding fatty acid-derivatized GLP-1 analog, a GLP-1 agonist, semaglutide, liraglutide, exenatide, exendin-4, lixisenatide, taspoglutide, langlenatide, GLP-1(7-37), GLP-1(7-36)NH$_2$, a dual agonist of the GLP-1 receptor and the glucagon receptor, oxyntomodulin, GLP-2, a GLP-2 agonist or analog, teduglutide, elsiglutide, amylin, an amylin analog, pramlintide, a somatostatin analog, octreotide, lanreotide, pasireotide, goserelin, buserelin, peptide YY, a peptide YY analog, glatiramer, leuprolide, desmopressin, a glycopeptide antibiotic, vancomycin, teicoplanin, telavancin, bleomycin, ramoplanin, decaplanin, bortezomib, cosyntropin, sermorelin, luteinizing-hormone-releasing hormone, calcitonin, calcitonin-salmon, pentagastrin, oxytocin, neseritide, enfuvirtide, eptifibatide, cyclosporine, glucagon, viomycin, thyrotropin-releasing hormone, leucine-enkephalin, methionine-enkephalin, substance P, a parathyroid hormone fragment, teriparatide, PTH(1-31), PTH(2-34), linaclotide, carfilzomib, icatibant, cilengitide, a prostaglandin F2α receptor modulator, PDC31, and pharmaceutically acceptable salts thereof.
38. The use of any one of items 29 to 32 or 35 to 37 or the method of any one of items 33 to 37, wherein said peptide drug is to be administered in combination with a pharmaceutically acceptable copper salt/complex.
39. The use of any one of items 29 to 32 or 35 to 38 or the method of any one of items 33 to 38, wherein said copper salt/complex is a copper(I) salt/complex or a copper(II) salt/complex.
40. The use of item 39 or the method of item 39, wherein said copper salt/complex is a copper(II) salt/complex which is selected from copper sulfate, copper carbonate, a copper(II) amino acid complex, copper(II) lysine complex, copper(II) glycinate, copper(II) EDTA complex, copper(II) chitosan complex, copper(II) citrate, copper(II) gluconate, copper(II) lactate, copper lactate gluconate, and copper(II) orotate.
41. The use of item 39 or the method of item 39, wherein said copper salt/complex is a copper(I) salt/complex which is selected from copper(I) chloride and copper(I) acetate.
42. The use of any one of items 29 to 32 or 35 to 37 or the method of any one of items 33 to 37, wherein said peptide drug is to be administered in combination with a pharmaceutically acceptable zinc salt/complex.
43. The use of any one of items 29 to 32, 35 to 37 or 42 or the method of any one of items 33 to 37 or 42, wherein said zinc salt/complex is a zinc(II) salt/complex.
44. The use of item 43 or the method of item 43, wherein said zinc salt/complex is a zinc(II) salt/complex which is selected from zinc sulfate, zinc chloride, zinc acetate, zinc oxide, zinc ascorbate, zinc caprylate, zinc gluconate, zinc stearate, zinc carbonate, zinc orotate, a zinc amino acid complex, zinc glycinate, zinc arginate, zinc picolinate, zinc pidolate, zinc carnosine, zinc undecanoate, zinc undecylenate, zinc methionine, zinc lactate, and zinc lactate gluconate.
45. The use of any one of items 29 to 32 or 35 to 37 or the method of any one of items 33 to 37, wherein said peptide drug is to be administered in combination with a pharmaceutically acceptable iron salt/complex.
46. The use of any one of items 29 to 32, 35 to 37 or 45 or the method of any one of items 33 to 37 or 45, wherein said iron salt/complex is an iron(II) salt/complex or an iron(III) salt/complex.
47. The use of item 46 or the method of item 46, wherein said iron salt/complex is an iron(II) salt/complex selected from iron(II) gluconate, iron(II) orotate, iron(II) tartrate, iron(II) fumarate, iron(II) sulfate, iron(II) lactate, iron(II) lactate gluconate, iron(II) acetate, iron(II) carbonate, iron(II) citrate, iron(II) oxide, iron(II) hydroxide, iron(II) ascorbate, an iron(II) amino acid complex, and ferrous bis-glycinate.
48. The use of item 46 or the method of item 46, wherein said iron salt/complex is an iron(III) salt/complex selected from iron(III) chloride, iron(III) sulfate, iron(III) oxide, iron(III)carbonate, iron(III) acetate, iron(III) phosphate, iron(III) hydroxide, iron(III) tartrate, iron(III) lactate, iron(III) glycinate, iron(III) EDTA, iron(III) ascorbate, and ammonium iron(III) citrate.
49. The use of any one of items 29 to 32 or 35 to 48 or the method of any one of items 33 to 48, wherein said complexing agent is selected from mannitol, sorbitol, saccharose, sucrose, trehalose, calcium phosphate, basic calcium phosphate, calcium hydrogen phosphate, dicalcium phosphate hydrate, disodium phosphate dihydrate, an amino acid, EDTA, EGTA, citrate, a complexing peptide, glycyl-histidyl-lysine peptide, polyacrylic acid, a polyacrylic acid derivative, a carbomer, a carbomer derivative, sodium alginate, a silicate, kaolin, hydroxypropyl methylcellulose, methylcellulose, glycerol, sodium dodecyl sulfate, calcium sulfate, calcium carbonate, and pharmaceutically acceptable salts thereof.

50. The use of any one of items 29 to 32 or 35 to 49 or the method of any one of items 33 to 49, wherein an absorption enhancer is further to be administered orally.

51. The use of item 50 or the method of item 50, wherein said absorption enhancer is selected from $C_{8-20}$ alkanoyl carnitine, salicylic acid, a salicylic acid derivative, 3-methoxysalicylic acid, 5-methoxysalicylic acid, homovanillic acid, a $C_{8-20}$ alkanoic acid, citric acid, tartaric acid, a fatty acid acylated amino acid, a $C_{8-20}$ alkanoyl sarcosinate, an alkylsaccharide, a $C_{8-10}$ alkylpolysaccharide, n-octyl-beta-D-glucopyranoside, n-dodecyl-beta-D-maltoside, n-tetradecyl-beta-D-maltoside, tridecyl-beta-D-maltoside, sucrose laurate, sucrose myristate, sucrose palmitate, sucrose cocoate, sucrose mono-dodecanoate, sucrose mono-tridecanoate, sucrose mono-tetradecanoate, a coco-glucoside, a cyclodextrine, α-cyclodextrin, β-cyclodextrin, γ-cyclodextrin, methyl-β-cyclodextrin, hydroxypropyl β-cyclodextrin, sulfobutylether β-cyclodextrin, N-[8-(2-hydroxybenzoyl)amino]caprylic acid, sodium N-[8-(2-hydroxybenzoyl)amino]caprylate, a sodium N-[8-(2-hydroxybenzoyl)amino]caprylate derivative, a thiomer, a mucoadhesive polymer having a vitamin B partial structure, a calcium chelating compound, ethylenediaminetetraacetic acid, ethylene glycol tetraacetic acid, polyacrylic acid, cremophor EL, chitosan, N,N,N-trimethyl chitosan, benzalkonium chloride, bestatin, cetylpyridinium chloride, cetyltrimethylammonium bromide, a $C_{2-20}$ alkanol, a $C_{8-20}$ alkenol, a $C_{8-20}$ alkenoic acid, dextran sulfate, diethyleneglycol monoethyl ether, 1-dodecylazacyclo-heptan-2-one, caprylocaproyl polyoxylglycerides, ethyl caprylate, glyceryl monolaurate, lysophosphatidylcholine, menthol, a $C_{8-20}$ alkylamine, a $C_{8-20}$ alkenylamine, phosphatidylcholine, a poloxamer, polyethylene glycol monolaurate, polyoxyethylene, polypropylene glycol monolaurate, a polysorbate, cholic acid, a deoxycholate, sodium glycocholate, sodium glycodeoxycholate, sodium lauryl sulfate, sodium decyl sulfate, sodium octyl sulfate, sodium laureth sulfate, N-lauryl sarcosinate, decyltrimethyl ammonium bromide, benzyldimethyl dodecyl ammonium chloride, myristyltrimethyl ammonium chloride, dodecyl pyridinium chloride, decyldimethyl ammonio propane sulfonate, myristyldimethyl ammonio propane sulfonate, palmityldimethyl ammonio propane sulfonate, ChemBetaine CAS, ChemBetaine Oleyl, Nonylphenoxypolyoxyethylene, polyoxyethylene sorbitan monolaurate, polyoxyethylene sorbitan monopalmitate, sorbitan monooleate, Triton X-100, hexanoic acid, heptanoic acid, methyl laurate, isopropyl myristate, isopropyl palmitate, methyl palmitate, diethyl sebaccate, sodium oleate, urea, lauryl amine, caprolactam, methyl pyrrolidone, octyl pyrrolidone, methyl piperazine, phenyl piperazine, Carbopol 934P, glyccyrhetinic acid, bromelain, pinene oxide, limonene, cineole, octyl dodecanol, fenchone, menthone, trimethoxy propylene methyl benzene, a cell-penetrating peptide, KLAKLAK, polyarginine, penetratin, HIV-1 Tat, macrogol-15-hydroxystearate, Solutol HS 15, CriticalSorb, a taurocholate, a taurodeoxycholate, a sulfoxide, decyl methyl sulfoxide, dimethyl sulfoxide, cyclopentadecalactone, 8-(N-2-hydroxy-5-chloro-benzoyl)-amino-caprylic acid, N-(10-[2-hydroxybenzoyl]amino)decanoic acid, dodecyl-2-N,N-dimethylamino propionate, D-α-tocopheryl polyethylene glycol-1000 succinate, and pharmaceutically acceptable salts thereof.

52. The use of item 51 or the method of item 51, wherein said absorption enhancer is a fatty acid acylated amino acid selected from sodium lauroyl alaninate, N-dodecanoyl-L-alanine, sodium lauroyl asparaginate, N-dodecanoyl-L-asparagine, sodium lauroyl aspartic acid, N-dodecanoyl-L-aspartic acid, sodium lauroyl cysteinate, N-dodecanoyl-L-cysteine, sodium lauroyl glutamic acid, N-dodecanoyl-L-glutamic acid, sodium lauroyl glutaminate, N-dodecanoyl-L-glutamine, sodium lauroyl glycinate, N-dodecanoyl-L-glycine, sodium lauroyl histidinate, N-dodecanoyl-L-histidine, sodium lauroyl isoleucinate, N-dodecanoyl-L-isoleucine, sodium lauroyl leucinate, N-dodecanoyl-L-leucine, sodium lauroyl methioninate, N-dodecanoyl-L-methionine, sodium lauroyl phenylalaninate, N-dodecanoyl-L-phenylalanine, sodium lauroyl prolinate, N-dodecanoyl-L-proline, sodium lauroyl serinate, N-dodecanoyl-L-serine, sodium lauroyl threoninate, N-dodecanoyl-L-threonine, sodium lauroyl tryptophanate, N-dodecanoyl-L-tryptophane, sodium lauroyl tyrosinate, N-dodecanoyl-L-tyrosine, sodium lauroyl valinate, N-dodecanoyl-L-valine, sodium lauroyl sarcosinate, N-dodecanoyl-L-sarcosine, sodium capric alaninate, N-decanoyl-L-alanine, sodium capric asparaginate, N-decanoyl-L-asparagine, sodium capric aspartic acid, N-decanoyl-L-aspartic acid, sodium capric cysteinate, N-decanoyl-L-cysteine, sodium capric glutamic acid, N-decanoyl-L-glutamic acid, sodium capric glutaminate, N-decanoyl-L-glutamine, sodium capric glycinate, N-decanoyl-L-glycine, sodium capric histidinate, N-decanoyl-L-histidine, sodium capric isoleucinate, N-decanoyl-L-isoleucine, sodium capric leucinate, N-decanoyl-L-leucine, sodium capric methioninate, N-decanoyl-L-methionine, sodium capric phenylalaninate, N-decanoyl-L-phenylalanine, sodium capric prolinate, N-decanoyl-L-proline, sodium capric serinate, N-decanoyl-L-serine, sodium capric threoninate, N-decanoyl-L-threonine, sodium capric tryptophanate, N-decanoyl-L-tryptophane, sodium capric tyrosinate, N-decanoyl-L-tyrosine, sodium capric valinate, N-decanoyl-L-valine, sodium capric sarcosinate, N-decanoyl-L-sarcosine, sodium oleoyl sarcosinate, sodium N-decylleucine, sodium stearoyl glutamate, sodium myristoyl glutamate, sodium lauroyl glutamate, sodium cocoyl glutamate, sodium cocoyl glycinate, sodium N-decyl leucine, sodium cocoyl glycine, sodium cocoyl glutamate, sodium lauroyl alaninate, N-dodecanoyl-L-alanine, sodium lauroyl asparaginate, N-dodecanoyl-L-asparagine, sodium lauroyl aspartic acid, N-dodecanoyl-L-aspartic acid, sodium lauroyl cysteinate, N-dodecanoyl-L-cysteine, sodium lauroyl glutamic acid, N-dodecanoyl-L-glutamic acid, sodium lauroyl glutaminate, N-dodecanoyl-L-glutamine, sodium lauroyl glycinate, N-dodecanoyl-L-glycine, sodium lauroyl histidinate, N-dodecanoyl-L-histidine, sodium lauroyl isoleucinate, N-dodecanoyl-L-isoleucine, sodium lauroyl leucinate, N-dodecanoyl-L-leucine, sodium lauroyl methinoninate, N-dodecanoyl-L-methionine, sodium lauroyl phenylalaninate, N-dodecanoyl-L-phenylalanine, sodium lauroyl prolinate, N-dodecanoyl-L-proline, sodium lauroyl serinate, N-dodecanoyl-L-serine, sodium lauroyl threoninate, N-dodecanoyl-L-threonine, sodium lauroyl tryptophanate, N-dodecanoyl-L-tryptophane, sodium lauroyl tyrosinate, N-dodecanoyl-L-tyrosine, sodium lauroyl valinate, N-dodecanoyl-L-valine, N-dodecanoyl-L-sarcosine, sodium capric alaninate, N-decanoyl-L-alanine, sodium capric asparaginate, N-decanoyl-L-asparagine, sodium capric aspartic acid, N-decanoyl-L-aspartic acid, Sodium capric cysteinate, N-decanoyl-L-cysteine, sodium capric glutamic acid, N-decanoyl-L-glutamic acid, sodium capric glutaminate, N-decanoyl-L-glutamine, sodium capric glycinate, N-decanoyl-L-glycine, sodium capric histidinate, N-decanoyl-L-histidine, sodium capric isoleucinate, N-decanoyl-L-isoleucine, sodium capric leucinate, N-decanoyl-L-leucine, sodium capric methioninate, N-decanoyl-L-methionine, sodium capric phenylalaninate, N-decanoyl-L-phenylalanine, sodium capric prolinate, N-decanoyl-L-proline, sodium capric serinate, N-decanoyl-L-serine, sodium capric threoninate, N-decanoyl-L-threonine, sodium capric tryptophanate, N-decanoyl-L-tryptophane, sodium capric tyrosinate, N-decanoyl-L-tyrosine, sodium capric valinate, N-decanoyl-L-valine, sodium capric sarcosinate, sodium oleoyl sarcosinate, and pharmaceutically acceptable salts thereof.

53. The use of item 50 or the method of item 50, wherein said absorption enhancer is sodium N-[8-(2-hydroxybenzoyl)amino]caprylate.

The present invention also relates to the following embodiments:

1. A peptide drug having a molecular weight of equal to or less than 5 kDa for use as a medicament, wherein said peptide drug is to be administered orally in combination with:
   a pharmaceutically acceptable copper salt/complex and/or a pharmaceutically acceptable zinc salt/complex and/or a pharmaceutically acceptable iron salt/complex; and
   a pharmaceutically acceptable complexing agent.

2. A pharmaceutically acceptable copper salt/complex for use in therapy, wherein said copper salt/complex is to be administered orally in combination with:
   a peptide drug having a molecular weight of equal to or less than 5 kDa; and
   a pharmaceutically acceptable complexing agent.

3. A pharmaceutically acceptable zinc salt/complex for use in therapy, wherein said zinc salt/complex is to be administered orally in combination with:
   a peptide drug having a molecular weight of equal to or less than 5 kDa; and
   a pharmaceutically acceptable complexing agent.

4. A pharmaceutically acceptable iron salt/complex for use in therapy, wherein said iron salt/complex is to be administered orally in combination with:
   a peptide drug having a molecular weight of equal to or less than 5 kDa; and
   a pharmaceutically acceptable complexing agent.

5. A pharmaceutically acceptable complexing agent for use in therapy, wherein said complexing agent is to be administered orally in combination with:
   a peptide drug having a molecular weight of equal to or less than 5 kDa; and
   a pharmaceutically acceptable copper salt/complex and/or a pharmaceutically acceptable zinc salt/complex and/or a pharmaceutically acceptable iron salt/complex.

6. A pharmaceutical composition comprising:
   a peptide drug having a molecular weight of equal to or less than 5 kDa;
   a pharmaceutically acceptable copper salt/complex and/or a pharmaceutically acceptable zinc salt/complex and/or a pharmaceutically acceptable iron salt/complex; and
   a pharmaceutically acceptable complexing agent.

7 A pharmaceutical dosage form comprising:
   a peptide drug having a molecular weight of equal to or less than 5 kDa;
   a pharmaceutically acceptable copper salt/complex and/or a pharmaceutically acceptable zinc salt/complex and/or a pharmaceutically acceptable iron salt/complex; and
   a pharmaceutically acceptable complexing agent;
   wherein the peptide drug is physically separated from the pharmaceutically acceptable copper salt/complex, the pharmaceutically acceptable zinc salt/complex and the pharmaceutically acceptable iron salt/complex within the pharmaceutical dosage form.

8. The peptide drug for use according to embodiment 1 or the copper salt/complex for use according to embodiment 2 or the zinc salt/complex for use according to embodiment 3 or the iron salt/complex for use according to embodiment 4 or the complexing agent for use according to embodiment 5 or the pharmaceutical composition of embodiment 6 or the pharmaceutical dosage form of embodiment 7, wherein the peptide drug has a molecular weight of about 500 Da to about 4 kDa.

9. The peptide drug for use according to embodiment 1 or the copper salt/complex for use according to embodiment 2 or the zinc salt/complex for use according to embodiment 3 or the iron salt/complex for use according to embodiment 4 or the complexing agent for use according to embodiment 5 or the pharmaceutical composition of embodiment 6 or the pharmaceutical dosage form of embodiment 7, wherein the peptide drug is selected from GLP-1, a GLP-1 analog, an acylated GLP-1 analog, a diacylated GLP-1 analog, a long-acting albumin-binding fatty acid-derivatized GLP-1 analog, a GLP-1 agonist, semaglutide, liraglutide, exenatide, exendin-4, lixisenatide, taspoglutide, langlenatide, GLP-1(7-37), GLP-1(7-36)NH$_2$, a dual agonist of the GLP-1 receptor and the glucagon receptor, oxyntomodulin, GLP-2, a GLP-2 agonist or analog, teduglutide, elsiglutide, amylin, an amylin analog, pramlintide, a somatostatin analog, octreotide, lanreotide, pasireotide, goserelin, buserelin, peptide YY, a peptide YY analog, glatiramer, leuprolide, desmopressin, a glycopeptide antibiotic, vancomycin, teicoplanin, telavancin, bleomycin, ramoplanin, decaplanin, bortezomib, cosyntropin, sermorelin, luteinizing-hormone-releasing hormone, calcitonin, calcitonin-salmon, pentagastrin, oxytocin, neseritide, enfuvirtide, eptifibatide, cyclosporine, glucagon, viomycin, thyrotropin-releasing hormone, leucine-enkephalin, methionine-enkephalin, substance P, a parathyroid hormone fragment, teriparatide, PTH(1-31), PTH(2-34), linaclotide, carfilzomib, icatibant, cilengitide, a prostaglandin F2α receptor modulator, PDC31, and pharmaceutically acceptable salts thereof.
10. The peptide drug for use according to any one of embodiments 1, 8 or 9 or the copper salt/complex for use according to any one of embodiments 2, 8 or 9 or the complexing agent for use according to any one of embodiments 5, 8 or 9 or the pharmaceutical composition of any one of embodiments 6, 8 or 9 or the pharmaceutical dosage form of any one of embodiments 7 to 9, wherein said copper salt/complex is a copper(I) salt/complex or a copper(II) salt/complex,
wherein said copper(II) salt/complex is preferably selected from copper sulfate, copper carbonate, a copper(II) amino acid complex, copper(II) lysine complex, copper(II) glycinate, copper(II) EDTA complex, copper(II) chitosan complex, copper(II) citrate, copper(II) gluconate, copper(II) lactate, copper lactate gluconate, and copper(II) orotate, and
wherein said copper(I) salt/complex is preferably selected from copper(I) chloride and copper(I) acetate.
11. The peptide drug for use according to any one of embodiments 1, 8 or 9 or the zinc salt/complex for use according to any one of embodiments 3, 8 or 9 or the complexing agent for use according to any one of embodiments 5, 8 or 9 or the pharmaceutical composition of any one of embodiments 6, 8 or 9 or the pharmaceutical dosage form of any one of embodiments 7 to 9, wherein said zinc salt/complex is a zinc(II) salt/complex which is preferably selected from zinc sulfate, zinc chloride, zinc acetate, zinc oxide, zinc ascorbate, zinc caprylate, zinc gluconate, zinc stearate, zinc carbonate, zinc orotate, a zinc amino acid complex, zinc glycinate, zinc arginate, zinc picolinate, zinc pidolate, zinc carnosine, zinc undecanoate, zinc undecylenate, zinc methionine, zinc lactate, and zinc lactate gluconate.
12. The peptide drug for use according to any one of embodiments 1, 8 or 9 or the iron salt/complex for use according to any one of embodiments 4, 8 or 9 or the complexing agent for use according to any one of embodiments 5, 8 or 9 or the pharmaceutical composition of any one of embodiments 6, 8 or 9 or the pharmaceutical dosage form of any one of embodiments 7 to 9, wherein said iron salt/complex is an iron(II) salt/complex or an iron(III) salt/complex,
wherein said iron(II) salt/complex is preferably selected from iron(II) gluconate, iron(II) orotate, iron(II) tartrate, iron(II) fumarate, iron(II) sulfate, iron(II) lactate, iron(II) lactate gluconate, iron(II) acetate, iron(II) carbonate, iron(II) citrate, iron(II) oxide, iron(II) hydroxide, iron(II) ascorbate, an iron(II) amino acid complex, and ferrous bis-glycinate, and
wherein said iron(III) salt/complex is preferably selected from iron(III) chloride, iron(III) sulfate, iron(III) oxide, iron(III)carbonate, iron(III) acetate, iron(III) phosphate, iron(III) hydroxide, iron(III) tartrate, iron(III) lactate, iron(III) glycinate, iron(III) EDTA, iron(III) ascorbate, and ammonium iron(III) citrate.
13. The peptide drug for use according to any one of embodiments 1 or 8 to 12 or the copper salt/complex for use according to any one of embodiments 2 or 8 to 10 or the zinc salt/complex for use according to any one of embodiments 3, 8, 9 or 11 or the iron salt/complex for use according to any one of embodiments 4, 8, 9 or 12 or the complexing agent for use according to any one of embodiments 5 or 8 to 12 or the pharmaceutical composition of any one of embodiments 6 or 8 to 12 or the pharmaceutical dosage form of any one of embodiments 7 to 12, wherein said complexing agent is selected from mannitol, sorbitol, saccharose, sucrose, trehalose, calcium phosphate, basic calcium phosphate, calcium hydrogen phosphate, dicalcium phosphate hydrate, disodium phosphate dihydrate, an amino acid, EDTA, EGTA, citrate, a complexing peptide, glycyl-histidyl-lysine peptide, polyacrylic acid, a polyacrylic acid derivative, a carbomer, a carbomer derivative, sodium alginate, a silicate, kaolin, hydroxypropyl methylcellulose, methylcellulose, glycerol, sodium dodecyl sulfate, calcium sulfate, calcium carbonate, and pharmaceutically acceptable salts thereof.
14. The peptide drug for use according to any one of embodiments 1 or 8 to 13 or the copper salt/complex for use according to any one of embodiments 2, 8 to 10 or 13 or the zinc salt/complex for use according to any one of embodiments 3, 8, 9, 11 or 13 or the iron salt/complex for use according to any one of embodiments 4, 8, 9, 12 or 13 or the complexing agent for use according to any one of embodiments 5 or 8 to 13 or the pharmaceutical composition of any one of embodiments 6 or 8 to 13 or the pharmaceutical dosage form of any one of embodiments 7 to 13, wherein said peptide drug or said copper salt/complex or said zinc salt/complex or said iron salt/complex or said complexing agent is to be administered orally in combination with an absorption enhancer, or wherein said pharmaceutical composition or said pharmaceutical dosage form further comprises an absorption enhancer.
15. The peptide drug for use according to embodiment 14 or the copper salt/complex for use according to embodiment 14 or the zinc salt/complex for use according to embodiment 14 or the iron salt/complex for use according to embodiment 14 or the complexing agent for use according to embodiment 14 or the pharmaceutical composition of embodiment 14 or the pharmaceutical dosage form of embodiment 14, wherein said absorption enhancer is selected from $C_{8-20}$ alkanoyl carnitine, salicylic acid, a salicylic acid derivative, 3-methoxysalicylic acid, 5-methoxysalicylic acid, homovanillic acid, a $C_{8-20}$ alkanoic acid, citric acid, tartaric acid, a fatty acid acylated amino acid, a $C_{8-20}$ alkanoyl sarcosinate, an alkylsaccharide, a $C_{8-10}$ alkylpolysaccharide, n-octyl-beta-D-glucopyranoside, n-dodecyl-beta-D-maltoside, n-tetradecyl-beta-D-maltoside, tridecyl-beta-D-maltoside, sucrose laurate, sucrose myristate, sucrose palmitate, sucrose cocoate, sucrose mono-dodecanoate, sucrose mono-tridecanoate, sucrose mono-tetradecanoate, a coco-glucoside, a cyclodextrine, α-cyclodextrin, β-cyclodextrin, γ-cyclodextrin, methyl-β-cyclodextrin, hydroxypropyl β-cyclodextrin, sulfobutylether β-cyclodextrin, N-[8-(2-hydroxybenzoyl)amino]caprylic acid, sodium N-[8-(2-hydroxybenzoyl)amino]caprylate, a sodium N-[8-(2-hydroxybenzoyl)amino]caprylate derivative, a thiomer, a mucoadhesive polymer having a vitamin B partial structure, a calcium chelating compound, ethylenediaminetetraacetic acid, ethylene glycol tetraacetic acid, polyacrylic acid, cremophor EL, chitosan, N,N,N-trimethyl chitosan, benzalkonium chloride, bestatin, cetylpyridinium chloride, cetyltrimethylammonium bromide, a $C_{2-20}$ alkanol, a $C_{8-20}$ alkenol, a $C_{8-20}$ alkenoic acid, dextran sulfate, diethyleneglycol monoethyl ether, 1-dodecylazacyclo-heptan-2-one, caprylocaproyl polyoxylglycerides, ethyl caprylate, glyceryl monolaurate, lysophosphatidylcholine, menthol, a $C_{8-20}$ alkylamine, a $C_{8-20}$ alkenylamine, phosphatidylcholine, a poloxamer, polyethylene glycol monolaurate, polyoxyethylene, polypropylene glycol monolaurate, a polysorbate, cholic acid, a deoxycholate, sodium glycocholate, sodium glycodeoxycholate, sodium lauryl sulfate, sodium decyl sulfate, sodium octyl sulfate, sodium laureth sulfate, N-lauryl sarcosinate, decyltrimethyl ammonium bromide, benzyldimethyl dodecyl ammonium chloride, myristyltrimethyl ammonium chloride, dodecyl pyridinium chloride, decyldimethyl ammonio propane sulfonate, myristyldimethyl ammonio propane sulfonate, palmityldimethyl ammonio propane sulfonate, ChemBetaine CAS, ChemBetaine Oleyl, Nonylphenoxypolyoxyethylene, polyoxyethylene sorbitan monolaurate, polyoxyethylene sorbitan monopalmitate, sorbitan monooleate, Triton X-100, hexanoic acid, heptanoic acid, methyl laurate, isopropyl myristate, isopropyl palmitate, methyl palmitate, diethyl sebaccate, sodium oleate, urea, lauryl amine, caprolactam, methyl pyrrolidone, octyl pyrrolidone, methyl piperazine, phenyl piperazine, Carbopol 934P, glyccyrhetinic acid, bromelain, pinene oxide, limonene, cineole, octyl dodecanol, fenchone, menthone, trimethoxy propylene methyl benzene, a cell-penetrating peptide, KLAKLAK, polyarginine, penetratin, HIV-1 Tat, macrogol-15-hydroxystearate, Solutol HS 15, CriticalSorb, a taurocholate, a taurodeoxycholate, a sulfoxide, decyl methyl sulfoxide, dimethyl sulfoxide, cyclopentadecalactone, 8-(N-2-hydroxy-5-chloro-benzoyl)-amino-caprylic acid, N-(10-[2-hydroxybenzoyl]amino)decanoic acid, dodecyl-2-N,N-dimethylamino propionate, D-α-tocopheryl polyethylene glycol-1000 succinate, and pharmaceutically acceptable salts thereof, and wherein said fatty acid acylated amino acid is preferably selected from sodium lauroyl alaninate, N-dodecanoyl-L-alanine, sodium lauroyl asparaginate, N-dodecanoyl-L-asparagine, sodium lauroyl aspartic acid, N-dodecanoyl-L-aspartic acid, sodium lauroyl cysteinate, N-dodecanoyl-L-cysteine, sodium lauroyl glutamic acid, N-dodecanoyl-L-glutamic acid, sodium lauroyl glutaminate, N-dodecanoyl-L-glutamine, sodium lauroyl glycinate, N-dodecanoyl-L-glycine, sodium lauroyl histidinate, N-dodecanoyl-L-histidine, sodium lauroyl isoleucinate, N-dodecanoyl-L-isoleucine, sodium lauroyl leucinate, N-dodecanoyl-L-leucine, sodium lauroyl methioninate, N-dodecanoyl-L-methionine, sodium lauroyl phenylalaninate, N-dodecanoyl-L-phenylalanine, sodium lauroyl prolinate, N-dodecanoyl-L-proline, sodium lauroyl serinate, N-dodecanoyl-L-serine, sodium lauroyl threoninate, N-dodecanoyl-L-threonine, sodium lauroyl tryptophanate, N-dodecanoyl-L-tryptophane, sodium lauroyl tyrosinate, N-dodecanoyl-L-tyrosine, sodium lauroyl valinate, N-dodecanoyl-L-valine, sodium lauroyl sarcosinate, N-dodecanoyl-L-sarcosine, sodium capric alaninate, N-decanoyl-L-alanine, sodium capric asparaginate, N-decanoyl-L-asparagine, sodium capric aspartic acid, N-decanoyl-L-aspartic acid, sodium capric cysteinate, N-decanoyl-L-cysteine, sodium capric glutamic acid, N-decanoyl-L-glutamic acid, sodium capric glutaminate, N-decanoyl-L-glutamine, sodium capric glycinate, N-decanoyl-L-glycine, sodium capric histidinate, N-decanoyl-L-histidine, sodium capric isoleucinate, N-decanoyl-L-isoleucine, sodium capric leucinate, N-decanoyl-L-leucine, sodium capric methioninate, N-decanoyl-L-methionine, sodium capric phenylalaninate, N-decanoyl-L-phenylalanine, sodium capric prolinate, N-decanoyl-L-proline, sodium capric serinate, N-decanoyl-L-serine, sodium capric threoninate, N-decanoyl-L-threonine, sodium capric tryptophanate, N-decanoyl-L-tryptophane, sodium capric tyrosinate, N-decanoyl-L-tyrosine, sodium capric valinate, N-decanoyl-L-valine, sodium capric sarcosinate, N-decanoyl-L-sarcosine, sodium oleoyl sarcosinate, sodium N-decylleucine, sodium stearoyl glutamate, sodium myristoyl glutamate, sodium lauroyl glutamate, sodium cocoyl glutamate, sodium cocoyl glycinate, sodium N-decyl leucine, sodium cocoyl glycine, sodium cocoyl glutamate, sodium lauroyl alaninate, N-dodecanoyl-L-alanine, sodium lauroyl asparaginate, N-dodecanoyl-L-asparagine, sodium lauroyl aspartic acid, N-dodecanoyl-L-aspartic acid, sodium lauroyl cysteinate, N-dodecanoyl-L-cysteine, sodium lauroyl glutamic acid, N-dodecanoyl-L-glutamic acid, sodium lauroyl glutaminate, N-dodecanoyl-L-glutamine, sodium lauroyl glycinate, N-dodecanoyl-L-glycine, sodium lauroyl histidinate, N-dodecanoyl-L-histidine, sodium lauroyl isoleucinate, N-dodecanoyl-L-isoleucine, sodium lauroyl leucinate, N-dodecanoyl-L-leucine, sodium lauroyl methinoninate, N-dodecanoyl-L-methionine, sodium lauroyl phenylalaninate, N-dodecanoyl-L-phenylalanine, sodium lauroyl prolinate, N-dodecanoyl-L-proline, sodium lauroyl serinate, N-dodecanoyl-L-serine, sodium lauroyl threoninate, N-dodecanoyl-L-threonine, sodium lauroyl tryptophanate, N-dodecanoyl-L-tryptophane, sodium lauroyl tyrosinate, N-dodecanoyl-L-tyrosine, sodium lauroyl valinate, N-dodecanoyl-L-valine, N-dodecanoyl-L-sarcosine, sodium capric alaninate, N-decanoyl-L-alanine, sodium capric asparaginate, N-decanoyl-L-asparagine, sodium capric aspartic acid, N-decanoyl-L-aspartic acid, Sodium capric cysteinate, N-decanoyl-L-cysteine, sodium capric glutamic acid, N-decanoyl-L-glutamic acid, sodium capric glutaminate, N-decanoyl-L-glutamine, sodium capric glycinate, N-decanoyl-L-glycine, sodium capric histidinate, N-decanoyl-L-histidine, sodium capric isoleucinate, N-decanoyl-L-isoleucine, sodium capric leucinate, N-decanoyl-L-leucine, sodium capric methioninate, N-decanoyl-L-methionine, sodium capric phenylalaninate, N-decanoyl-L-phenylalanine, sodium capric prolinate, N-decanoyl-L-proline, sodium capric serinate, N-decanoyl-L-serine, sodium capric threoninate, N-decanoyl-L-threonine, sodium capric tryptophanate, N-decanoyl-L-tryptophane, sodium capric tyrosinate, N-decanoyl-L-tyrosine, sodium capric valinate, N-decanoyl-L-valine, sodium capric sarcosinate, sodium oleoyl sarcosinate, and pharmaceutically acceptable salts thereof.

The invention is also described by the following illustrative figures. The appended figures show:

FIG. 1: Pharmacokinetics of the peptide drug liraglutide after oral administration of different liraglutide formulations to Sprague Dawley rats (see Example 2).

Figure 2:
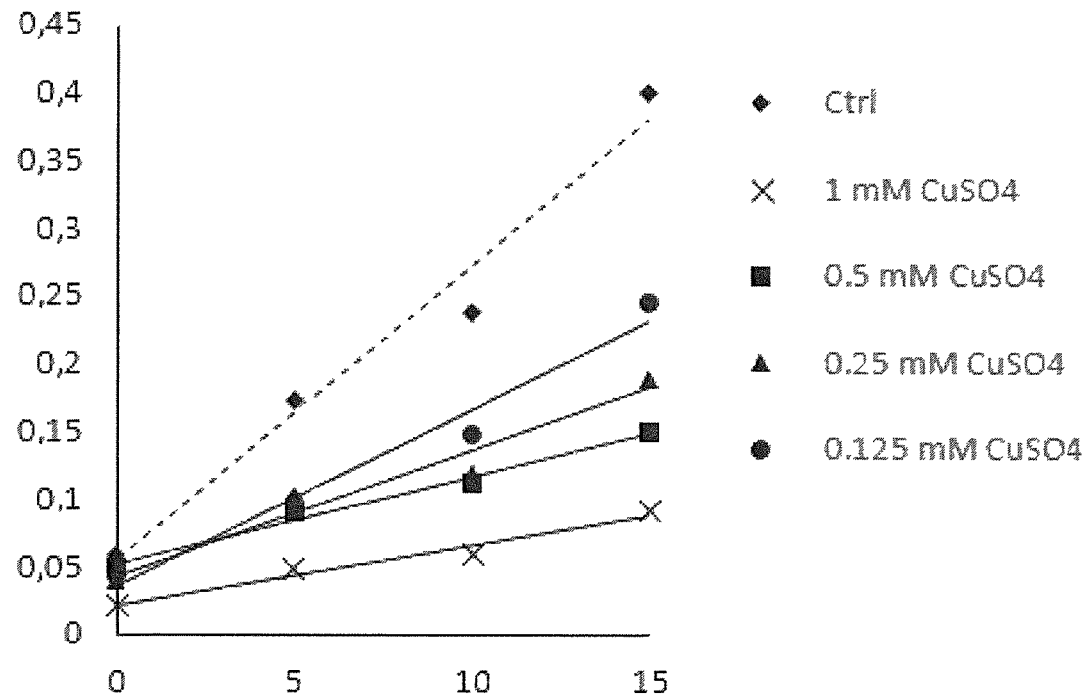

FIG. 2: Concentration-dependent inhibition of chymotrypsin by copper(II)sulfate (see Example 9). The X-axis shows time (minutes), the y-axis shows absorbance at 405 nm.

Figure 3:
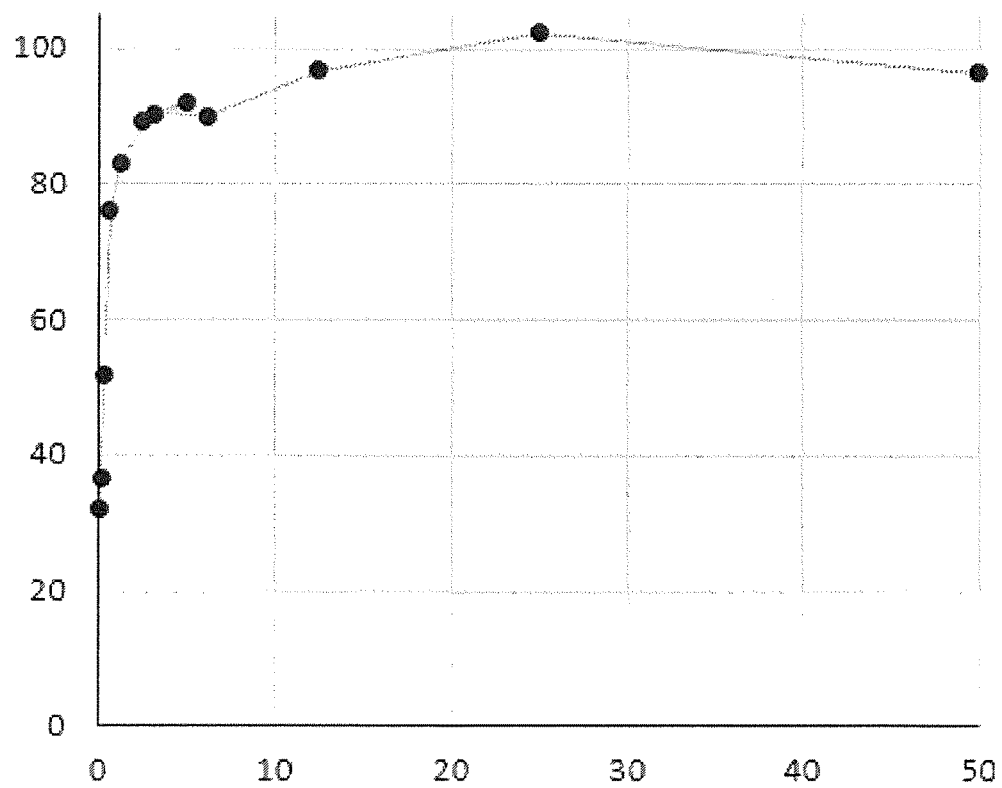

FIG. 3: Concentration-dependent inhibition of trypsin by copper(II)gluconate (see Example 10). The X-axis shows copper gluconate concentrations in the final solutions (mg/ml), the y-axis shows percentage of trypsin inhibition.

Figure 4:
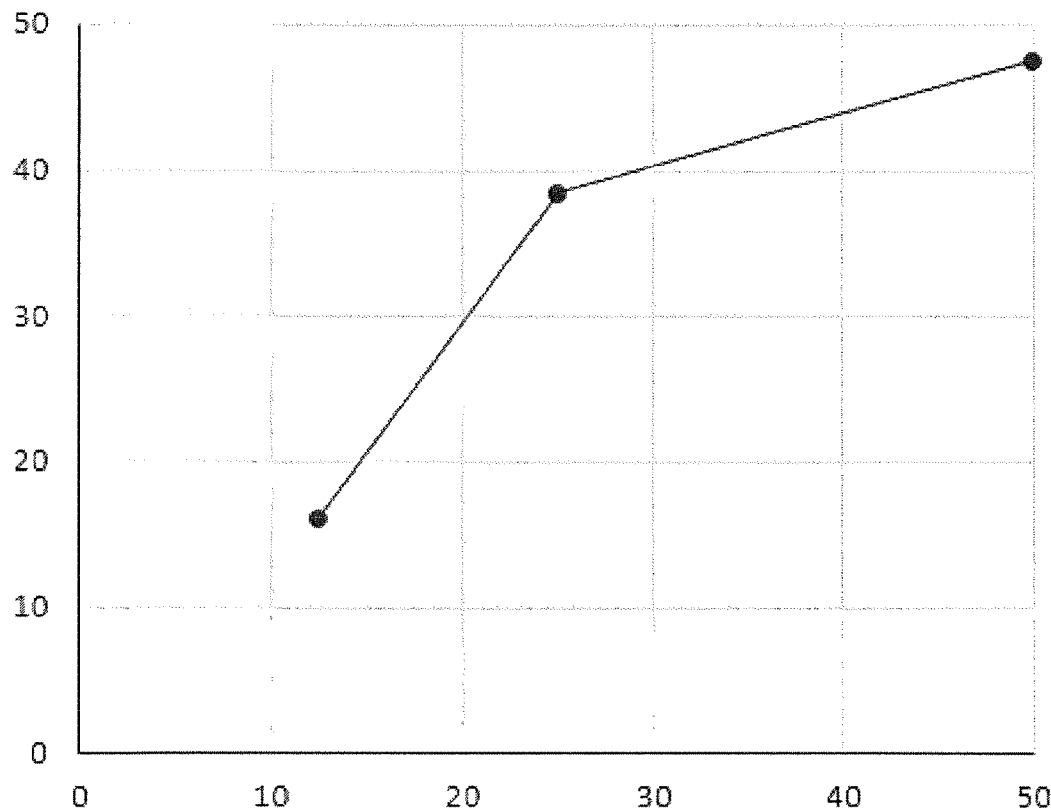

FIG. 4: Concentration-dependent inhibition of trypsin by zinc(II)bisglycinate (see Example 11). The X-axis shows zinc bisglycinate concentrations in the final solutions (mg/ml), the y-axis shows percentage of trypsin inhibition.

Figure 5:
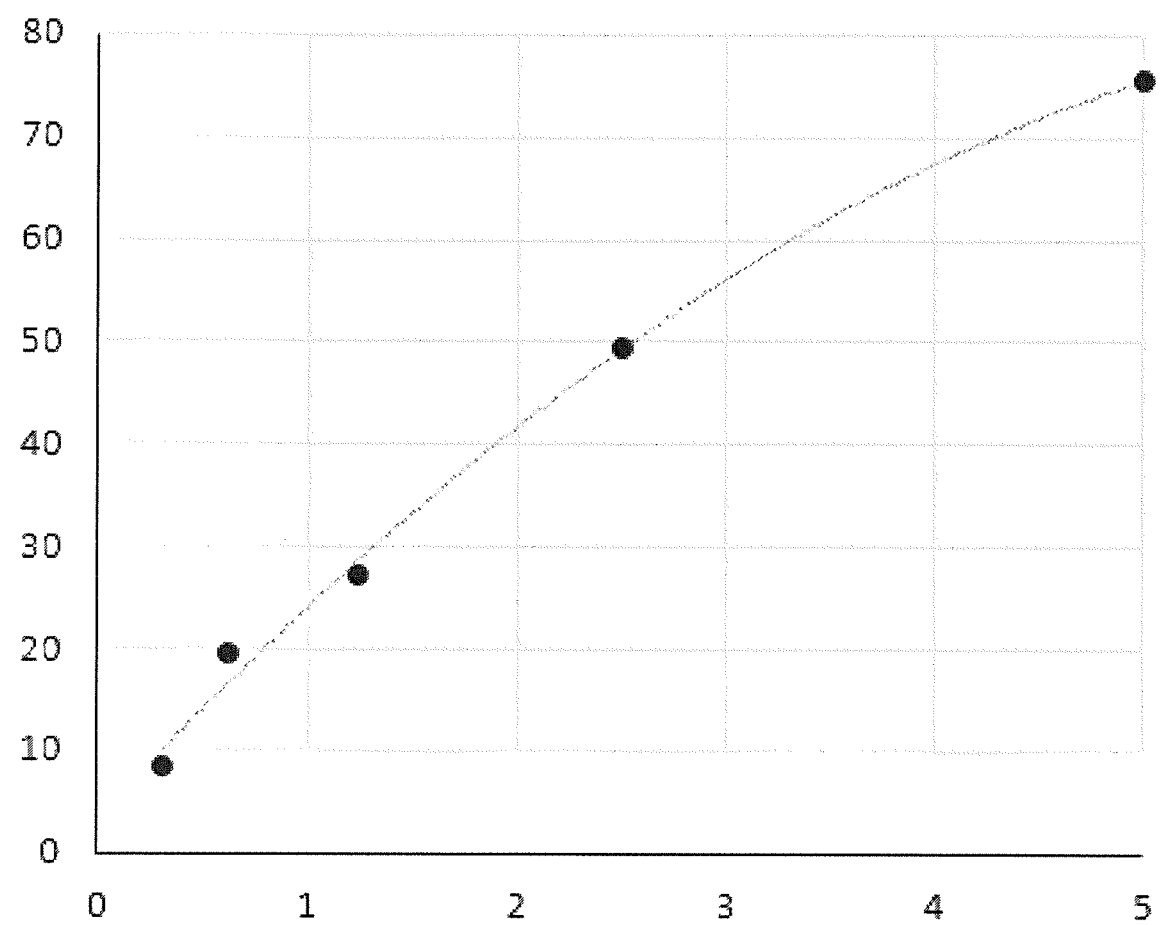

FIG. 5: Concentration-dependent inhibition of trypsin by iron(II)gluconate (see Example 12). The X-axis shows concentrations of iron gluconate in the final solutions (mg/ml), the y-axis shows percentage of trypsin inhibition.

Figure 6:
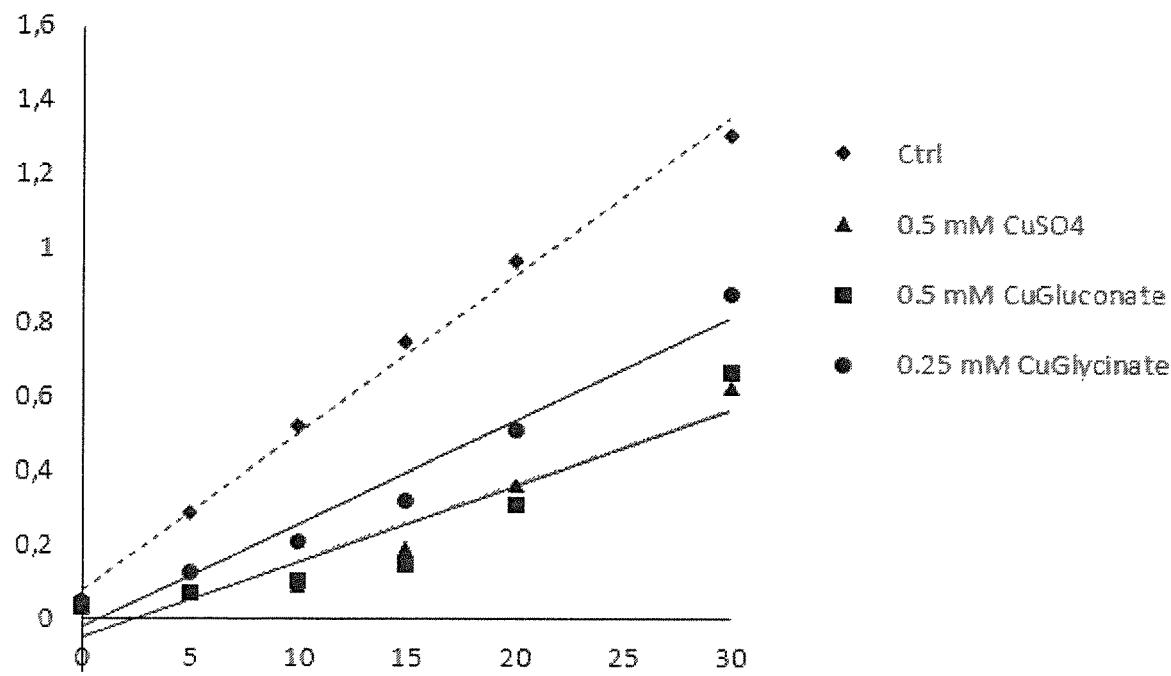

FIG. 6: Inhibition of chymotrypsin by 3 different copper salts (see Example 13). The X-axis shows time (minutes), the y-axis shows absorbance at 405 nm.

Figure 7:
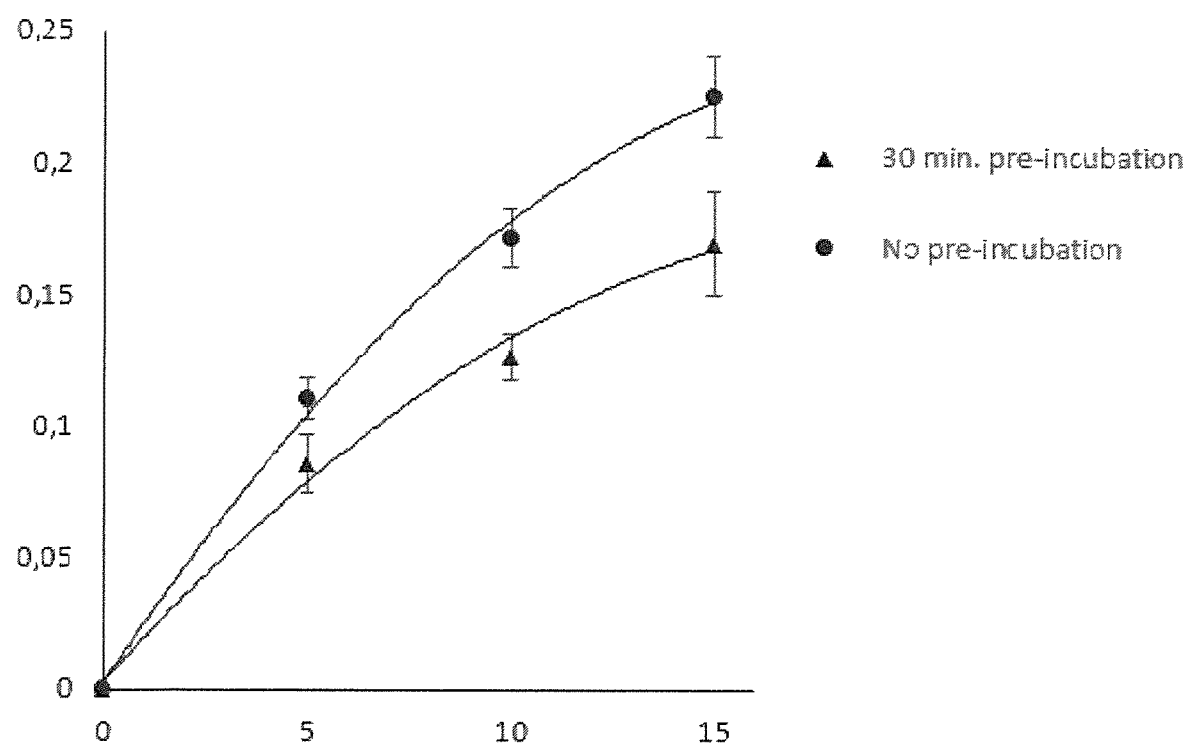

FIG. 7: Influence of copper pre-incubation on chymotrypsin activity (see Example 14). The X-axis shows time (minutes), the y-axis shows absorbance at 405 nm.

Figure 8:
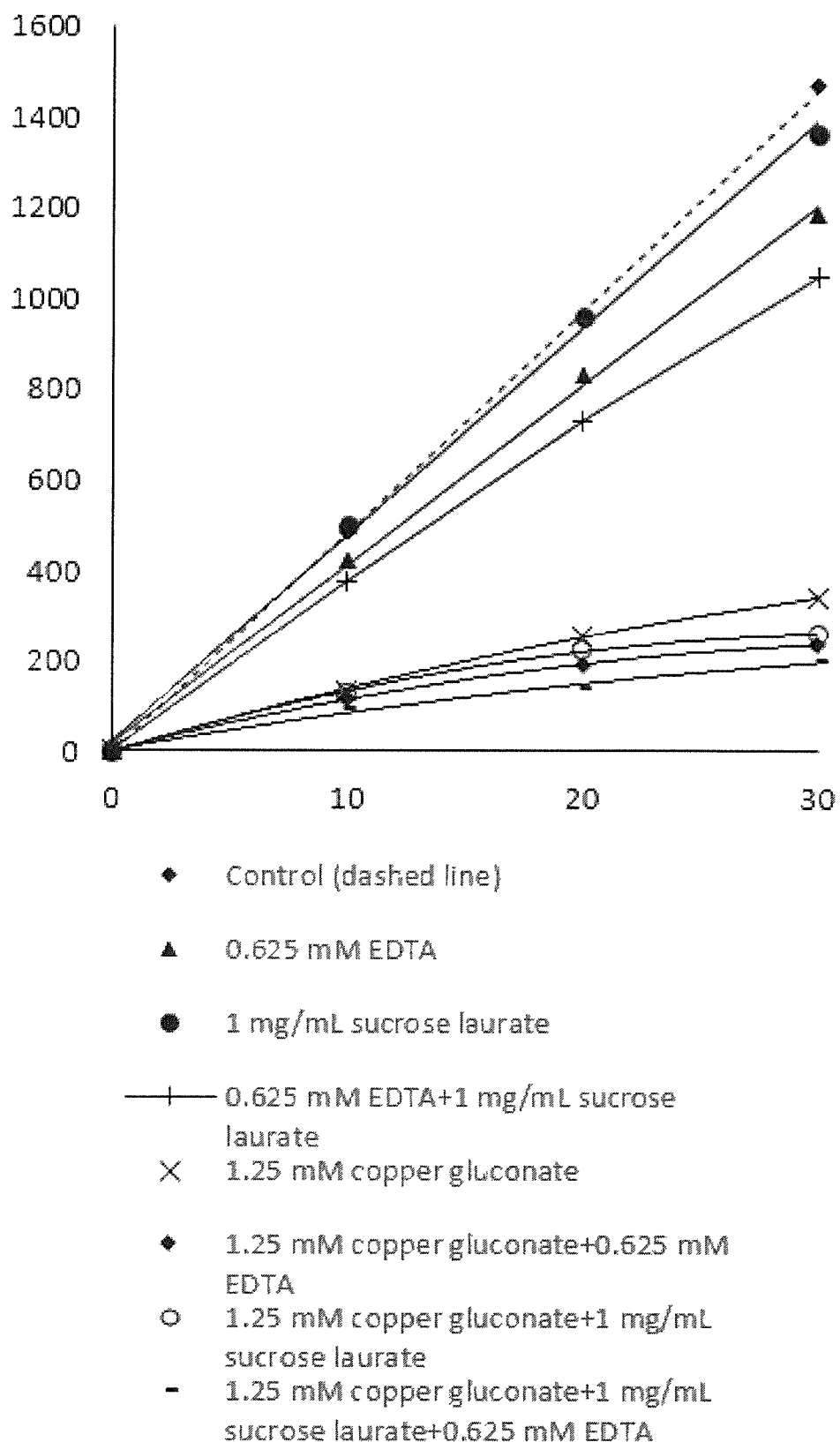

FIG. 8: Chymotrypsin inhibition by copper gluconate, EDTA, sucrose laurate and combinations thereof (see Example 17). The X-axis shows time (minutes), the y-axis shows absorbance at 405 nm.

Figure 9:
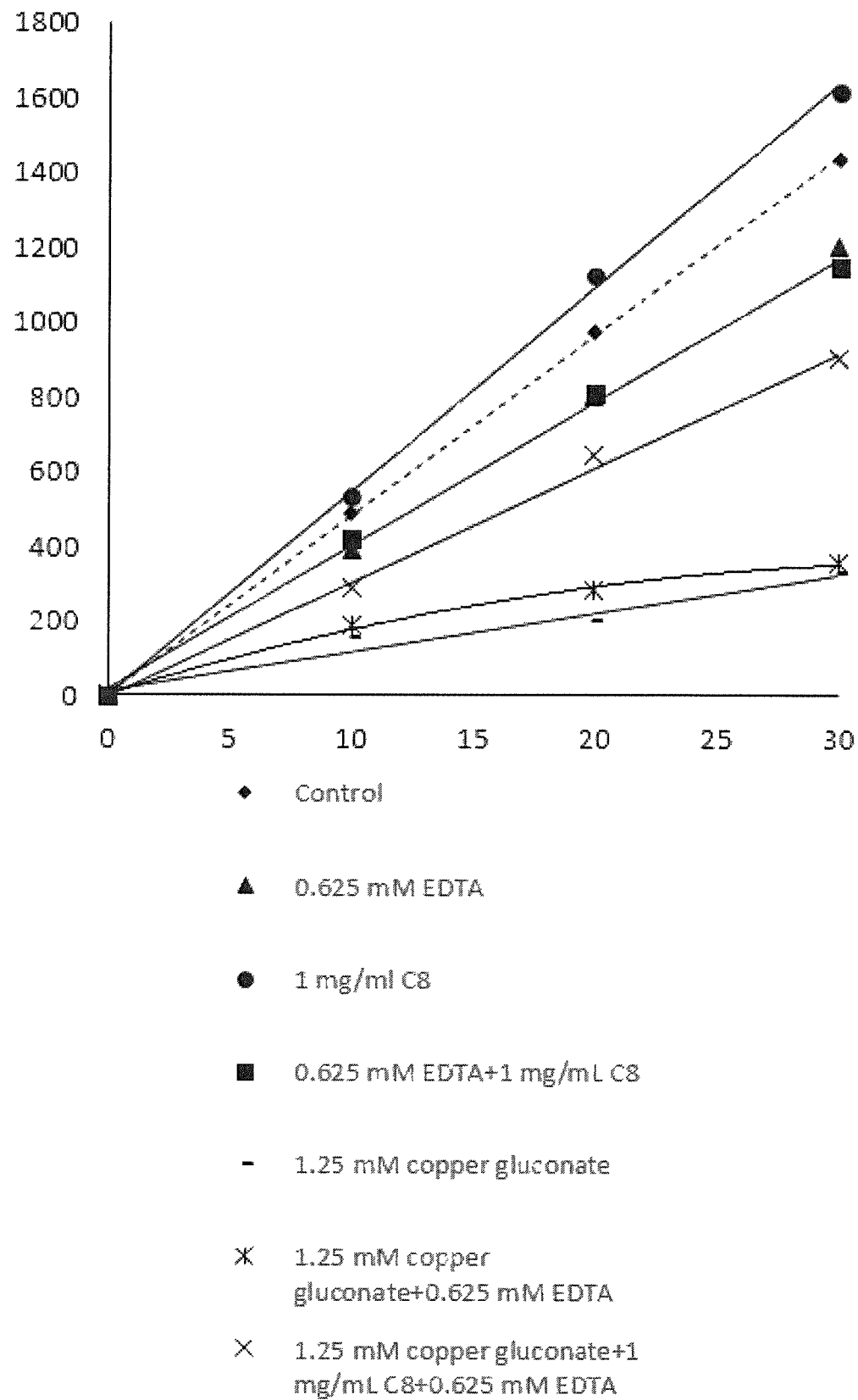

FIG. 9: Chymotrypsin inhibition by copper gluconate, EDTA, sodium caprylate and combinations thereof (see Example 18). The X-axis shows time (minutes), the y-axis shows absorbance at 405 nm.

Figure 10:
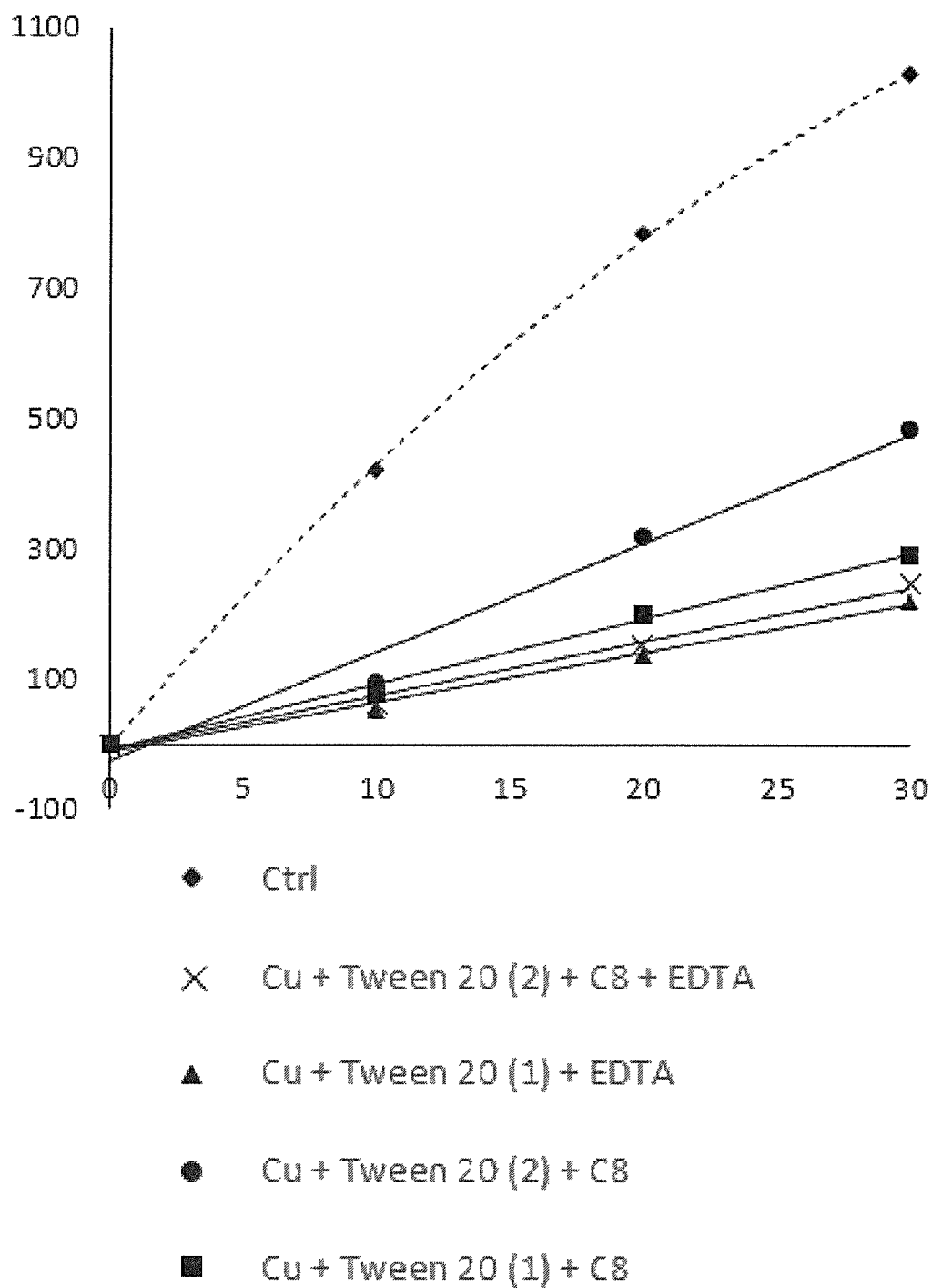

FIG. 10: Chymotrypsin inhibition by copper gluconate, sodium caprylate and Tween 20+/−EDTA (see Example 19). The X-axis shows time (minutes), the y-axis shows absorbance at 405 nm.

Figure 11:
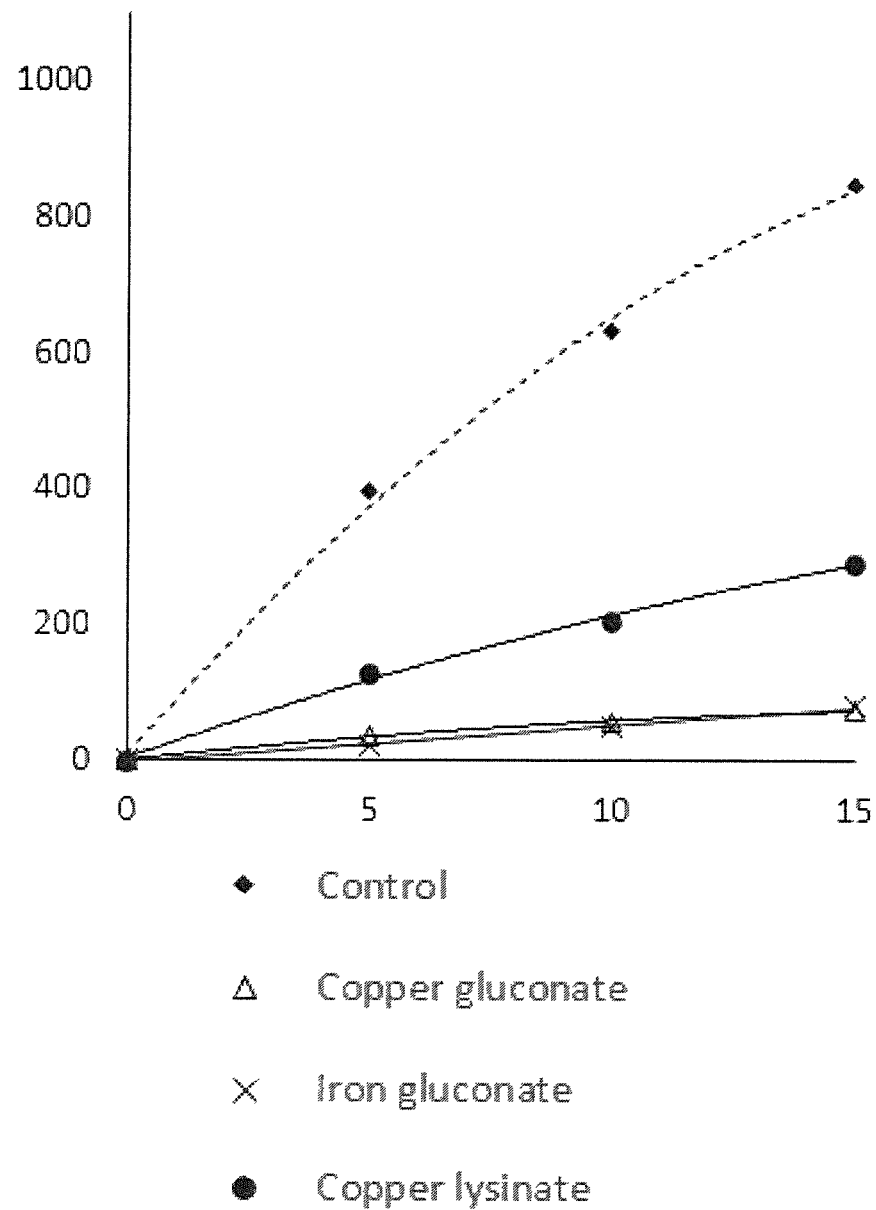

FIG. 11: Trypsin inhibition by copper gluconate, copper lysinate and iron gluconate (see Example 20). The X-axis shows time (minutes), the y-axis shows absorbance at 405 nm.

Figure 12:
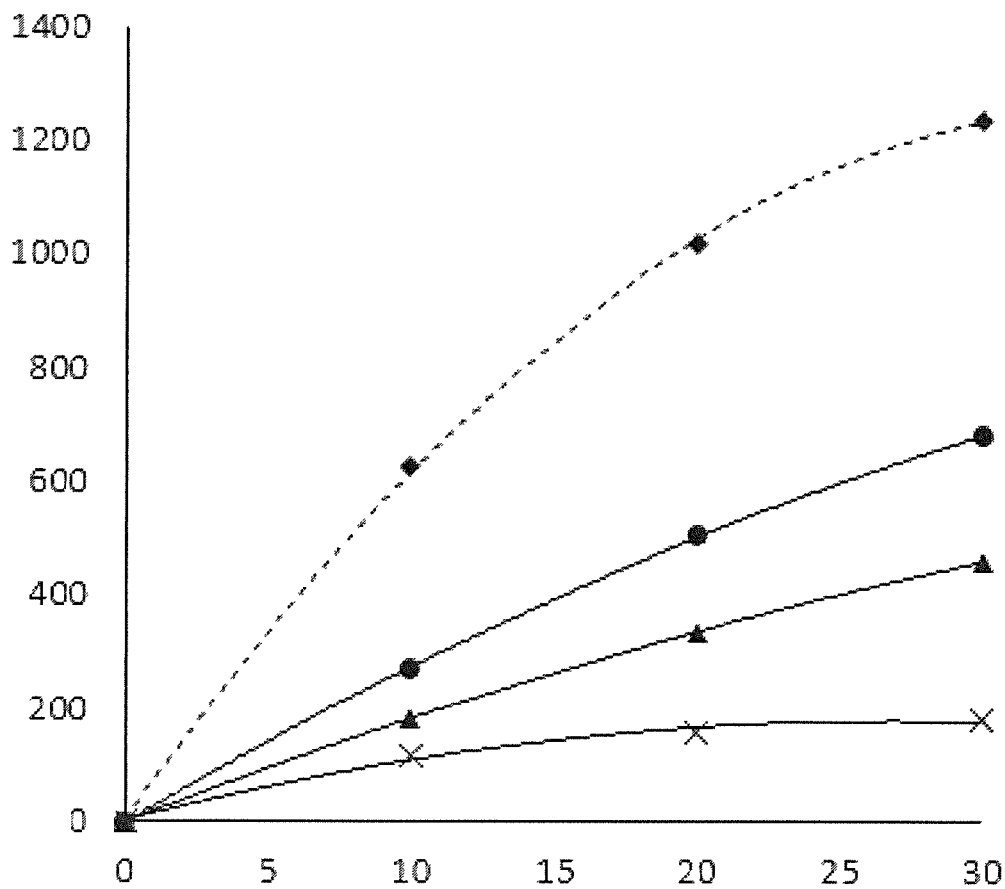

FIG. 12: Trypsin inhibition by copper gluconate, lauryl-glutamate and a combination thereof (see Example 21). The X-axis shows time (minutes), the y-axis shows absorbance at 405 nm.

Figure 13:
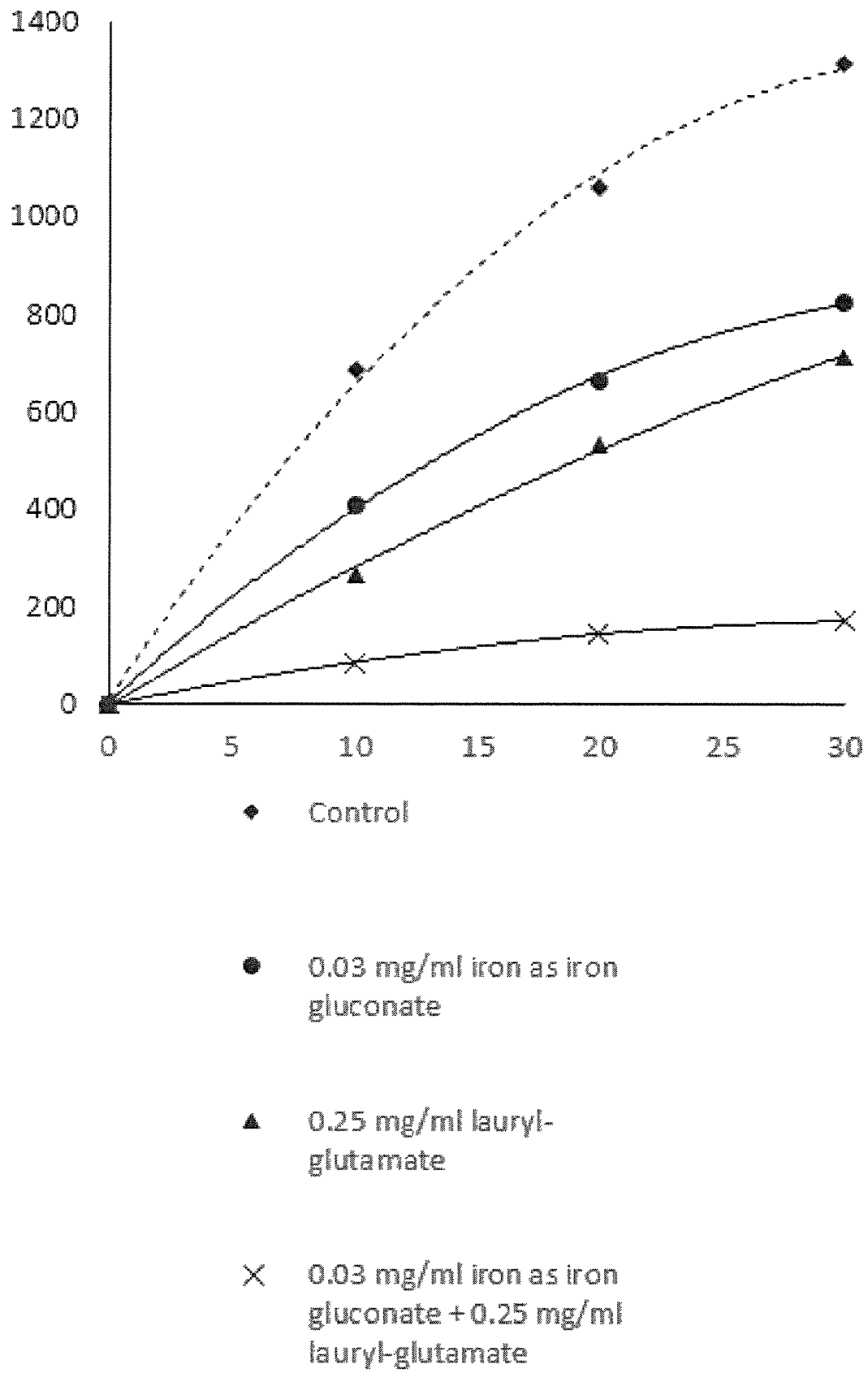

FIG. 13: Trypsin inhibition by iron gluconate, lauryl-glutamate and a combination thereof (see Example 22). The X-axis shows time (minutes), the y-axis shows absorbance at 405 nm.

Figure 14:
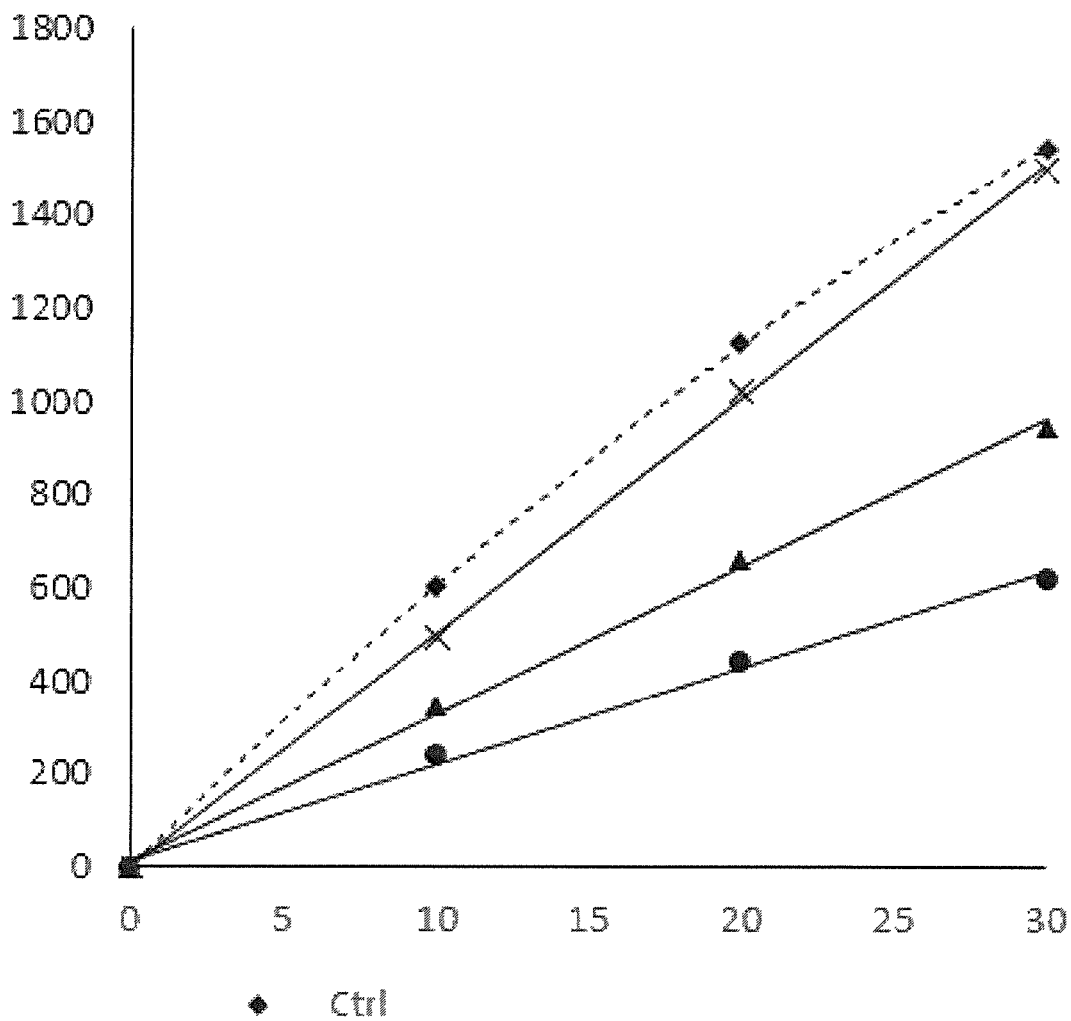

FIG. 14: Chymotrypsin inhibition by copper gluconate, lauryl-glutamate and a combination thereof (see Example 23). The X-axis shows time (minutes), the y-axis shows absorbance at 405 nm.

Figure 15:
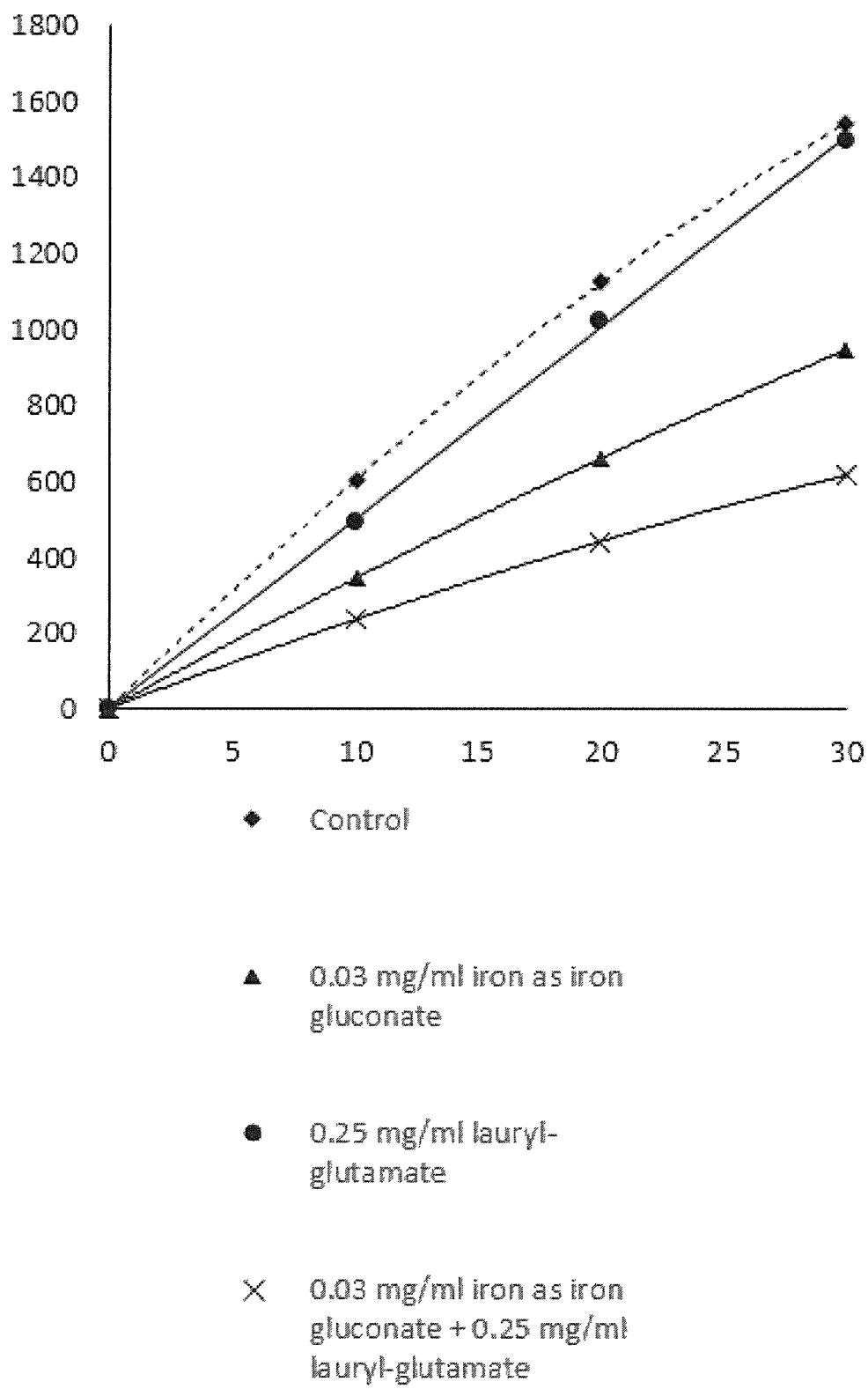

FIG. 15: Chymotrypsin inhibition by iron gluconate, lauryl-glutamate and a combination thereof (see Example 24). The X-axis shows time (minutes), the y-axis shows absorbance at 405 nm.

Figure 16:
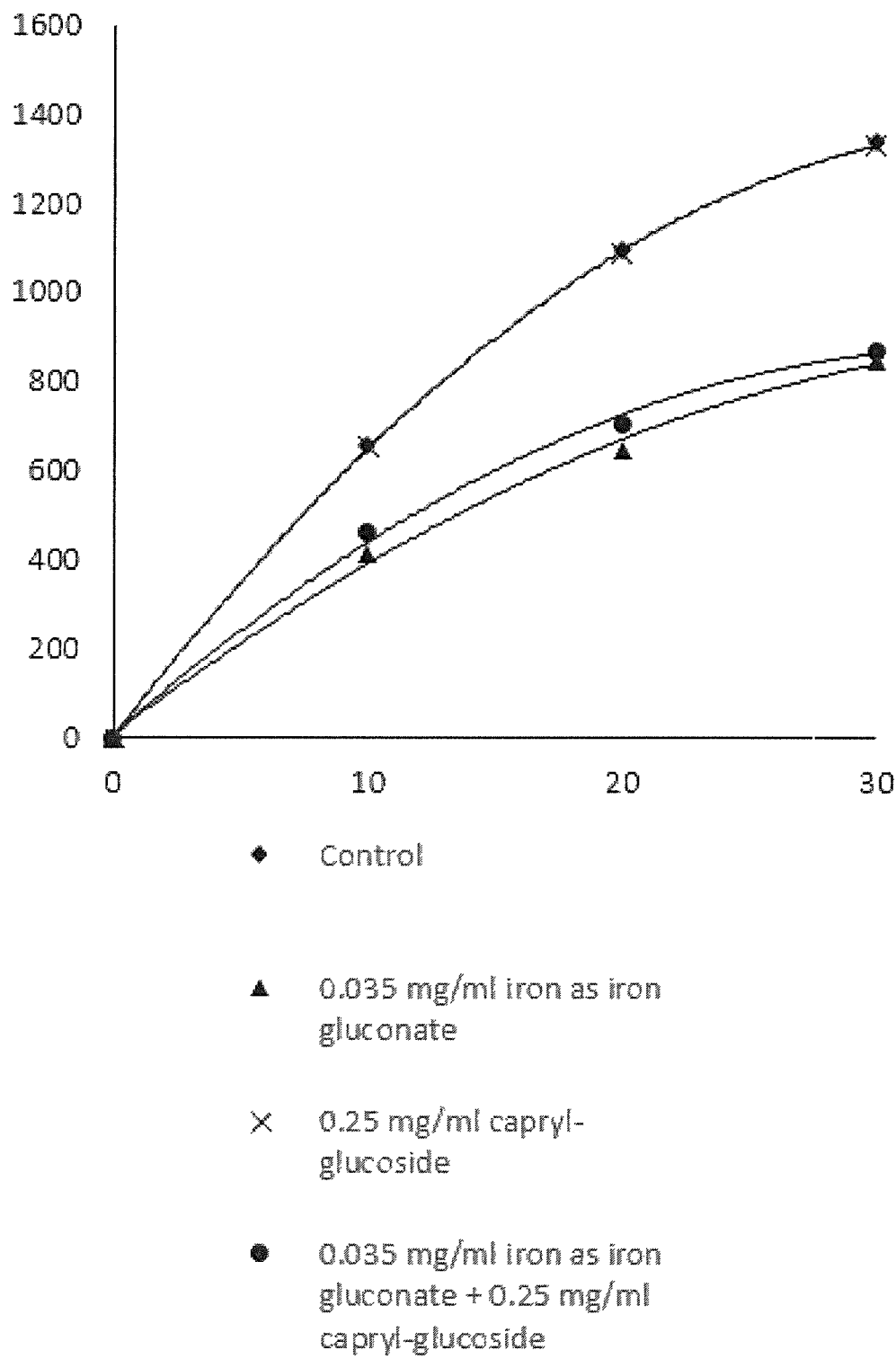

FIG. 16: Trypsin inhibition by iron gluconate, caprylglucoside and a combination thereof (see Example 25). The X-axis shows time (minutes), the y-axis shows absorbance at 405 nm.

Figure 17:
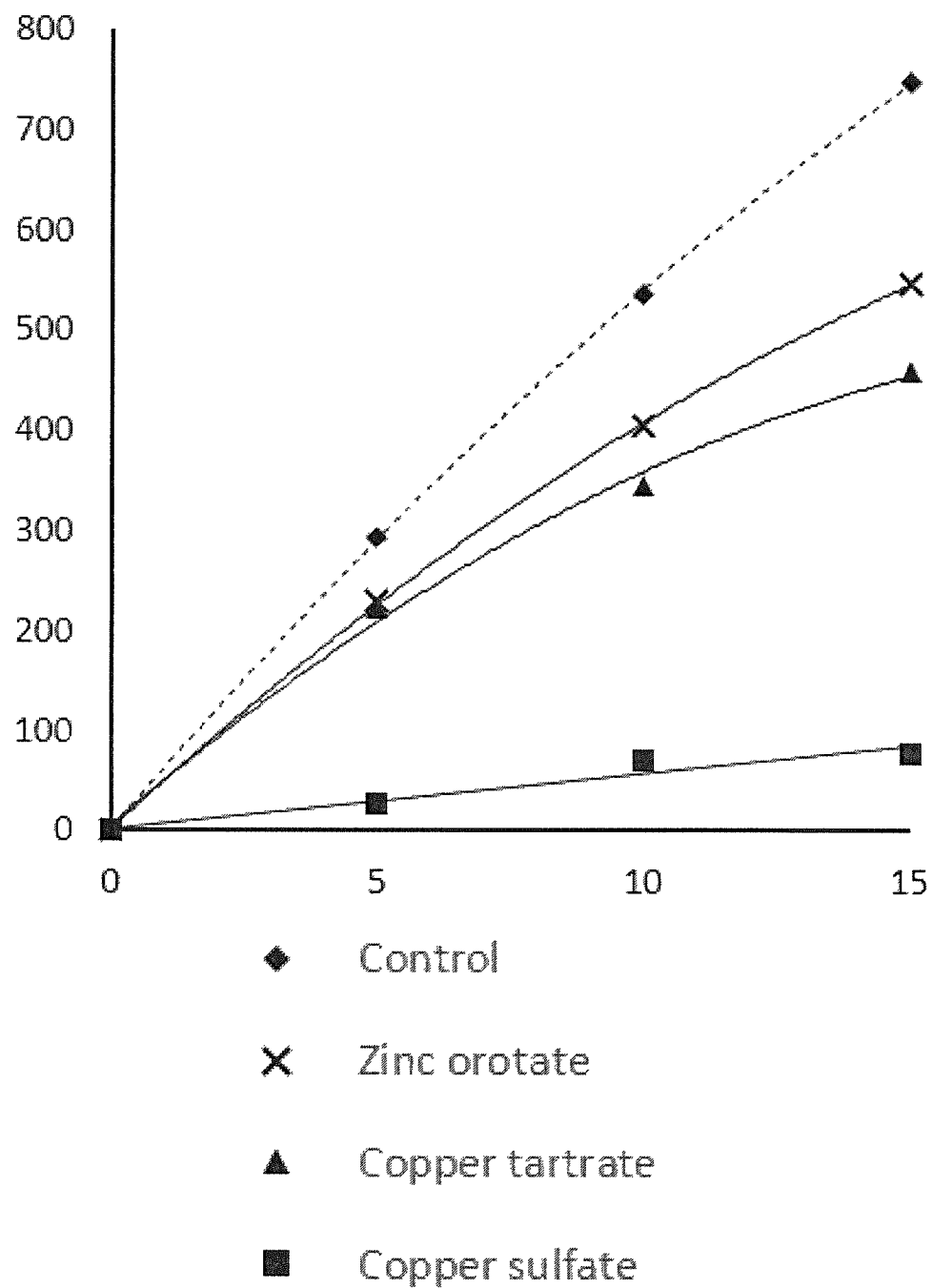

FIG. 17: Trypsin inhibition by copper sulfate, copper tartrate and zinc orotate (see Example 26). The X-axis shows time (minutes), the y-axis shows absorbance at 405 nm.

Figure 18:
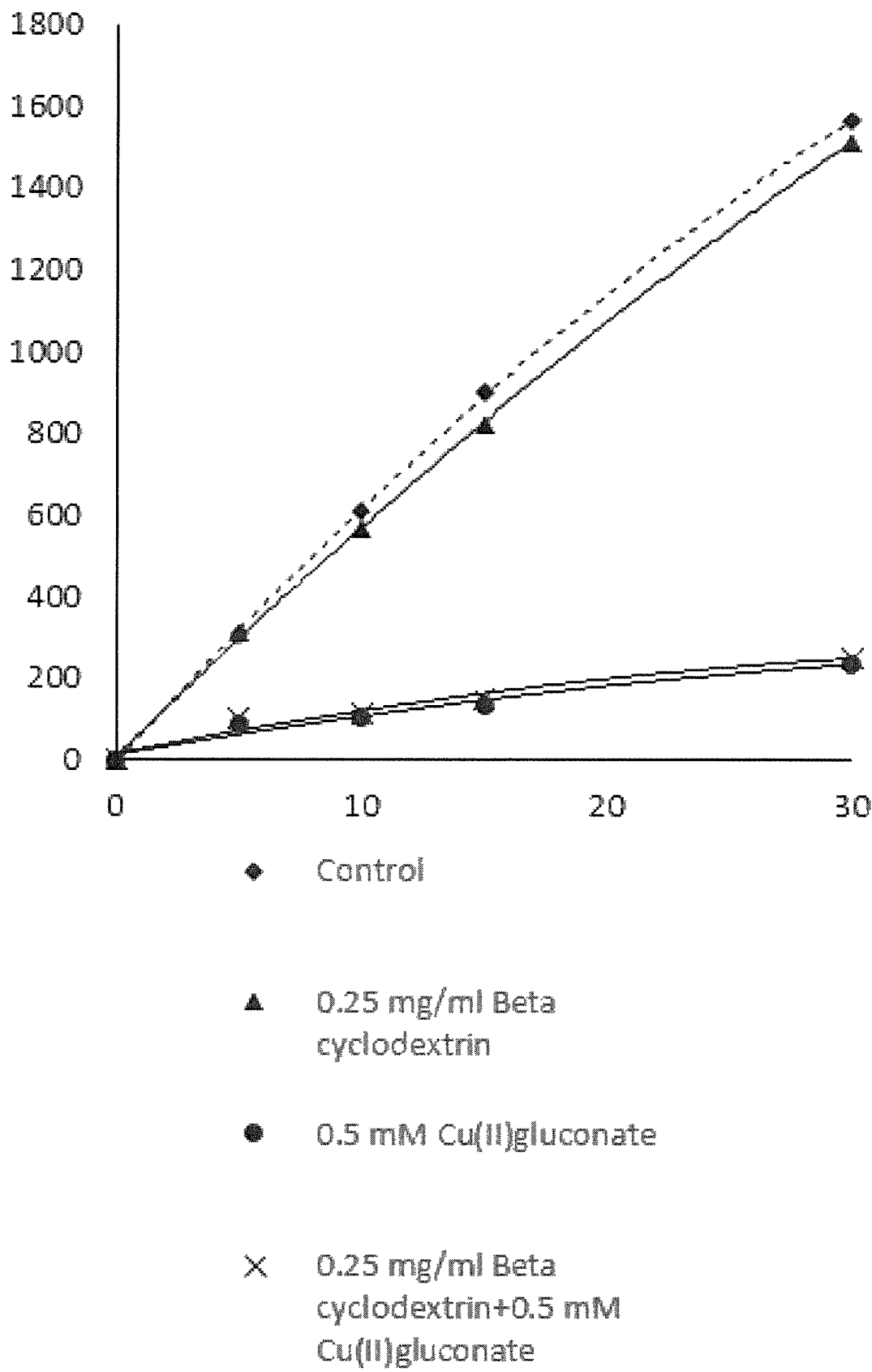

FIG. 18: Chymotrypsin inhibition by copper gluconate, beta-cyclodextrin and a combination thereof (see Example 27). The X-axis shows time (minutes), the y-axis shows absorbance at 405 nm.

Figure 19:
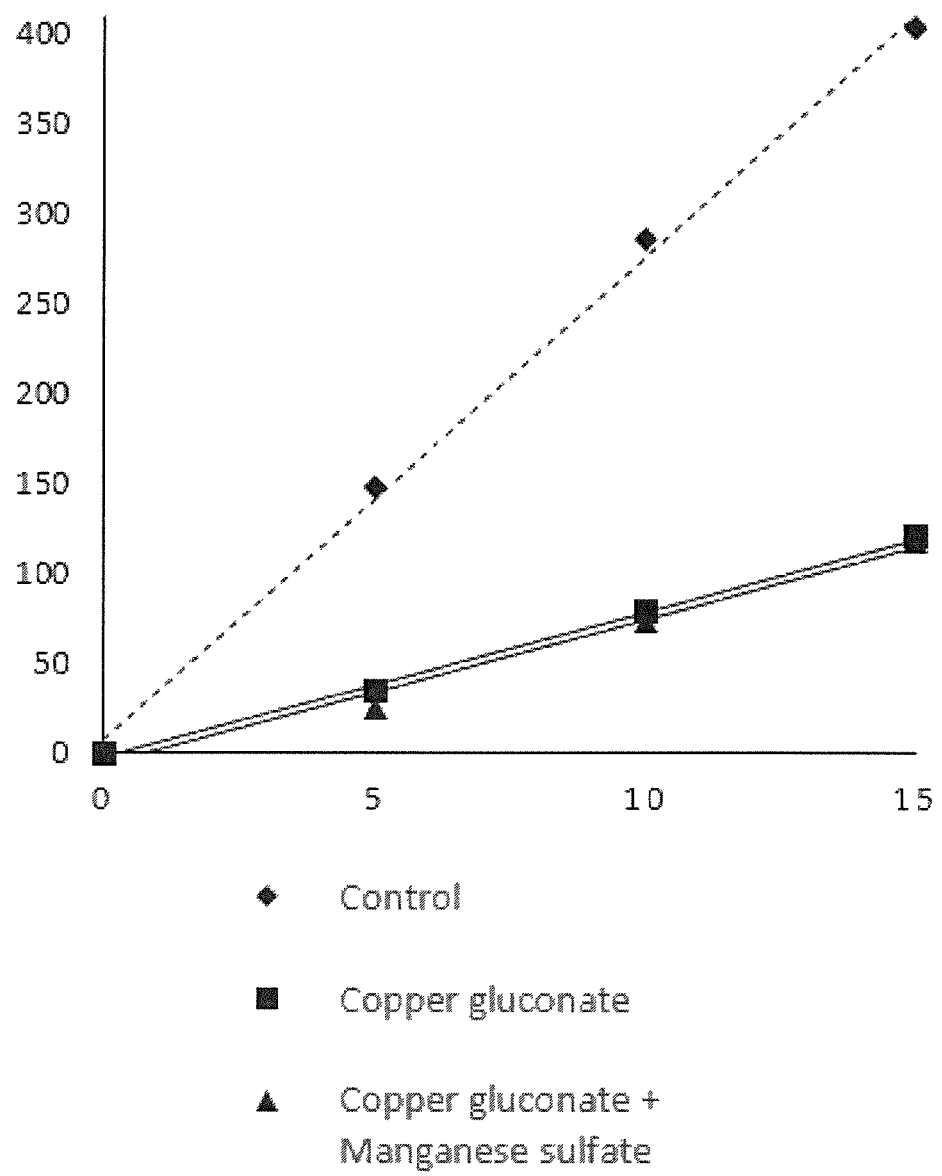

FIG. 19: Trypsin inhibition by copper gluconate and a combination of copper gluconate+ manganese sulfate (see Example 28). The X-axis shows time (minutes), the y-axis shows absorbance at 405 nm.

Figure 20:
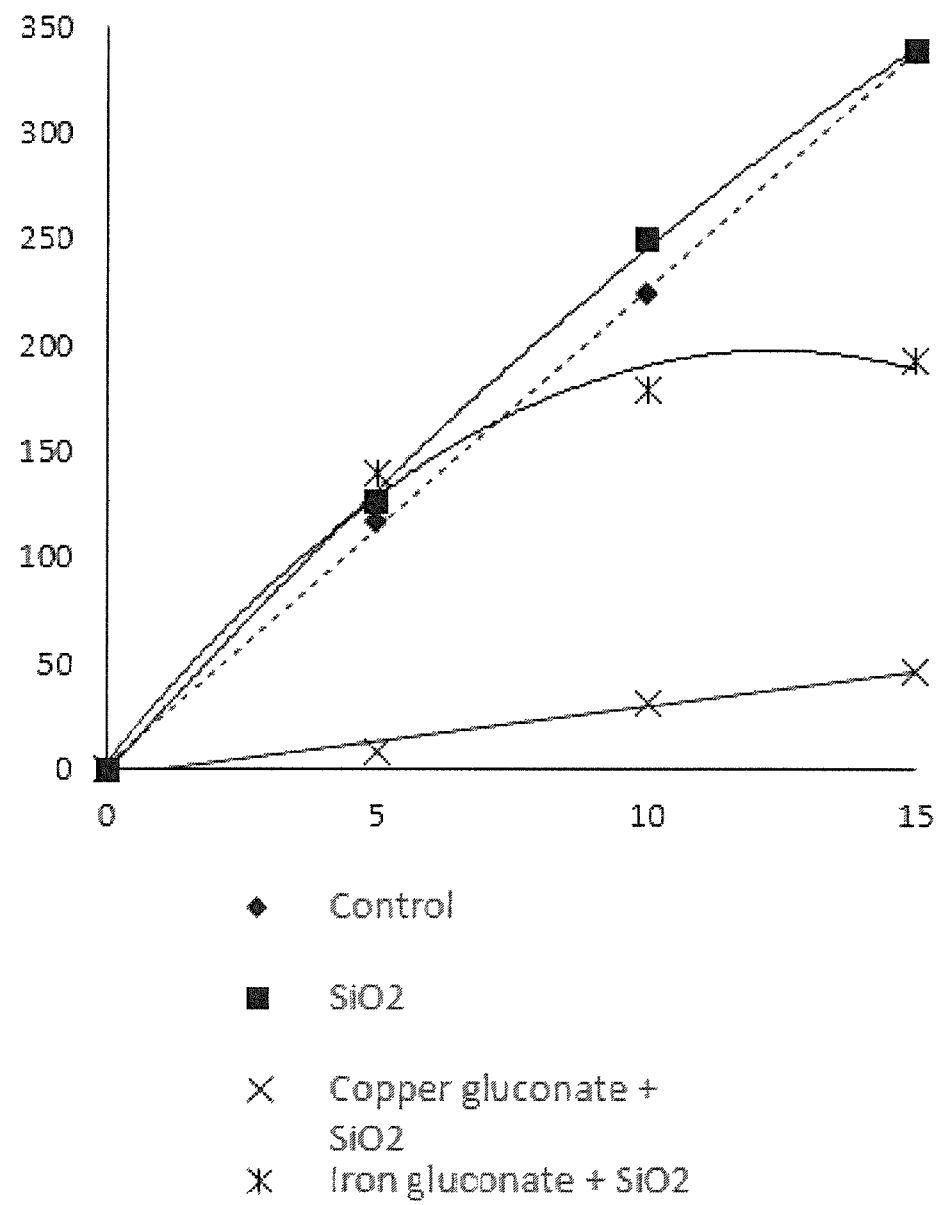

FIG. 20: Trypsin inhibition by combinations of copper gluconate+$SiO_2$ and iron gluconate+ $SiO_2$ (see Example 29). The X-axis shows time (minutes), the y-axis shows absorbance at 405 nm.

Figure 21:
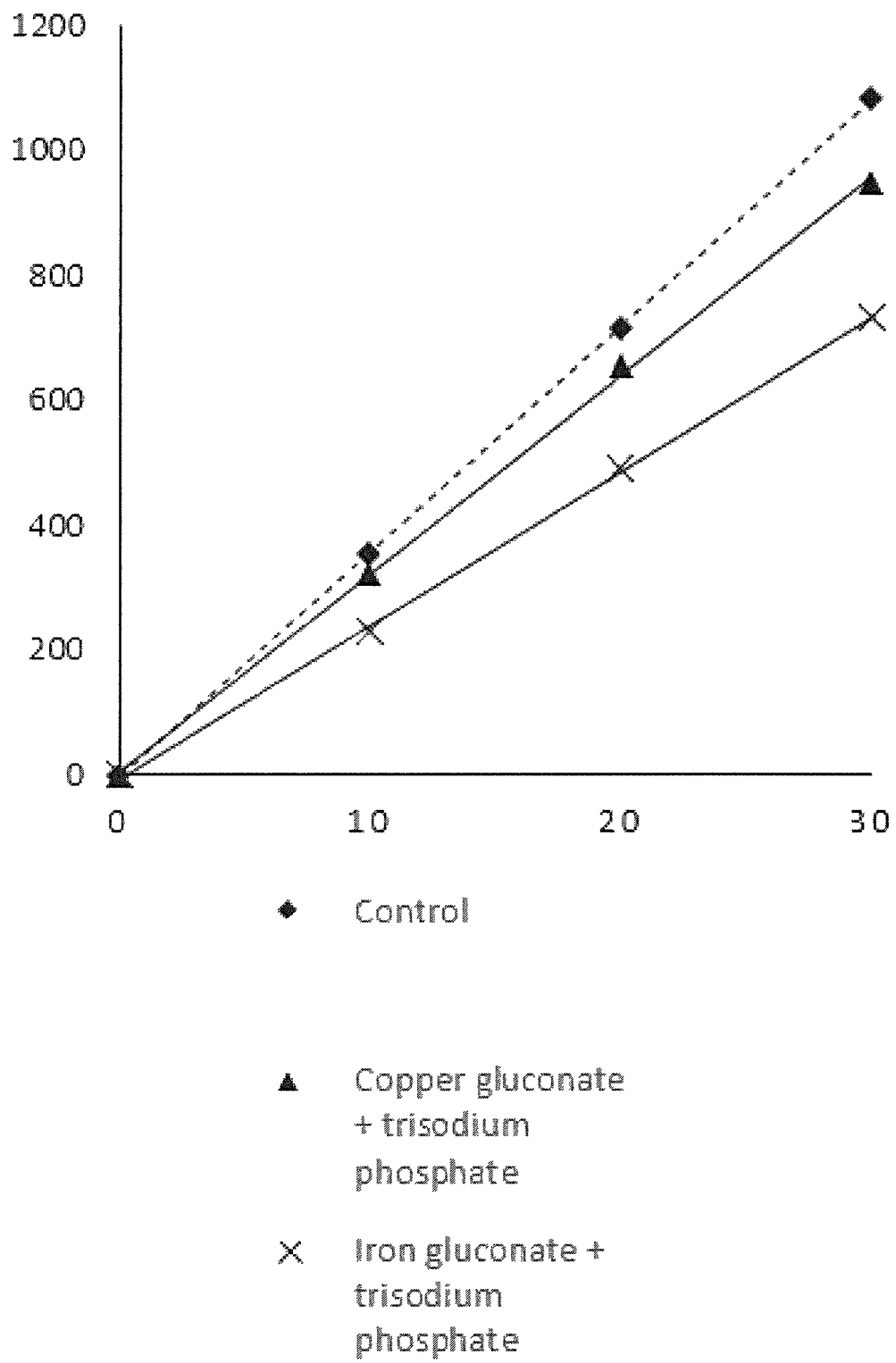

FIG. 21: Chymotrypsin inhibition by combinations of copper gluconate+trisodium phosphate and iron gluconate+ trisodium phosphate (see Example 30). The X-axis shows time (minutes), the y-axis shows absorbance at 405 nm.

Figure 22:
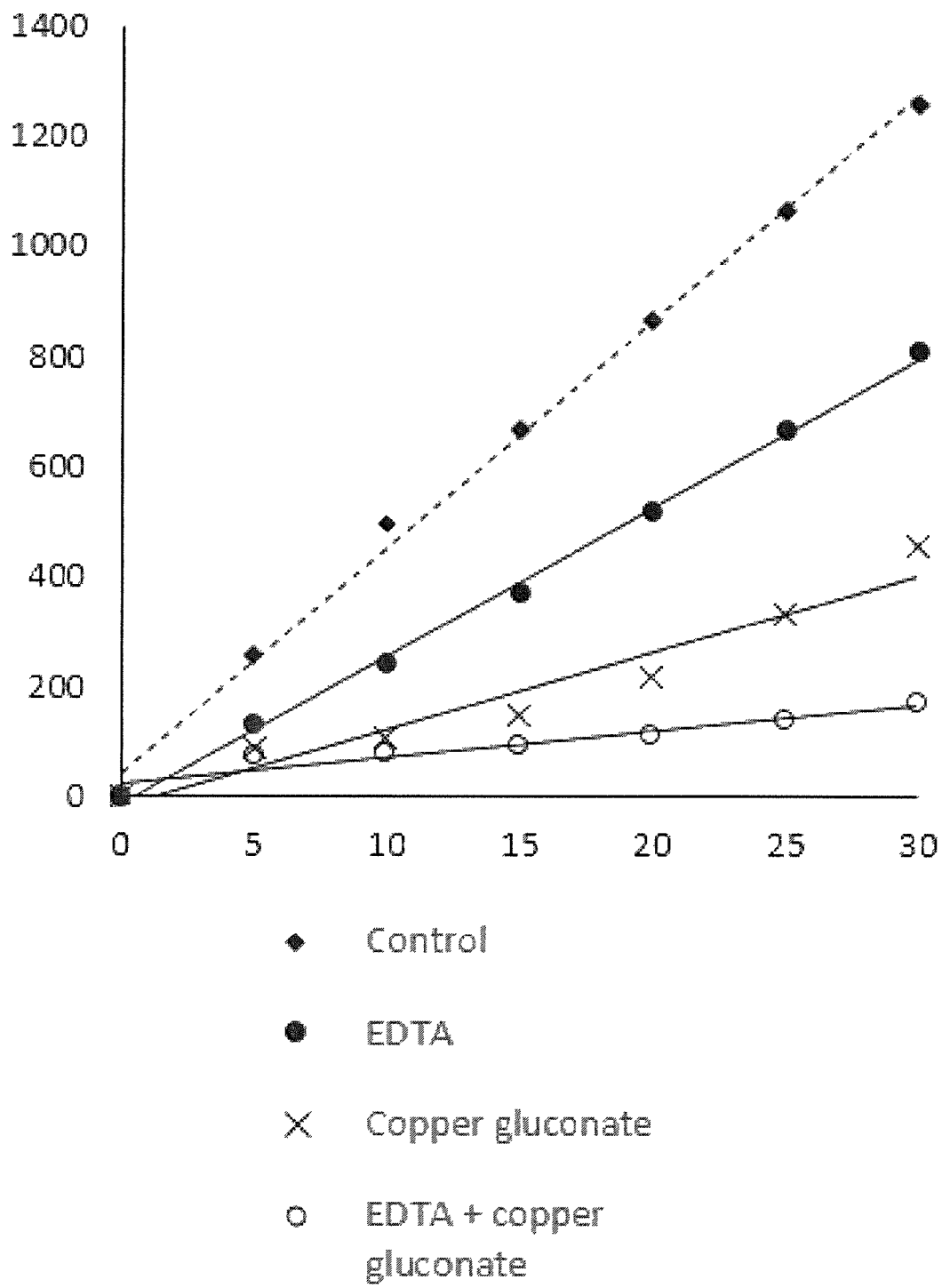

FIG. 22: Chymotrypsin inhibition by copper gluconate, EDTA and a combination thereof (see Example 31). The X-axis shows time (minutes), the y-axis shows absorbance at 405 nm.

Figure 23:
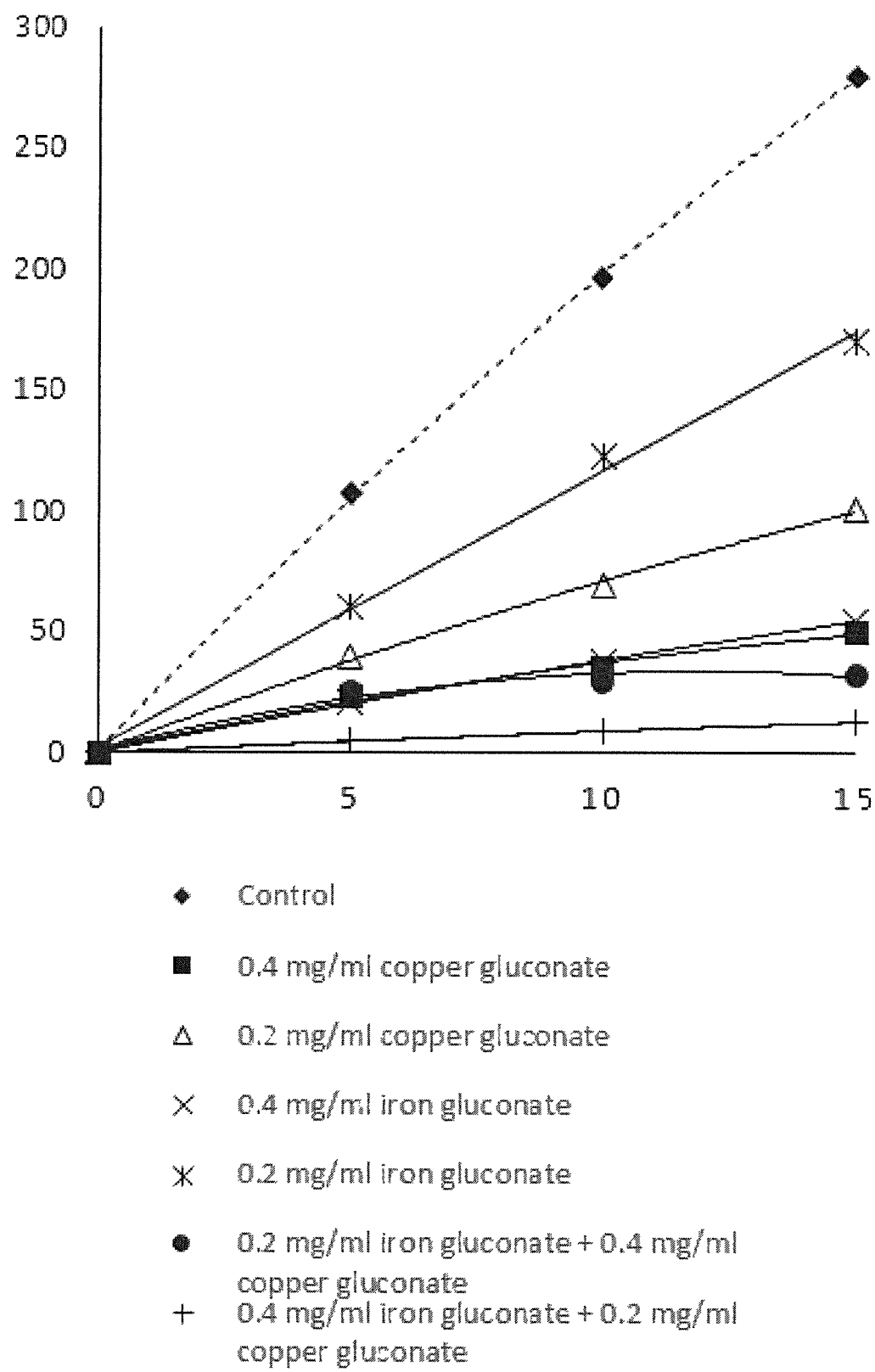

FIG. 23: Trypsin inhibition by copper gluconate, iron gluconate and combinations thereof (see Example 33). The X-axis shows time (minutes), the y-axis shows absorbance at 405 nm.

The invention will now be described by reference to the following examples which are merely illustrative and are not to be construed as a limitation of the scope of the present invention.

EXAMPLES

Example 1

In Vitro Test of the Compatibility of Different Absorption Enhancers with Different Trace Elements Solid dry powder mixtures of desmopressin acetate, zinc sulfate or iron(III) chloride, and different absorption enhancers were prepared and dissolved in 2 ml aqua purificata. Visual examination was performed to observe either a clear solution or visible precipitation. The results of these experiments are summarized in the following table:

| Peptide | Trace element (5 mg/ml) | Absorption enhancer (10 mg/ml) | Dissolution in aqueous medium (2 ml) |
|---|---|---|---|
| Desmopressin | $ZnSO_4$ | Sodium caprate | Precipitation |
| Desmopressin | $ZnSO_4$ | Sodium caprylate | Precipitation |
| Desmopressin | $ZnSO_4$ | Lauroyl sarcosinate | Precipitation |
| Desmopressin | $ZnSO_4$ | Cholic acid | Precipitation |
| Desmopressin | $ZnSO_4$ | Sodium cholate | Precipitation |
| Desmopressin | $ZnSO_4$ | Sodium dodecyl sulfate | Clear solution |
| Desmopressin | $ZnSO_4$ | Lauroyl carnitine HCl | Clear solution |
| Desmopressin | $ZnSO_4$ | Sucrose laurate | Clear solution |
| Desmopressin | $ZnSO_4$ | n-Dodecyl-b-D-maltoside | Clear solution |
| Desmopressin | $ZnSO_4$ | n-Octyl-b-D-glucopyranoside | Clear solution |
| Desmopressin | $ZnSO_4$ | Chitosan | Precipitation |
| Desmopressin | $ZnSO_4$ | Labrasol | Clear solution |
| Desmopressin | $ZnSO_4$ | Citric acid | Clear solution |
| Desmopressin | $FeCl_3$ | Sodium caprate | Precipitation |
| Desmopressin | $FeCl_3$ | Sodium caprylate | Precipitation |
| Desmopressin | $FeCl_3$ | Lauroyl sarcosinate | Precipitation |
| Desmopressin | $FeCl_3$ | Cholic acid | Precipitation |
| Desmopressin | $FeCl_3$ | Sodium cholate | Precipitation |
| Desmopressin | $FeCl_3$ | Sodium dodecyl sulfate | Clear solution |
| Desmopressin | $FeCl_3$ | Lauroyl carnitine HCl | Clear solution |
| Desmopressin | $FeCl_3$ | Sucrose laurate | Clear solution |
| Desmopressin | $FeCl_3$ | n-Dodecyl-b-D-maltoside | Clear solution |
| Desmopressin | $FeCl_3$ | n-Octyl-b-D-glucopyranoside | Clear solution |
| Desmopressin | $FeCl_3$ | Chitosan | Precipitation |
| Desmopressin | $FeCl_3$ | Labrasol | Clear solution |

The term clear solution as used in this table refers to that no clear visible precipitation or flocculation has been observed. The term clear solution also includes slightly colored clear solutions such as yellowish or orange solutions.

These results show that non-ionic and zwitter-ionic absorption enhancers are compatible with di- and trivalent trace elements.

Example 2

Pharmacokinetic Profiles of Liraglutide Formulations after Intestinal Administration to Sprague Dawley Rats Liraglutide formulations comprising a trace element, a complexing agent and an absorption enhancer were dissolved in distilled water and dosed into ileum in volume of 0.4 ml/kg (final concentration 6 mg/ml) to anaesthetized rats. Blood was taken from tail vessels at the time points 0, 30, 60, 90, 120, 180 and 240 min after dosing. The liraglutide plasma concentrations were determined using commercial liraglutide kit (AB Biolabs, USA, cat. number CEK 0130-03). A formulation comprising liraglutide and sodium dodecyl sulfate (SDS) without trace element served as control (LIRA-SDS).

Control:
LIRA-SDS
6 mg/ml Liraglutide
20 mg/ml SDS
Composition:
LIRA001
6 mg/ml Liraglutide
10 mg/ml TRIS
10 mg/ml $ZnSO_4$
20 mg/ml SDS
Composition:
LIRA002
6 mg/ml Liraglutide
5 mg/ml TRIS
40 mg/ml Sodium ascorbate
5 mg/ml $FeCl_3$
20 mg/ml SDS
Composition:
LIRA003
6 mg/ml Liraglutide
1 mg/ml $CuSO_4$
20 mg/ml SDS
Composition:
LIRA004
6 mg/ml Liraglutide
40 mg/ml Mannitol (pharma grade with <0.1% reducing sugar impurities)
5 mg/ml $ZnSO_4$
20 mg/ml SDS
5 mg/ml TRIS The observed pharmacokinetic properties of these compositions are summarized in the following table:

|  | $AUC_{(0-t)}$ (ng/ml × min) | Cmax (ng/ml) | Tmax (min) |
|---|---|---|---|
| LIRA-SDS | 1304 ± 298 | 12 ± 1 | 40-90 |
| LIRA001 | 30720 ± 15848 | 232.8 ± 149.5 | 60-120 |
| LIRA002 | 11796 ± 3192 | 66.5 ± 21.5 | 60-240 |
| LIRA003 | 16575 ± 11291 | 116.4 ± 85.4 | 30-120 |
| LIRA004 | 17430 ± 9124 | 111.9 ± 65.4 | 60-240 |

Moreover, the pharmacokinetic profiles obtained for LIRA001 and LIRA002 as well as LIRA-SDS (control) are illustrated in FIG. 1.

These results show that the addition of a copper salt/complex, a zinc salt/complex or an iron salt/complex to an oral GLP-1 peptide formulation according to the invention improves oral bioavailability up to 23 fold compared to control. The presence of zinc in oral GLP-1 peptide formulations leads surprisingly to high bioavailability.

Example 3

Pharmacokinetic Profiles of PTH(1-34) Formulations after Intestinal Administration to Sprague Dawley Rats Teriparatide (PTH1-34) was dosed subcutaneously in volume of 1 ml/kg (final concentration 0.024 mg/ml teriparatide) to anaesthetized rats. TER001 and TER002 were dosed into ileum in volume of 0.4 mi/kg (final concentration 0.24 mg/ml teriparatide) to anaesthetized rats. Blood was taken from tail vessels at the time points 0, 10, 20, 40, 60, 90, 120 and 180 min after dosing. The teriparatide plasma concentrations were determined using commercial pTH (1-34) human ELISA kit (Biovendor, EU, cat. number RS-1163.0001).

Composition:
TER001
0.38 mg/ml PTH(1-34)
30 mg/ml Lauroylcarnitine HCl
7.5 mg/ml TRIS
5 mg/ml $ZnSO_4$
5 mg/ml Mannitol (pharma grade with <0.1% reducing sugar impurities)
(Final pH=5.3)
Composition:
TER002
0.38 mg/ml PTH(1-34)
30 mg/ml Lauroylcarnitine HCl
30 mg/ml TRIS
5 mg/ml $ZnSO_4$
5 mg/ml Mannitol (pharma grade with <0.1% reducing sugar impurities)
(Final pH=8.3)

The observed pharmacokinetic properties of these compositions are summarized in the following table:

|  | $AUC_{(0-t)}$ (ng/ml × min) | Cmax (ng/ml) | Tmax (min) | F (%) | Half-life (min) |
|---|---|---|---|---|---|
| PTH (1-34) s.c. | 136 ± 32 | 2.8 ± 0.8 | 10 | 100 ± 23 | 44 ± 8 |
| TER001 | 94 ± 38 | 1.1 ± 0.4 | 10-90 | 11 ± 4 | 86 ± 13 |
| TER002 | 82 ± 29 | 1.1 ± 0.4 | 10-40 | 10 ± 3 | 66 ± 1 |

Compositions according to the invention comprising PTH (1-34), an absorption enhancer, the trace element zinc and a complexing agent thus resulted in significant oral bioavailability and sustained pharmacokinetic profile as shown by increasing half life.

Example 4

GLP-1 Peptide Formulations with SNAC and Trace Elements

Compositions comprising a GLP-1 peptide, a complexing agent (disodium phosphate dihydrate), the absorption enhancer N-(8-[2-hydroxybenzoyl]amino)caprylic acid (SNAC) and various trace elements or metal salts were prepared and dissolved in 2 ml of aqua purificata and examined visually. The results of these experiments are summarized in the following table:

| GLP-1 peptide 1.8 mg/ml | Absorption enhancer (20 mg) | Trace element (2 mg) | Dissolution in aqua purificata |
|---|---|---|---|
| Liraglutide | SNAC | ZnSO$_4$ | precipitation |
| Liraglutide | SNAC | Zinc acetate | precipitation |
| Liraglutide | SNAC | ZnCl$_2$ | precipitation |
| Liraglutide | SNAC | Zinc orotate | Clear solution |
| Liraglutide | SNAC | Zinc picolinate | Clear solution |
| Liraglutide | SNAC | Zinc carnosine | Clear solution |
| Liraglutide | SNAC | CuSO$_4$ | precipitation |
| Liraglutide | SNAC | Copper gluconate | Clear yellowish solution |
| Liraglutide | SNAC | Copper orotate | Clear solution |
| Liraglutide | SNAC | Fe(III)chlorid | precipitation |
| Liraglutide | SNAC | Ferrous gluconate | Clear orange solution |
| Liraglutide | SNAC | Iron bisglycinate | Clear brownish solution |

These results show a good compatibility with regard to solubility of SNAC with trace elements comprising an organic salt whereas inorganic salts result in precipitations.

Example 5

Pharmacokinetic Profiles of Liraglutide after Intestinal Administration to Sprague Dawley Rats The liraglutide formulations were dosed into ileum in volume of 0.4 ml/kg (final concentration of 6 mg/ml) to anaesthetized rats. The anaesthesia was induced with Hypnorm/Dormicum mixture. After checking of the depth of anaesthesia the animal was placed on its back and a 3-5 cm long midline incision was made in the skin of abdomen.

The caecum was exposed and the distal segment of small intestine was pulled out of the abdominal cavity and the position of the spot convenient for introduction of catheter was measured using a PE tubing with mark at a distance of 5 cm. The intestine was penetrated by the catheter tip and the catheter was inserted downstream into the ileum lumen at a distance of 5 cm from caecum in a spot without feces, outside the area with accumulated lymphatic tissue and outside the blood vessels and fixed with ligature.

The pulled segment of small intestine was replaced into the abdominal cavity, 2 ml of sterile saline were flushed over the intestine and the abdominal cavity was closed with metal wound clips in two layers. Blood was taken from tail vessels at the time points 0, 30, 60, 120, 180 and 240 min after dosing. The liraglutide plasma concentrations were determined using commercial liraglutide kit (AB Biolabs, USA, cat.number CEK 0130-03). The results are summarized in the table further below.
Reference Formulation
6 mg/ml Liraglutide
50 mg/ml SNAC
LIRA026
6 mg/ml Liraglutide
50 mg/ml SNAC
35 mg Polysorbate 20
1.9 mg/ml Copper(II)orotate
1.9 mg/ml Mannitol
LIRA027
6 mg/ml Liraglutide
50 mg/ml SNAC
35 mg Polysorbate 20
2.0 mg/ml Copper(II)glycinate
2.0 mg/ml Mannitol
LIRA029
6 mg/ml Liraglutide
50 mg/ml SNAG
35 mg Polysorbate 20
4.0 mg/ml Zinc(II)orotate
4.0 mg/ml Mannitol
LIRA033
6 mg/ml Liraglutide
50 mg/ml SNAC
35 mg Polysorbate 20
3.5 mg/ml Zinc(II)picolinate
3.5 mg/ml Mannitol
Results:

| Formulation | $\Delta AUC_{(0-180)}$ (ng/ml × min) | Cmax (ng/ml) | Tmax (min) | Improvement ratio |
|---|---|---|---|---|
| Reference | 4907 ± 2921 | 40.5 ± 14.4 | 60-120 | — |
| LIRA026 | 14276 ± 8207 | 85.3 ± 41.2 | 60-180 | 2.9-fold |
| LIRA027 | 19627 ± 15401 | 123.5 ± 87.8 | 30-120 | 4.0-fold |
| LIRA029 | 5717 ± 3207 | 43.0 ± 18.7 | 60-240 | 1.2-fold |
| LIRA033 | 10511 ± 4980 | 71.3 ± 27.5 | 30-120 | 2.1-fold |

These results show that the compositions according to the present invention, containing a peptide drug such as liraglutide in combination with a copper or zinc salt/complex and a complexing agent, exhibit an advantageously increased oral bioavailablity.

Example 6

Pharmacokinetic Profiles of Liraglutide after Oral Administration to Beagle Dogs Hard capsules comprising liraglutide (10 mg/dog) were dosed orally directly on the root of the tongue. Administered capsule was washed down by 3 ml of water via a syringe to ensure that the drug is correctly swallowed and to ensure complete oesophageal clearance. Blood was taken by venepuncture from v. cephalics antebrachii at the time points 0, 15, 30, 60, 90, 120 and 180 min before and after oral dosing.

2 ml of blood were sampled into Greiner Bio-one tubes containing K3EDTA (Greiner, Austria). Blood samples were centrifuged (10 min, 3500 rpm, 4° C.) and approximately 600 μl of plasma were collected. The liraglutide plasma concentrations are determined using commercial liraglutide EIA kit (Peninsula Laboratories International, USA, cat. number S-1502.0001). The formulation LIRA042 exhibited the best pharmacokinetic profile. The liraglutide plasma concentrations reaching 10-15 ng/ml appeared 60 min after dosing and persisted up to the end of the study. The PK data is summarized in the table further below.
Reference Formulation
HPMC capsule
10 mg Liraglutide
200 mg SNAG
LIRA042
HPMC capsule
10 mg Liraglutide
200 mg SNAC
200 mg Sorbitol
1 mg Copper(II)glycinate
19 mg Mannitol
LIRA043
HPMC capsule 10 mg Liraglutide
200 mg SNAC
200 mg Sodium citrate
1 mg Copper(II)glycinate
19 mg Mannitol
LIRA045
HPMC capsule
10 mg Liraglutide
200 mg SNAC
100 mg TRIS
100 mg Polysorbate 20
2 mg Copper(II)glycinate
38 mg Mannitol
LIRA046
HPMC capsule
10 mg Liraglutide
200 mg SNAC
100 mg TRIS
100 mg Polysorbate 20
5 mg Copper(II)glycinate
95 mg Mannitol
LIRA047
HPMC capsule
10 mg Liraglutide
200 mg SNAC
100 mg TRIS
100 mg Polysorbate 20
10 mg Copper(II)glycinate
190 mg Mannitol
LIRA048
HPMC capsule
10 mg Liraglutide
200 mg SNAC
100 mg TRIS
100 mg Polysorbate 20
10 mg Zinc(II)picolinate PK-Profile of Liraglutide after Oral Administration to Beagle Dogs:

| Formulation | $\Delta AUC_{(0-180)}$ (ng/ml × min) | Cmax (ng/ml) | Tmax (min) | Improvement ratio |
|---|---|---|---|---|
| Reference (n = 2) | 46.5 | 1.1 | 60 | — |
| LIRA042 | 1866 | 16.7 | 90 | 40-fold |
| LIRA043 | 167 | 2.3 | 90 | 3.6-fold |
| LIRA045 | 167 | 3.0 | 60 | 3.6-fold |
| LIRA046 | 90 | 2.8 | 180 | 1.9-fold |
| LIRA047 | 341 | 4.1 | 120 | 7.3-fold |
| LIRA048 | 147 | 4.9 | 180 | 3.2-fold |

These results demonstrate that compositions according to the invention comprising a copper or zinc salt/complex, a complexing agent and SNAC show several fold improved absorption of a GLP-1 peptide (liraglutide) after oral administration in comparison with SNAG alone.

Example 7

In Vivo Study in Non-Human Primates with Oral PTH(1-34) Formulations

Capsule formulations comprising PTH(1-34) were dosed orally to female Cynomolgus macaques (*Macaca fascicularis*) with a body weight of 4 to 5 kg. Blood collection for PTH(1-34) analysis was performed at the time points: 1 time pre-dose (0 min), 15 min, 30 min, 60 min, 90 min, 120 min, 180 min and 240 min post-dose with heparinized syringe. Each sample is collected from a peripheral vein. After each tube of blood is drawn, it is inverted gently several times to ensure the mixing of anticoagulant. The sample is centrifuged at between 3-5° C. for 10 minutes at 3,000 g. The teriparatide plasma concentrations are determined using commercial high sensitivity teriparatide ELISA kit (Immutopics Inc., USA, cat.number 60-3900).

Reference Formulation
HPMC capsule
2.5 mg PTH(1-34)
100 mg SNAC
TER071
HPMC capsule
2.5 mg PTH(1-34)
0.5 mg Copper(II)orotate
9.5 mg Mannitol
100 mg TRIS
100 mg SNAC
TER073
HPMC capsule
2.5 mg PTH(1-34)
1 mg Copper(II)orotate
19 mg Mannitol
100 mg TRIS
100 mg SNAC
TER075
HPMC capsule
2.5 mg PTH(1-34)
1 mg Copper(II)orotate
19 mg Mannitol
100 mg Choline chloride
100 mg SNAC
TER077
HPMC capsule
2.5 mg PTH(1-34)
1 mg Copper(II)glycinate
19 mg Mannitol
100 mg Choline chloride
100 mg SNAC
TER084
HPMC capsule
2.5 mg PTH(1-34)
3 mg Copper(II)glycinate
27 mg Mannitol
200 mg Choline chloride
200 mg SNAC

| Formulation | AUC | Improvement ratio |
|---|---|---|
| Reference formulation (n = 4) | 18725 | — |
| TER071 (n = 3) | 43256 | 2.3-fold |
| TER073 (n = 1) | 70650 | 3.8-fold |
| TER075 (n = 1) | 45975 | 2.5-fold |
| TER077 (n = 1) | 42547 | 2.3-fold |
| TER084 (n = 1) | 65250 | 3.5-fold |

These results show that the compositions according to the present invention, particularly compositions containing a peptide drug such as teriparatide (PTH(1-34)) in combination with a copper salt/complex and a complexing agent, exhibit a considerably increased absorption and, thus, an improved oral bioavailablity.

Example 8

Pharmacokinetic Profile of Octreotide Formulations after Administration into Proximal Jejunum of Sprague Dawley Rats The formulations OCT002, OCT003 and OCT004 were dissolved in an octreotide stock solution 5-10 min prior to dosing into proximal jejunum in volume of 0.4 ml/kg to anaesthetized rats. The final octreotide concentration of each formulation was 0.36 mg/kg. Blood was taken from tail vessels at the time points 0, 10, 20, 40, 60, 90 and 120 min after dosing. The octreotide plasma concentration was determined using commercial octreotide kit (Peninsula Laboratories International, Inc., USA, cat.number S-1342.0001).

OCT002
0.89 mg/ml Octreotide
50 mg/ml SNAC
50 mg/ml Polysorbate 20
2.5 mg/ml Copper(II)bisglycinate
2.5 mg/ml Sorbitol OCT003
0.89 mg/ml Octreotide
100 mg/ml Sucrose laurate
2.5 mg/ml Copper(II)bisglycinate
2.5 mg/ml $CuSO_4$ penta hydrate
5 mg/ml Sorbitol OCT004
0.89 mg/ml Octreotide
100 mg/ml SMEDDS (50 mg/ml Labrasol, 40 mg/ml Polysorbate 20 and 10 mg/ml Glycerol)
2.5 mg/ml Copper(II)bisglycinate
2.5 mg/ml $CuSO_4$ penta hydrate Results:

The formulation OCT004 had the best pharmacokinetic profile with mean Cmax 6.1 ng/ml and relative biovailability of 9.3%, while the formulation OCT003 reached relative bioavailability of 7.7% and Cmax of 4.5 ng/ml. The effect of the formulation OCT002 was lower with the relative bioavailability of 2.2%. All formulations showed low variability of pharmacokinetic parameters. The octreotide data are summarized in the following table:

PK Profile of Octreotide Formulations:

|  | $\Delta AUC_{(0-120)}$ (ng/ml × min) | Cmax (ng/ml) | Tmax (min) | F (%) |
|---|---|---|---|---|
| Reference (s.c.) | 14126 ± 2727 | 148 ± 36 | 90 | 100 ± 19 |
| OCT002 | 106 ± 65 | 1.2 ± 0.6 | 20-40 | 2.2 ± 1.3 |
| OCT003 | 389 ± 63 | 4.5 ± 0.7 | 10-20 | 7.7 ± 1.2 |
| OCT004 | 472 ± 77 | 6.1 ± 1.2 | 10-40 | 9.3 ± 1.5 |

It has thus been demonstrated that compositions comprising a peptide drug, the trace element copper, at least one polyol as complexing agent and further comprising a permeation enhancer such as a SMEDDS formulation or a classical permeation enhancer resulted in robust oral bioavailability with low variability relative to subcutanous administration.

Example 9

Concentration Dependent Inhibition of Chymotrypsin by Copper(II)Sulfate

Stock Solutions:
$CuSO_4.5H_2O$ dilutions in 10 mM TRIS buffer pH 7 to 10 mM, 5 mM, 2.5 mM 1.25 mM Benzoyl-Tyrosine p-nitroanilide (BTPNA): 0.5 mg/mL BTPNA in Acetone Study:
(1) 100 µl buffer (10 mM TRIS, pH=7)+50 µl Chymotrypsin Stock+50 µl BTPNA
(2) 80 µl buffer (10 mM TRIS, pH=7)+20 µl $CuSO_4$ stock (10 mM)+50 µl Chymotrypsin Stock+50 µl BTPNA
(3) 80 µl buffer (10 mM TRIS, pH=7)+20 µl $CuSO_4$ dilut. (5 mM)+50 µl Chymotrypsin Stock+50 µl BTPNA
(4) 80 µl buffer (10 mM TRIS, pH=7)+20 µl $CuSO_4$ stock (2.5 mM)+50 µl Chymotrypsin Stock+50 µl BTPNA
(5) 80 µl buffer (10 mM TRIS, pH=7)+20 µl $CuSO_4$ dilut. (1.25 mM)+50 µl Chymotrypsin Stock+50 µl BTPNA Final copper concentrations: 1 mM, 0.5 mM, 0.25 mM, 0.125 mM.

Absorption was measured directly at 405 nm.
Values were corrected (subtraction of blank).

Results:
Copper sulfate inhibits the proteolytic enzyme chymotrypsin in a dose dependent manner (see also FIG. 2).

Example 10

Concentration Dependent Inhibition of Trypsin by Copper(II)Gluconate

Stock Solutions:
100 mg/ml copper gluconate in 50 mM TRIS pH 7; pH was adjusted to pH 7; stock solution was diluted to the following concentrations: 50 mg/ml, 25 mg/ml, 12.5 mg/ml, 5 mg/ml, 6.25 mg/ml, 3.125 mg/ml, 2.5 mg/ml, 1.25 mg/ml, 0.625 mg/ml, 0.313 mg/ml, 0.156 mg/ml and 0.078 mg/ml
0.1 mg/ml Trypsin
0.5 mg/mL Benzoyl-Arginine p-nitroanilide (BAPNA)

Study:
100 µl 50 mM TRIS pH 7+50 µL Trypsin Stock+50 µL BAPNA Stock
100 µl Copper solution (according to the above described dilutions)+50 µL Trypsin Stock+50 µL BAPNA Stock
Absorption was measured after 15 minutes at 405 nm.
Values were corrected (subtraction of blank).

Results:
Copper gluconate inhibits the proteolytic enzyme trypsin in a dose dependent manner (see FIG. 3).

Example 11

Concentration Dependent Inhibition of Trypsin by Zinc(II)Bisglycinate

Stock Solutions:
100 mg/ml Zinc bisglycinate in 50 mM TRIS pH 7; pH was adjusted to pH 7; stock solution was diluted to the following concentrations: 50 mg/ml and 25 mg/ml
0.1 mg/ml Trypsin
0.5 mg/mL Benzoyl-Arginine p-nitroanilide (BAPNA)

Study:

100 µl 50 mM TRIS pH 7+50 µL Trypsin Stock+50 µL BAPNA Stock

100 µl Zinc solution (according to the above described dilutions)+50 µL Trypsin Stock+50 µL BAPNA Stock Absorption was measured after 15 minutes at 405 nm.

Values were corrected (subtraction of blank).

Results:

In high concentrations, zinc bisglycinate inhibits the proteolytic enzyme trypsin in a dose dependent manner (see also FIG. 4).

Example 12

Concentration Dependent Inhibition of Trypsin by Iron(II)Gluconate

Stock Solutions:

10 mg/ml iron gluconate in 50 mM TRIS pH 7; pH was adjusted to pH 7; stock solution was diluted to the following concentrations: 5 mg/ml, 2.5 mg/ml, 1.25 mg/ml and 0.625 mg/ml 0.1 mg/ml Trypsin 0.5 mg/mL Benzoyl-Arginine p-nitroanilide (BAPNA)

Study:

100 µl 50 mM TRIS pH 7+50 µL Trypsin Stock+50 µL BAPNA Stock

100 µl Iron solution (according to the above described dilutions)+50 µL Trypsin Stock+50 µL BAPNA Stock Absorption was measured directly at 405 nm.

Values were corrected (subtraction of blank).

Results:

Iron gluconate inhibits the proteolytic enzyme trypsin in a dose dependent manner (see FIG. 5).

Example 13

Inhibition of Chymotrypsin by 3 Different Copper Salts

Stock Solutions:

10 mM $CuSO_4$ and Copper gluconate stock solution were diluted 1:1 with 10 mM TRIS buffer pH 7

Benzoyl-Tyrosine p-nitroanilide (BTPNA): 0.5 mg/mL BTPNA in Acetone

Study:

(1) 100 µl buffer (10 mM TRIS, pH=7)+50 µl Chymotrypsin Stock+50 µl BTPNA (2) 80 µl buffer (10 mM TRIS, pH=7)+20 µl $CuSO_4$ dil. (5 mM)+50 µl Chymotrypsin Stock+50 µl BTPNA (3) 80 µl buffer (10 mM TRIS, pH=7)+20 µl Copper gluconate dilut. (5 mM)+50 µl Chymotrypsin Stock+50 µl BTPNA (4) 100 µl Cu-bisglycinate stock (0.5 mM)+50 µl Chymotrypsin Stock+50 µl BTPNA Final copper concentrations: 0.5 mM ($CuSO_4$ and copper gluconate), 0.25 mM copper bisglycinate Values were corrected (subtraction of blank)

Results:

Three different copper salts were tested and all showed similar inhibition profiles of chymotrypsin (see FIG. 6).

Example 14

Influence of Copper Pre-Incubation on Chymotrypsin Activity

Stock Solutions:

10 mM $CuSO_4$ stock solution was diluted 1:1 with 10 mM TRIS Puffer pH 7

Benzoyl-Tyrosine p-nitroanilide (BTPNA): 0.5 mg/mL in Acetone

Study:

(1) 30 µl buffer (10 mM TRIS, pH=7)+20 µl $CuSO_4$ dil. (5 mM)+100 µl Chymotrypsin Stock: 30 min. incubation, then addition of 50 µl BTPNA (2) 30 µl buffer (10 mM TRIS, pH=7)+100 µl Chymotrypsin Stock: 30 min. incubation, then addition of 20 µl $CuSO_4$ dil. (5 mM)+50 µl BTPNA Three independent experiments with the above setup were carried out.

Final copper concentration: 0.5 mM

Values were corrected (subtraction of blank)

Results:

Pre-incubation of copper and chymotrypsin increases the chymotrypsin inhibitory activity (see FIG. 7).

Example 15

Chymotrypsin Inhibition by Iron(II)-Bisglycinate and Copper Gluconate

Stock Solutions:

Iron(II)-bisglycinate solution containing 1.86 mM of iron in 10 mM TRIS buffer pH 7 was prepared Cu(II)-gluconate solution containing 2.0 mM of copper in 10 mM TRIS buffer pH 7 was prepared Benzoyl-Tyrosine p-nitroanilide (BTPNA): 0.5 mg/mL BTPNA in Acetone Study:

(1) 100 µl buffer (10 mM TRIS, pH=7)+50 µl Chymotrypsin Stock+50 µl BTPNA (2) 100 µl iron(II)-bisglycinate+50 µl Chymotrypsin Stock+50 µl BTPNA (3) 100 µl copper(II)-gluconate+50 µl Chymotrypsin Stock+50 µl BTPNA Absorption was measured directly at 405 nm.

Values were corrected (subtraction of blank). Inhibition was calculated by setting the absorption value of (1) at each time-point as 100%.

Results:

Iron bisglycinate and copper gluconate can inhibit chymotrypsin, as reflected by the inhibition data shown in the following table.

| Metal ion | | | Inhibition % | | | | |
|---|---|---|---|---|---|---|---|
| | concentration | mM | 0 | 15 | 30 | 45 | 60 |
| Control | 0 mg/ml | 0.92 | 0 | 0 | 0 | 0 | 0 |
| Fe-bisglycinate | 0.06 mg/ml | 0.92 | 0 | 69 | 62 | 56 | 52 |
| Cu-gluconate | 0.065 mg/ml | 1.0 | 0 | 82 | 84 | 82 | 79 |

Minutes

Example 16

Chymotrypsin Inhibition by Iron(II)-Bisglycinate and Copper(II)-Bisglycinate Stock Solutions:
Iron(II)-bisglycinate solution containing 0.46 mM of iron in 10 mM TRIS buffer pH 7 was prepared
Cu(II)-bisglycinate solution containing 0.46 mM of copper in 10 mM TRIS buffer pH 7 was prepared
Benzoyl-Tyrosine p-nitroanilide (BTPNA): 0.5 mg/mL BTPNA in Acetone
Study:
(1) 100 µl buffer (10 mM TRIS, pH=7)+50 µl Chymotrypsin Stock+50 µl BTPNA
(2) 100 µl iron(II)-bisglycinate+50 µl Chymotrypsin Stock+50 µl BTPNA
(3) 100 µl copper(II)-bisglycinate+50 µl Chymotrypsin Stock+50 µl BTPNA Absorption was measured directly at 405 nm.
Values were corrected (subtraction of blank). Inhibition (%) was calculated by setting the absorption value of (1) at each time-point as 100% degradation.
Results:
Iron-bisglycinate and copper-bisglycinate can inhibit chymotrypsin, as reflected by the inhibition data shown in the following table.

|  | Metal ion | | Inhibition % | | | |
| --- | --- | --- | --- | --- | --- | --- |
|  | concentration | mM | 0 | 10 | 20 | 30 |
| Copper-bisglycinate | 0.015 mg/ml | 0.23 | 0 | 36 | 36 | 35 |
| Iron-bisglycinate | 0.015 mg/ml | 0.23 | 0 | 35 | 31 | 24 |
| Control | 0 mg/ml | 0.23 | 0 | 0 | 0 | 0 |

Minutes

Example 17

Chymotrypsin Inhibition by Copper Gluconate, EDTA, Sucrose Laurate and Combinations thereof Stock Solutions:
Sucrose laurate 4 mg/ml in 10 mM TRIS pH 7 was prepared
Copper gluconate 10 mM in 10 mM TRIS buffer pH 7 was prepared
EDTA 5 mM in 10 mM TRIS buffer pH 7 was prepared
Benzoyl-Tyrosine p-nitroanilide (BTPNA): 0.5 mg/mL BTPNA in Acetone
0.1 mg/ml Chymotrypsin
Study:
(1) 100 µl buffer (10 mM TRIS, pH=7)+50 µl Chymotrypsin Stock+50 µl BTPNA
(2) 50 µl Sucrose laurate+50 µl buffer (10 mM TRIS, pH=7)+50 µl Chymotrypsin Stock+50 µl BTPNA
(3) 25 µl EDTA+75 µl buffer (10 mM TRIS, pH=7)+50 µl Chymotrypsin Stock+50 µl BTPNA
(4) 25 µl copper gluconate+75 µl buffer (10 mM TRIS, pH=7)+50 µl Chymotrypsin Stock+50 µl BTPNA
(5) 25 µl EDTA+50 µl Sucrose laurate+25 µl buffer (10 mM TRIS, pH=7)+50 µl Chymotrypsin Stock+50 µl BTPNA
(6) 25 µl EDTA+25 µl copper gluconate+50 µl buffer (10 mM TRIS, pH=7)+50 µl Chymotrypsin Stock+50 µl BTPNA
(7) 50 µl sucrose laurate+25 µl copper gluconate+25 µl buffer (10 mM TRIS, pH=7)+50 µl Chymotrypsin Stock+50 µl BTPNA
(8) 25 µl EDTA+25 µl copper gluconate+50 µl sucrose laurate (10 mM TRIS, pH=7)+50 µl Chymotrypsin Stock+50 µl BTPNA Absorption was measured directly at 405 nm.
Values were corrected (subtraction of blank). pH was confirmed to be pH 7 after the experiment.
Results:
Copper gluconate and EDTA as well as combinations of copper gluconate+EDTA, EDTA+sucrose laurate and combinations of copper gluconate+EDTA+sucrose laurate can inhibit chymotrypsin (see FIG. 8).

Example 18

Chymotrypsin Inhibition by Copper Gluconate, EDTA, Sodium Caprylate and Combinations thereof Stock Solutions:
Sodium caprylate 4 mg/ml in 10 mM TRIS pH 7 was prepared
Copper gluconate 10 mM in 10 mM TRIS buffer pH 7 was prepared
EDTA 5 mM in 10 mM TRIS buffer pH 7 was prepared
Benzoyl-Tyrosine p-nitroanilide (BTPNA): 0.5 mg/mL BTPNA in Acetone
0.1 mg/ml Chymotrypsin
Study:
(1) 100 µl buffer (10 mM TRIS, pH=7)+50 µl Chymotrypsin Stock+50 µl BTPNA
(2) 50 µl sodium caprylate+50 µl buffer (10 mM TRIS, pH=7)+50 µl Chymotrypsin Stock+50 µl BTPNA
(3) 25 µl EDTA+75 µl buffer (10 mM TRIS, pH=7)+50 µl Chymotrypsin Stock+50 µl BTPNA
(4) 25 µl copper gluconate+75 µl buffer (10 mM TRIS, pH=7)+50 µl Chymotrypsin Stock+50 µl BTPNA
(5) 25 µl EDTA+50 µl sodium caprylate+25 µl buffer (10 mM TRIS, pH=7)+50 µl Chymotrypsin Stock+50 µl BTPNA
(6) 25 µl EDTA+25 µl copper gluconate+50 µl buffer (10 mM TRIS, pH=7)+50 µl Chymotrypsin Stock+50 µl BTPNA
(7) 50 µl sodium caprylate+25 µl copper gluconate+25 µl buffer (10 mM TRIS, pH=7)+50 µl Chymotrypsin Stock+50 µl BTPNA (turbid, could not be measured)
(8) 25 µl EDTA+25 µl copper gluconate+50 µl sodium caprylate (10 mM TRIS, pH=7)+50 µl Chymotrypsin Stock+50 µl BTPNA Absorption was measured directly at 405 nm.
Values were corrected (subtraction of blank). pH was confirmed to be pH 7 after the experiment.
Results:
Copper gluconate and EDTA as well as combinations of copper gluconate+EDTA, EDTA+sodium caprylate (C8) and combinations of copper gluconate+EDTA+sodium caprylate (C8) can inhibit chymotrypsin (see FIG. 9).

Example 19

Chymotrypsin Inhibition by Copper Gluconate, Sodium Caprylate and Tween 20+/− EDTA Stock Solutions:
1 mg/mL Cu(II)gluconate in 10 mM TRIS pH 7 (copper content=14%), 0.14 mg/ml copper
EDTA 5 mM in 10 mM TRIS buffer pH 7 was prepared
Sodium caprylate (C8): 1 mg/mL in 10 mM TRIS pH 7
Tween 20 (1): 1 mg/mL in 10 mM TRIS pH 7
Tween 20 (2): 2 mg/mL in 10 mM TRIS pH 7
0.1 mg/ml Chymotrypsin in 10 mM TRIS pH 7
Benzoyl-Tyrosine p-nitroanilide (BTPNA): 0.5 mg/mL BTPNA in Acetone
Study:
(1) 50 µl copper stock+20 µl C8+20 µL Tween 20 (1)+20 µL EDTA+50 µL Chymotrypsin Stock+50 µL BTPNA Stock
(2) 50 µl copper stock+20 µl C8+20 µL Tween 20 (2)+20 µL EDTA+50 µL Chymotrypsin Stock+50 µL BTPNA Stock
(3) 50 µl copper stock+20 µl C8+20 µL Tween 20 (1)+20 µLbuffer+50 µL Chymotrypsin Stock+50 µL BTPNA Stock
(4) 50 µl copper stock+20 µl C8+20 µL Tween 20 (2)+20 µLbuffer+50 µL Chymotrypsin Stock+50 µL BTPNA Stock
(5) 25 µl EDTA+25 µl copper gluconate+50 µl buffer (10 mM TRIS, pH=7)+50 µl Chymotrypsin Stock+50 µl BTPNA
(6) 50 µl sodium caprylate+25 µl copper gluconate+25 µl buffer (10 mM TRIS, pH=7)+50 µl Chymotrypsin Stock+50 µl BTPNA (turbid, could not be measured)
(7) 25 µl EDTA+25 µl copper gluconate+50 µl sodium caprylate (10 mM TRIS, pH=7)+50 µl Chymotrypsin Stock+50 µl BTPNA
Results:
Addition of EDTA to a solution of copper gluconate, Tween 20 and sodium caprylate has a positive effect on chymotrypsin inhibition (see also FIG. 10).

Example 20

Trypsin Inhibition by Copper Gluconate, Copper Lysinate and Iron Gluconate

Stock Solutions:
Benzoyl-Arginine p-nitroanilide (BAPNA): 0.5 mg/ml in 50 mM TRIS pH 7 (centrifuged and supernatant used as stock solution)
Trypsin: 0.2mg/mL in 50 mM TRIS pH 7
1 mg/mL iron gluconate in 10 mM TRIS pH 7 (iron content=12%), 0.12 mg/ml iron
1 mg/mL copper gluconate in 10 mM TRIS pH 7 (copper content=14%), 0.14 mg/ml copper
12 mg/mL copper lysinate in 10 mM TRIS pH 7 (copper content=3%), 0.12 mg/ml copper
Solution was centrifuged (to remove the white precipitate) and the blue, clear supernatant was used for the experiments
Study:
100 µl of the respective salt solution+50 µL Trypsin Stock+50 µL BAPNA Stock Results:
In the used concentrations, trypsin can be inhibited by copper(II)gluconate, iron(II)gluconate and copper(II)lysinate (see FIG. 11).

Example 21

Trypsin Inhibition by Copper Gluconate, Lauryl-Glutamate and a Combination thereof Final Concentrations:
Experiments were carried out at pH 7, 50 mM TRIS.
0.025 mg/ml Trypsin, 0.125 mg/mL Benzoyl-Arginine p-nitroanilide (BAPNA.) Lauryl glutamate:
0.25 mg/ml; copper content (as copper(II)gluconate): 0.035 mg/ml.
Study:
50 µL lauryl-glutamate stock (or buffer)+50 µL copper gluconate stock (or buffer)+50 µL
Trypsin Stock+50 µL BAPNA Stock
Adsorption measurement at 405 nm
Results:
Trypsin can be inhibited by copper gluconate and lauryl-glutamate; a combination of lauryl-glutamate and copper gluconate is a more potent trypsin inhibitor system than the lauryl-glutamate or copper gluconate alone (see FIG. 12).

Example 22

Trypsin Inhibition by Iron Gluconate, Lauryl-Glutamate and a Combination thereof Final Concentrations:
Experiments were carried out at pH 7, 50 mM TRIS.
0.025 mg/ml Trypsin, 0.125 mg/mL Benzoyl-Arginine p-nitroanilide (BAPNA). lauryl-glutamate:
0.25 mg/ml; iron (as iron gluconate): 0.03 mg/ml.
Study:
50 µL lauryl-glutamate stock (or buffer)+50 µL iron gluconate stock (or buffer)+50 µL Trypsin Stock+50 µL BAPNA Stock
Absorption measurement at 405 nm
Results:
Trypsin can be inhibited by iron gluconate and lauryl-glutamate; a combination of lauryl-glutamate and iron gluconate is a more potent trypsin inhibitor system than the lauryl-glutamate or iron gluconate alone (see FIG. 13).

Example 23

Chymotrypsin Inhibition by Copper Gluconate, Lauryl-Glutamate and a Combination thereof Final Concentrations:
Experiments were carried out at pH 7, 50 mM TRIS.
0.025 mg/ml Chymotrypsin, 0.05 mg/mL Benzoyl-Tyrosine p-nitroanilide (BTPNA). Lauryl glutamate: 0.25 mg/ml; copper (as copper gluconate): 0.035 mg/ml.
Study:
50 µL lauryl-glutamate stock (or buffer)+50 µL copper gluconate stock (or buffer)+50 µL Trypsin Stock+50 µL BTPNA Stock
Absorption measurement at 405 nm
Results:
Chymotrypsin can be inhibited by copper gluconate; a combination of lauryl-glutamate and copper gluconate is a more potent chymotrypsin inhibitor system than lauryl-glutamate or copper gluconate alone (see FIG. 14).

Example 24

Chymotrypsin Inhibition by Iron Gluconate, Lauryl-Glutamate and a Combination thereof Final Concentrations:
Experiments were carried out at pH 7, 50 mM TRIS.
0.025 mg/ml Chymotrypsin, 0.05 mg/mL Benzoyl-Tyrosine p-nitroanilide (BTPNA). Lauryl glutamate: 0.25 mg/ml; iron (as iron gluconate): 0.03 mg/ml.
Study:
50 µL lauryl-glutamate stock (or buffer)+50 µL iron gluconate stock (or buffer)+50 µL Trypsin Stock+50 µL BTPNA Stock
Absorption measurement at 405 nm
Results:
Chymotrypsin can be inhibited by iron gluconate; a combination of lauryl-glutamate and iron gluconate is a more potent chymotrypsin inhibitor system than lauryl-glutamate or iron gluconate alone (see FIG. 15).

Example 25

Trypsin Inhibition by Iron Gluconate, Capryl-Glucoside and a Combination thereof Final Concentrations:
Experiments were carried out at pH 7, 50 mM TRIS.
0.025 mg/ml Trypsin, 0.125 mg/mL Benzoyl-Arginine p-nitroanilide (BAPNA). Capryl-glucoside: 0.25 mg/ml; iron (as iron gluconate): 0.03 mg/ml.
Study:
50 µL capryl-glucoside (or buffer)+50 µL iron gluconate stock (or buffer)+50 µL Trypsin Stock+50 µL BAPNA Stock
Absorption measurement at 405 nm
Results:
Trypsin can be inhibited by iron gluconate and a combination of iron gluconate +capryl-glucoside (see FIG. 16).

Example 26

Trypsin Inhibition by Copper Sulfate, Copper Tartrate and Zinc Orotate

Stock Solutions:
Copper sulfate stock solution: 1 mg/ml of copper sulfate was dissolved in 50 mM TRIS pH 7. Copper tartrate stock solution: 1 mg/ml of copper tartrate was dispersed in 50 mM TRIS pH 7 and moderately stirred for 5 minutes. The suspension was then centrifuged at 3'000 rpm for 10 minutes, to separate the insoluble salt. The supernatant was used as stock solution for the experiments.
Zinc orotate stock solution: 1 mg/ml of zinc orotate was dispersed in 50 mM TRIS pH 7 and moderately stirred for 5 minutes. The suspension was then centrifuged at 3'000 rpm for 10 minutes, to separate the insoluble salt. The supernatant was used as stock solution for the experiments.
Study:
100 µL of the respective salt solution stock+50 µL Trypsin Stock+50 µL BAPNA Stock
Control: 100 µL of 50 mM TRIS pH 7+50 µL Trypsin Stock+50 µL BAPNA Stock
Experiments were carried out at pH 7, 50 mM TRIS.
Final concentrations of protease and substrate were 0.025 mg/ml Trypsin, 0.125 mg/mL
Benzoyl-Arginine p-nitroanilide (BAPNA)
Absorption measurement at 405 nm
Results:
Trypsin can be strongly inhibited by copper sulfate. Despite their poor solubilities in water, copper tartrate and zinc orotate show trypsin inhibitory properties in vitro (see FIG. 17).

Example 27

Chymotrypsin Inhibition by Copper Gluconate, Beta-Cyclodextrin and a Combination thereof Stock Solutions:
0.1 mg/ml Chymotrypsin
1 mg/mL Benzoyl-Tyrosine p-nitroanilide (BTPNA)
1mg/ml Beta-cyclodextrin
2.5 mM copper(II)gluconate
Study:
100 µl 50 mM TRIS pH 7+50 µL Chymotrypsin Stock+50 µL BTPNA Stock
50 µl Beta-cyclodextrin+50 µl 50 mM TRIS pH 7+50 µL Chymotrypsin Stock+50 µL BTPNA Stock
50 µl copper gluconate+50 µl 50 mM TRIS pH 7+50 µL Chymotrypsin Stock+50 µL BTPNA Stock
50 µl copper gluconate+50 µl Beta-cyclodextrin+50 µL Chymotrypsin Stock+50 µL BTPNA Stock
Results:
Chymotrypsin can be inhibited by copper gluconate and a combination of copper gluconate+beta-cyclodextrin (see FIG. 18).

Example 28

Trypsin Inhibition by Copper Gluconate and a Combination of Copper Gluconate+Manganese Sulfate Stock Solutions:
0.1 mg/ml Trypsin
0.5 mg/mL Benzoyl-Arginine p-nitroanilide (BAPNA)
1 mg/ml copper(II)gluconate
1 mg/ml manganese(II)sulfate
Study:
Experiments were carried out at pH 7 in 50 mM TRIS buffer.
Final concentrations of protease and substrate were 0.25 mg/ml Trypsin, 0.125 mg/mL BAPNA.
100 µl 50 mM TRIS pH 7+50 µL Trypsin Stock+50 µL BAPNA Stock
50 µl copper gluconate+50 µl 50 mM TRIS pH 7+50 µL Trypsin Stock+50 µL BAPNA Stock
50 µl manganese sulfate+50 µl copper gluconate+50 µL Trypsin Stock+50 µL BAPNA Stock
Absorption measurement at 405 nm; final pH in all solutions was monitored to be pH 7.
Results:
Trypsin can be inhibited by copper gluconate and a combination of copper gluconate and manganese sulfate (see FIG. 19).

Example 29

Trypsin Inhibition by Combinations of Copper Gluconate+SiO₂ and Iron Gluconate+SiO₂

Stock Solutions:
0.1 mg/ml Trypsin
0.5 mg/mL Benzoyl-Arginine p-nitroanilide (BAPNA)
3 mg/ml SiO₂—suspended in 50 mM TRIS pH 7 and centrifuged; supernatant was used for experiments.
1 mg/ml copper(II)gluconate
1 mg/ml iron(II)gluconate Study:
100 µl 50 mM TRIS pH 7+50 µL Trypsin Stock+50 µL BAPNA Stock
50 µl SiO₂+50 µl 50 mM TRIS pH 7+50 µL Trypsin Stock+50 µL BAPNA Stock
50 µl copper gluconate+50 µl SiO₂+50 µL Trypsin Stock+50 µL BAPNA Stock
50 µl iron gluconate+50 µl SiO₂+50 µL Trypsin Stock+50 µL BAPNA Stock Absorption measurement at 405 nm; final pH in all solutions was monitored to be pH 7.

Experiments were carried out at pH 7 in 50 mM TRIS buffer.

Results:
Trypsin can be inhibited by combinations of copper gluconate+SiO₂ and iron gluconate+SiO₂ (see FIG. 20).

Example 30

Chymotrypsin Inhibition by Combinations of Copper Gluconate+Trisodium Phosphate and Iron Gluconate+Trisodium Phosphate Stock Solutions:
0.1 mg/ml Chymotrypsin
0.5 mg/mL Benzoyl-Tyrosine p-nitroanilide (BTPNA) in Acetone
2.5 mg/ml trisodium phosphate
1 mg/ml copper(II)gluconate
1 mg/ml iron(II)gluconate Study:
100 µl 50 mM TRIS pH 7+50 µL Chymotrypsin Stock+50 µL BTPNA Stock
50 µl copper gluconate+50 µl trisodium phosphate+50 µL Chymotrypsin Stock+50 µL BTPNA Stock
50 µl iron gluconate+50 µl trisodium phosphate+50 µL Chymotrypsin Stock+50 µL BTPNA Stock Experiments were carried out at pH 7 in 50 mM TRIS buffer.

Absorption measurement at 405 nm; final pH in the control solution was monitored to be pH 7;
pH in all other solutions was between 7 and 7.5.

Results:
Chymotrypsin can be inhibited by combinations of copper gluconate+trisodium phosphate and iron gluconate+trisodium phosphate (see FIG. 21).

Example 31

Chymotrypsin Inhibition by Copper Gluconate, EDTA and a Combination thereof

Stock Solutions:
0.1 mg/ml Chymotrypsin
0.5 mg/mL Benzoyl-Tyrosine p-nitroanilide (BTPNA) in Acetone
2.5 mM copper(II)gluconate
1.25 mM EDTA Study:
100 µl 50 mM TRIS pH 7+50 µL Chymotrypsin Stock+50 µL BTPNA Stock
50 µl copper gluconate+50 µl 10 mM TRIS pH 7+50 µL Chymotrypsin Stock+50 µL BTPNA Stock
50 µl EDTA+50 µl 10 mM TRIS pH 7+50 µL Chymotrypsin Stock+50 µL BTPNA Stock
50 µl copper gluconate+50 µl EDTA+50 µL Chymotrypsin Stock+50 µL BTPNA Stock Experiments were carried out at pH 7 in 10 mM TRIS buffer.

Adsorption measurement at 405 nm; final pH in the control solution was monitored to be pH 7.

Results:
Chymotrypsin can be inhibited by EDTA and copper gluconate. A combination of copper gluconate and EDTA is a more potent inhibitor system than EDTA or copper gluconate only (see FIG. 22).

Example 32

Solubility of Cu(II)-Bisglycinate in the Presence of Sorbitol

Stock Solutions:
A solution of 80 mg/mL Sorbitol in Aqua dest. was prepared
A supersaturated solution of Cu(II)-bisglycinate was prepared by adding 24 mg of copper salt to 500 µl of Aqua dest.
(1) To 250 µl of the supersaturated copper solution, 250 µl of Aqua dest. was added
(2) To 250 µl of the supersaturated copper solution, 250 µl of the Sorbitol solution was added Study:
Both dispersions (1) and (2) were centrifuged at room temperature at 2'000 rpm for 5 minutes. Then the absorption of the supernatant was measured at 450 nm. Blank values of Aqua dest. and the Sorbitol solution were the same and were subtracted from the measured values. Calibration curve with copper in Aqua dest. and copper in Sorbitol solution were prepared, demonstrating linear behaviour.

Results:
The solubility of copper-bisglycinate in the presence of sorbitol increased (+50%) in comparison to the solubility of copper-bisglycinate in Aqua dest.

Example 33

Trypsin Inhibition by Copper Gluconate, Iron Gluconate and Combinations thereof Stock Solutions:
0.1 mg/ml Trypsin
0.5 mg/mL Benzoyl-Arginine p-nitroanilide (BAPNA)
1 mg/ml copper(II)gluconate
1 mg/ml iron(II)gluconate Study:

120 µl 50 mM TRIS pH 7+50 µL Trypsin Stock+50 µL BAPNA Stock

80 µl copper gluconate+40 µl 50 mM TRIS pH 7+50 µL Trypsin Stock+50 µL BAPNA Stock 40 µl copper gluconate+80 µl 50 mM TRIS pH 7+50 µL Trypsin Stock+50 µL BAPNA Stock 80 µl iron gluconate+40 µl 50 mM TRIS pH 7+50 µL Trypsin Stock+50 µL BAPNA Stock 40 µl iron gluconate+80 µl 50 mM TRIS pH 7+50 µL Trypsin Stock+50 µL BAPNA Stock 80 µl iron gluconate+40 µl copper gluconate+50 µL Trypsin Stock+50 µL BAPNA Stock 40 µl iron gluconate+80 µl copper gluconate+50 µL Trypsin Stock+50 µL BAPNA Stock Experiments were carried out at pH 7 in 50 mM TRIS buffer.

Absorption measurement at 405 nm

Results:

Trypsin can be inhibited by copper gluconate, iron gluconate and any combination thereof. Combinations of iron gluconate and copper gluconate are the most potent inhibitor systems (see FIG. 23).

Example 34

Pharmacokinetic Profile of Teriparatide Formulations after Administration into Proximal Jejunum Teriparatide formulations were dosed into proximal jejunum in volume of 0.4 ml/kg (final concentration 0.42 mg/ml teriparatide) to anaesthetized rats. Blood was taken from tail vessels at the time points 0, 10, 20, 40, 60, 90, 120 and 180 min after dosing. The teriparatide plasma concentrations were determined using commercial high sensitivity teriparatide ELISA kit (Immutopics Inc., USA, cat.number 60-3900).

TER092
0.42 mg/ml Teriparatide
60 mg/ml Sucrose laurate
5 mg/ml Copper(II)gluconate
(pH of final formulation=4.4)

TER093
0.42 mg/ml Teriparatide
60 mg/ml Sucrose laurate
5 mg/ml Iron(11)gluconate
(pH of final formulation=4.5)

TER095
0.42 mg/ml Teriparatide
40 mg/ml SNAG
20 mg/ml SDS
2.5 mg/ml EDTA
5 mg/ml Copper(II)glycinate
(pH of final formulation=7.0)

Results: The formulation TER095 was rapidly absorbed and exhibited the highest Cmax and AUC. The formulations TER092 and TER093 were more slowly absorbed and had longer elimination half-life. The results are shown in the following table:

Pharmacokinetic Parameters:

|  | $AUC_{(0-180)}$ (ng/ml × min) | $C_{max}$ (ng/ml) | Half-life (min) |
|---|---|---|---|
| TER092 | 17898 ± 8328 | 0.173 ± 0.085 | 71.4 ± 13.6 |
| TER093 | 15327 ± 11588 | 0.174 ± 0.119 | 61.4 ± 26.2 |
| TER095 | 48307 ± 16335 | 0.670 ± 0.164 | 56.9 ± 9.6 |

Example 35

Leuprolide Acetate Formulations for Oral administration

LEU007
HPMC capsule
3.5 mg Leuprolide acetate
300 mg Sodium caprylate
200 mg Sodium citrate
10 mg Copper(II)gluconate LEU008
AR capsule (acid resistant capsule)
3.5 mg Leuprolide
100 mg Sodium dodecyl sulfate
100 mg Mannitol
10 mg Copper(II)gluconate
5 mg EDTA

The invention claimed is:

1. A method of orally delivering a peptide drug, the method comprising orally administering a pharmaceutical composition to a subject in need thereof, wherein the pharmaceutical composition comprises:
 a peptide drug having a molecular weight of equal to or less than 5 kDa and having at least one serine protease cleavage site;
 a pharmaceutically acceptable copper complex and/or a pharmaceutically acceptable zinc complex and/or a pharmaceutically acceptable iron complex,
  wherein said copper complex is selected from the group consisting of a copper(II) amino acid complex, copper(II) lysine complex, copper(II) glycinate, copper(II) EDTA complex, copper(II) chitosan complex, copper(II) citrate, copper(II) gluconate, copper(II) lactate, copper(II) lactate gluconate, and copper(II) orotate,
  wherein said zinc complex is a zinc(II) complex which is selected from the group consisting of zinc ascorbate, zinc caprylate, zinc gluconate, zinc stearate, zinc orotate, a zinc amino acid complex, zinc glycinate, zinc arginate, zinc picolinate, zinc pidolate, zinc carnosine, zinc undecanoate, zinc undecylenate, zinc methionine, zinc lactate, and zinc lactate gluconate,
  wherein the iron complex is selected from the group consisting of iron(II) gluconate, iron(II) orotate, iron(II) tartrate, iron(II) fumarate, iron(II) lactate, iron(II) lactate gluconate, iron(II) citrate, iron(II) ascorbate, an iron(II) amino acid complex, ferrous bisglycinate, iron(III) tartrate, iron(III) lactate, iron(III) glycinate, iron(III) EDTA, iron(III) ascorbate, and ammonium iron(III) citrate;
 a pharmaceutically acceptable complexing agent; and
 an adsorption enhancer, wherein the absorption enhancer selected from the group consisting on N-[8-(2-hydroxybenzoyl)amino]caprylic acid, sodium N-[8-(2-hydroxybenzoyl)amino]caprylate, a sodium N-[8-(2-hydroxybenzoyl)amino]caprylate derivative, a $C_{8-20}$ alkanoyl carnitine, sucrose laurate, and pharmaceutically acceptable salts thereof.

2. The method of claim 1, wherein the peptide drug has a molecular weight of about 500 Da to about 4 kDa.

3. The method of claim 1, wherein the peptide drug is selected from the group consisting of GLP-1, a GLP-1 analog, an acylated GLP-1 analog, a diacylated GLP-1 analog, a long-acting albumin-binding fatty acid-derivatized GLP-1 analog, a GLP-1 agonist, semaglutide, liraglutide, exenatide, exendin-4, lixisenatide, taspoglutide, langlenatide, GLP-1(7-37), GLP-1(7-36)NH$_2$, a dual agonist of the GLP-1 receptor and the glucagon receptor, oxyntomodulin, GLP-2, a GLP-2 agonist or analog, teduglutide, elsiglutide, amylin, an amylin analog, pramlintide, a somatostatin analog, octreotide, lanreotide, pasireotide, goserelin, buserelin, peptide YY, a peptide YY analog, glatiramer, leuprolide, desmopressin, a glycopeptide antibiotic, teicoplanin, telavancin, bleomycin, ramoplanin, decaplanin, bortezomib, cosyntropin, sermorelin, luteinizing-hormone-releasing hormone, calcitonin, calcitonin-salmon, pentagastrin, oxytocin, neseritide, enfuvirtide, eptifibatide, glucagon, viomycin, thyrotropin-releasing hormone, leucine-enkephalin, methionine-enkephalin, substance P, a parathyroid hormone fragment, teriparatide, PTH(1-31), PTH(2-34), linaclotide, carfilzomib, icatibant, cilengitide, a prostaglandin F2α receptor modulator, PDC31, and pharmaceutically acceptable salts thereof.

4. The method of claim 1, wherein said complexing agent is selected from the group consisting of mannitol, sorbitol, saccharose, sucrose, trehalose, calcium phosphate, basic calcium phosphate, calcium hydrogen phosphate, dicalcium phosphate hydrate, disodium phosphate dihydrate, an amino acid, EDTA, EGTA, citrate, a complexing peptide, glycyl-histidyl-lysine peptide, polyacrylic acid, a polyacrylic acid derivative, a carbomer, a carbomer derivative, sodium alginate, a silicate, kaolin, hydroxypropyl methylcellulose, methylcellulose, glycerol, sodium dodecyl sulfate, calcium sulfate, calcium carbonate, and pharmaceutically acceptable salts thereof.

5. The method of claim 1, wherein said absorption enhancer is sodium N-[8-(2-hydroxybenzoyl)amino]caprylate.

* * * * *

UNITED STATES PATENT AND TRADEMARK OFFICE
CERTIFICATE OF CORRECTION

| | |
|---|---|
| PATENT NO. | : 10,905,744 B2 |
| APPLICATION NO. | : 15/766546 |
| DATED | : February 2, 2021 |
| INVENTOR(S) | : Foger et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 63 days.

Signed and Sealed this
Fourteenth Day of February, 2023

Katherine Kelly Vidal
*Director of the United States Patent and Trademark Office*

SEQUENCE LISTING

<160> NUMBER OF SEQ ID NOS: 2

<210> SEQ ID NO 1
<211> LENGTH: 31
<212> TYPE: PRT
<213> ORGANISM: Homo sapiens
<220> FEATURE:
<223> OTHER INFORMATION: GLP-1(7-37)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 40

```
<212> TYPE: PRT
<213> ORGANISM: Artificial Sequence
<220> FEATURE:
<223> OTHER INFORMATION: Exendin-4

<400> SEQUENCE: 2

His Gly Glu Gly Thr Phe Ile Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser
            35              40
```